(12) United States Patent
Wong

(10) Patent No.: US 10,527,627 B2
(45) Date of Patent: Jan. 7, 2020

(54) URINARY POLYAMINES AS PROSTATE CANCER DETECTION BIOMARKERS

(71) Applicant: New Life Medicine Technology Company Limited, Hong Kong (HK)

(72) Inventor: Ka Leung Wong, Hong Kong (HK)

(73) Assignee: New Life Medicine Technology Company Limited, Hong Kong (HK)

( * ) Notice: Subject to any disclaimer, the term of this patent is extended or adjusted under 35 U.S.C. 154(b) by 192 days.

(21) Appl. No.: 15/784,269

(22) Filed: Oct. 16, 2017

(65) Prior Publication Data

US 2018/0172695 A1 Jun. 21, 2018

Related U.S. Application Data

(60) Provisional application No. 62/471,989, filed on Mar. 16, 2017, provisional application No. 62/409,361, filed on Oct. 17, 2016.

(51) Int. Cl.
| | | |
|---|---|---|
| *G01N 33/00* | (2006.01) | |
| *G01N 33/58* | (2006.01) | |
| *C07F 19/00* | (2006.01) | |
| *C07D 403/14* | (2006.01) | |
| *G01N 33/52* | (2006.01) | |
| *G01N 33/574* | (2006.01) | |
| *C07D 333/22* | (2006.01) | |

(52) U.S. Cl.
CPC ......... *G01N 33/583* (2013.01); *C07D 333/22* (2013.01); *C07D 403/14* (2013.01); *C07F 19/005* (2013.01); *G01N 33/52* (2013.01); *G01N 33/57434* (2013.01); *G01N 33/587* (2013.01)

(58) Field of Classification Search
CPC .................................................... G01N 33/583
USPC .......................................................... 436/64
See application file for complete search history.

(56) References Cited

PUBLICATIONS

Zhuang et al. "Photo-reactive charge trapping memory based on lanthanide complex" Sci. Rep. 5, 14998; doi: 10.1038/srep14998 (2015) (Year: 2015).*

Seiler et al.; Polyamine Transport in Mammalian Cells; The International Journal of Biochemistry & Cell Biology; Aug. 1996; pp. 843-861; vol. 28, Issue 8; Elsevier Science Ltd; United Kingdom.

Tabor et al.; 1, 4-Diaminobutane (Putrescine), Spermidine, and Spermine; Annual Review of Biochemistry; Jun. 1, 1976; pp. 285-306; vol. 45; Annual Reviews; United States.

Cipolla et al.; Pretherapeutic Erythrocyte Polyamine Spermine Levels Discriminate High Risk Relapsing Patients with M1 Prostate Carcinoma; Cancer; Sep. 1, 1996; pp. 1055-1065; vol. 78, Issue 5; Wiley-Blackwell; Jnited States.

Stefanelli et al.; Spermine Causes Caspase Activation in Leukaemia Cells; FEBS Letters; Oct. 23, 1998, pp. 233-236; vol. 437, Issue 3; Wiley; United States.

(Continued)

*Primary Examiner* — Christine T Mui
*Assistant Examiner* — Emily R. Berkeley
(74) *Attorney, Agent, or Firm* — Spruson & Ferguson (Hong Kong) Limited

(57) ABSTRACT

The present disclosure relates to urinary polyamines useful as prostate cancer biomarkers. In particular, the present disclosure provides a novel, highly-sensitive and specific, method for detecting and quantifying urinary polyamines using lanthanide complexes or citrate capped gold nanoparticles.

6 Claims, 53 Drawing Sheets

Specification includes a Sequence Listing.

(56) References Cited

PUBLICATIONS

Gerner et al.; Polyamines and Cancer: Old Molecules, New Understanding; Nature Reviews Cancer; Oct. 2004; pp. 781-792; vol. 4, Issue 10; Nature Publishing Group; United Kingdom.

Ha et al.; The Natural Polyamine Spermine Functions Directly as a Free Radical Scavenger; Proceedings of the National Academy of Sciences of the United States of America; Sep. 15, 1998; pp. 11140-11145; vol. 95, Issue 19; The National Academy of Sciences; United States.

Igarashi et al.; Modulation of Cellular Function by Polyamines; The International Journal of Biochemistry & Cell Biology; Jan. 2010; pp. 39-51; vol. 42, Issue 1; Elsevier Ltd.; United Kingdom.

Kurata et al.; The Polyamine Binding Site in Inward Rectifier K+ Channels; The Journal of General Physiology; May 2006; pp. 467-480; vol. 127, Issue 5; The Rockefeller University Press; United States.

Lopatin et al.; Potassium Channel Block by Cytoplasmic Polyamines as the Mechanism of Intrinsic Rectification; Nature; Nov. 24, 1994; pp. 366-369; vol. 372, Issue 6504; Nature Publishing Group; United Kingdom.

Williams; Modulation and Block of Ion Channels: a New Biology of Polyamines; Cellular Signalling; Jan. 1997, pp. 1-13; vol. 9, Issue 1; Elsevier Science Inc.; United States.

Russell et al.; Amine Synthesis in Rapidly Growing Tissues: Ornithine Decarboxylase Activity in Regenerating Rat Liver, Chick Embryo, and Various Tumors; Proceedings of the National Academy of Sciences of the United States of America; Aug. 15, 1968; pp. 1420-1427; vol. 60, Issue 4; The National Academy of Sciences; United States.

Russell et al.; Urinary Polyamines in Cancer Patients; Cancer Research; Nov. 1971; pp. 1555-1558; vol. 31, Issue 11; American Association for Cancer Research; United States.

Lee et al.; Altered Urinary Profiles of Polyamines and Endogenous Steroids in Patients with Benign Cervical Disease and Cervical Cancer; Cancer Letters; Nov. 25, 2003; pp. 121-131; vol. 201, Issue 2; Elsevier Ireland Ltd.; Ireland.

Löser et al.; Polyamines in Colorectal Cancer. Evaluation of Polyamine Concentrations in the Colon Tissue, Serum, and Urine of 50 Patients with Colorectal Cancer; Cancer; Feb. 15, 1990; pp. 958-966; vol. 65, Issue 4; Wiley-Blackwell; United States.

Levêque et al.; Polyamine Profiles in Tumor, Normal Tissue of the Homologous Breast, Blood, and Urine of Breast Cancer Sufferers; Breast Cancer Research and Treatment; Mar. 2000; pp. 99-105; vol. 60, Issue 2; Kluwer Academic Publishers; Netherlands.

Schröder et al.; Evaluation of the Digital Rectal Examination as a Screening Test for Prostate Cancer; Journal of the National Cancer Institute; Dec. 2, 1998, pp. 1817-1823; vol. 90, Issue 23; Oxford University Press; United Kingdom.

Rigau et al.; The Present and Future of Prostate Cancer Urine Biomarkers; International Journal of Molecular Science; Jun. 17, 2013; pp. 12620-12649; vol. 14, Issue 6; Multidisciplinary Digital Publishing Institute; Switzerland.

Wu et al.; Effect of Local Anesthetics on Patient Recovery after Transrectal Biopsy; Urology; May 2001; pp. 925-929; vol. 57, Issue 5; Elsevier Science Inc.; United States.

Chan et al.; Randomized Controlled Trial of Antibiotic Prophylaxis Regimens for Transrectal Ultrasound-Guided Prostate Biopsy; Chinese Medical Journal; Jul. 20, 2012; pp. 2432-2435; vol. 125, Issue 14; Chinese Medical Association Publishing House / Wolters Kluwer Medknow; China.

Wagenlehner et al.; Infective Complications after Prostate Biopsy: Outcome of the Global Prevalence Study of Infections in Urology (GPIU) 2010 and 2011, a Prospective Multinational Multicentre Prostate Biopsy Study; European Urology; Mar. 2013; pp. 521-527; vol. 63, Issue 3; Elsevier B.V.; Netherlands.

Tsoi et al.; Urinary Polyamines: a Pilot Study on Their Roles as Prostate Cancer Detection Biomarkers; Plos One; Sep. 6, 2016; vol. 11, Issue 9; Public Library of Science; United States.

Al-Hadithi et al.; Determination of Underivatized Polyamines: a Review of Analytical Methods and Applications; Analytical Letters; Sep. 6, 2011; pp. 2245-2264; vol. 44, Issue 13; Taylor & Francis Group; United States.

Kim et al.; Analyte-Directed Formation of Emissive Excimers for the Selective Detection of Polyamines; Chemical Communications; Aug. 4, 2016, pp. 10648-10651; vol. 52, Issue 70; The Royal Society of Chemistry; United Kingdom.

Chopra et al.; Colorimetric Detection of Spermine by the Cull Complex of Imine-Based Organic Nanoaggregates in Aqueous Medium; European Journal of Inorganic Chemistry; Sep. 2015; pp. 4437-4442; vol. 2015, Issue 26; Wiley-VCH Verlag GmbH & Co. KGaA; Germany.

Gu et al.; Gold-Doxorubicin Nanoconjugates for Overcoming Multidrug Resistance; Nanomedicine: Nanotechnology, Biology and Medicine; Feb. 2012; pp. 204-211; vol. 8, Issue 2; Elsevier Inc.; United States.

Sener et al.; Lysine-Promoted Colorimetric Response of Gold Nanoparticles: a Simple Assay for Ultrasensitive Mercury (II) Detection; Analytical Chemistry; Jan. 7, 2014; pp. 514-520; vol. 86, Issue 1; ACS Publications; United States.

Guo et al.; Label-Free Colorimetric Detection of Cadmium Ions in Rice Samples Using Gold Nanoparticles; Analytical Chemistry; Sep. 2, 2014; pp. 8530-8534;vol. 86, Issue 17; ACS Publications; United States.

Feng et al.; Single Molecular Functionalized Gold Nanoparticles for Hydrogen-Bonding Recognition and Colorimetric Detection of Dopamine with High Sensitivity and Selectivity; ACS Applied Materials & Interfaces; Feb. 27, 2013; pp. 1226-1231; vol. 5, Issue 4; ACS Publications; United States.

Jornet-Martinez et al.; Sensitive and Selective Plasmonic Assay for Spermine as Biomarker in Human Urine; Analytical Chemistry; Feb. 4, 2014; pp. 1347-1351; vol. 86, Issue 3; ACS Publications; United States.

Kim et al.; A Gold Nanoparticle-Based Fluorescence Turn-On Probe for Highly Sensitive Detection of Polyamines; Chemistry: A European Journal; Oct. 17, 2011; pp. 11978-11982; vol. 17, Issue 43; Wiley-VCH Verlag GmbH & Co. KGaA; Germany.

Rawat et al.; Microwave Assisted Synthesis of Tyrosine Protected Gold Nanoparticles for Dual (Colorimetric and Florimetric) Detection of Spermine and Spermidine in Biological Samples; Biosensors and Bioelectronics; Feb. 15, 2017; pp. 71-77; vol. 88, Elsevier B.V.; Netherlands.

Liu et al.; Highly Selective Colorimetric Detection of Spermine in Biosamples on Basis of the Non-Crosslinking Aggregation of SSDNA-Capped Gold Nanoparticles; Talanta; Mar. 15, 2013; pp. 255-260; vol. 106; Elsevier B.V.; Netherlands.

Álvarez et al.; Reusable Phosphorescent Probes Based on Molecularly Imprinted Polymers for the Determination of Propranolol in Urine; Sensors and Actuators B: Chemical; Jun. 20, 2012; pp. 370-375; vol. 168; Elsevier B.V.; Netherlands.

Gu et al.; Nuclear Penetration of Surface Functionalized Gold Nanoparticles; Toxicology and Applied Pharmacology; Jun. 1, 2009; pp. 196-204; vol. 237, Issue 2; Elsevier Inc.; United States.

Turkevich et al.; A Study of the Nucleation and Growth Processes in the Synthesis of Colloidal Gold; Discussions of the Faraday Society; 1951; pp. 55-75; vol. 11; Royal Society of Chemistry; United Kingdom.

Liu et al.; Extinction Coefficient of Gold Nanoparticles with Different Sizes and Different Capping Ligands; Colloids and Surfaces B: Biointerfaces; Jul. 1, 2007; pp. 3-7; vol. 58, Issue 1; Elsevier B.V.; Netherlands.

Zhang et al.; Surface science of DNA adsorption onto citrate-capped gold nanoparticles; Langmuir; Feb. 28, 2012; pp. 3896-3902; vol. 28, Issue 8; ACS Publications; United States.

Rautaray et al.; Synthesis of Hydroxyapatite Crystals Using Amino Acid-Capped Gold Nanoparticles as a Scaffold; Langmuir; May 24, 2005; pp. 5185-5191; vol. 21, Issue 11; ACS Publications; United States.

Morgan et al.; Association Constants for the Interaction of Double-Stranded and Single-Stranded DNA with Spermine, Spermidine, Putrescine, Diaminopropane, N1- and N8-Acetylspermidine, and Magnesium: Determination from Analysis of the Broadening of

(56) References Cited

PUBLICATIONS

Thermal Denaturation Curves; Archives of Biochemistry and Biophysics; Apr. 1986; pp. 225-232; vol. 246, Issue 1; Academic Press, Inc.; United States.

Park et al.; Structural Study of Citrate Layers on Gold Nanoparticles: Role of Intermolecular Interactions in Stabilizing Nanoparticles; Journal of the American Chemical Society; Feb. 5, 2014; pp. 1907-1921; vol. 136, Issue 5; ACS Publications; United States.

Bagheryan et al.; Preparation of a New Nanobiosensor for the Determination of Some Biogenic Polyamines and Investigation of Their Interaction with DNA; Biosensors and Bioelectronics; Mar. 15, 2016, pp. 767-773; vol. 77; Elsevier B.V.; Netherlands.

Gracie et al.; Preferential Attachment Of Specific Fluorescent Dyes and Dye Labeled DNA Sequences in a Surface Enhanced Raman Scattering Multiplex; Analytical Chemistry; Jan. 19, 2016; pp. 1147-1153; vol. 88, Issue 2; ACS Publications; United States.

Xiong et al.; Simultaneous Determination of Senecionine, Adonifoline and Their Metabolites in Rat Serum by UPLC—ESIMS and Its Application in Pharmacokinetic Studies; Journal of Pharmaceutical and Biomedical Analysis; Dec. 5, 2009; pp. 1070-1074; vol. 50, Issue 5; Elsevier B.V.; Netherlands.

Tsoi et al.; A Simple, Highly Sensitive, High throughput and Organic Solvent-Free Screening Method for Melamine by Microsphere-Based Flow Cytometry Immunoassay; Analytical Methods; Jul. 21, 2015; pp. 5989-5995; vol. 7, Issue 14; The Royal Society of Chemistry; United Kingdom.

Bonsnes et al.; On the Colorimetric Determination of Creatinine by the Jaffé Reaction; Journal of Biological Chemistry; May 1, 1945; pp. 581-591; vol. 158, Issue 3; American Society for Biochemistry and Molecular Biology; United States.

Häkkinen et al.; Analysis of Free, Mono- and Diacetylated Polyamines from Human Urine by LC-MS/MS; Journal of Chromatography B: Analytical Technologies in the Biomedical and Life Sciences; Dec. 15, 2013; pp. 81-89; vol. 941; Elsevier B.V.; Netherlands.

Jung; Enzyme Activities in Urine: How Should We Express Their Excretion? A Critical Literature Review; European Journal of Clinical Chemistry and Clinical Biochemistry; Jan. 1991; pp. 725-729; vol. 29, Issue 11; Walter de Gruyter & Co.; United States.

Russel; Increased Polyamine Concentrations in the Urine of Human Cancer Patients; Nature New Biology; Sep. 29, 1971; pp. 144-145; vol. 233, Issue 39; Nature Publishing Group; United Kingdom.

Hiramatsu et al.; N1,N12-Diacetylspermine as a Sensitive and Specific Novel Marker for Early- and Late-Stage Colorectal and Breast Cancers; Clinical Cancer Research; Apr. 15, 2005; pp. 2986-2990; vol. 11, Issue 8; American Association for Cancer Research; United States.

Liu et al.; Determination of Polyamine Metabolome in Plasma and Urine by Ultrahigh Performance Liquid Chromatography-Tandem Mass Spectrometry Method: Application to Identify Potential Markers for Human Hepatic Cancer; Analytica Chimica Acta; Aug. 12, 2013; pp. 36-45; vol. 791; Elsevier B.V.; Netherlands.

Fair et al.; Urinary Polyamine Levels in the Diagnosis of Carcinoma of the Prostate; The Journal of Urology; Jul. 1975; pp. 88-92; vol. 114, Issue 1; The Williams & Wilkins Co.; United States.

Horn et al.; Relationship of Urinary Polyamines to Tumor Activity and Tumor Volume in Patients; Cancer Research; Oct. 1984; pp. 4675-4678; vol. 44, Issue 10; American Association for Cancer Research; United States.

Graaf et al.; Proton MR Spectroscopy of Prostatic Tissue Focused on the Detection of Spermine, a Possible Biomarker of Malignant Behavior in Prostate Cancer; Magnetic Resonance Materials in Physics, Biology and Medicine; Oct. 2000; pp. 153-159; vol. 10, Issue 3; Elsevier Science B.V.; Netherlands.

Swanson et al.; Proton HR-MAS Spectroscopy and Quantitative Pathologic Analysis of MRI/3D-MRSI-Targeted Postsurgical Prostate Tissues; Magnetic Resonance in Medicine; Nov. 2003; pp. 944-954; vol. 50, Issue 5; Wiley-Liss, Inc.; United States.

Giskeødegård et al.; Spermine and Citrate as Metabolic Biomarkers for Assessing Prostate Cancer Aggressiveness; PLOS One; Apr. 23, 2013; vol. 8, Issue 4; Public Library of Science; United States.

Serkova et al.; The Metabolites Citrate, Myo-Inositol, and Spermine Are Potential Age-Independent Markers of Prostate Cancer in Human Expressed Prostatic Secretions; The Prostate; May 1, 2008; pp. 620-628; vol. 68, Issue 6; Wiley-Liss, Inc.; United States.

Schipper et al.; Polyamines and Prostatic Cancer; Biochemical Society Transactions; Apr. 1, 2003; pp. 375-380; vol. 31, Issue 2; Portland Press; United Kingdom.

Cheng et al.; Non-Destructive Quantitation of Spermine in Human Prostate Tissue Samples Using HRMAS 1H NMR Spectroscopy at 9.4 T; FEBS Letters; Apr. 6, 2001; pp. 112-116; vol. 494, Issue 1-2; Elsevier Science B.V.; Netherlands.

Hiramatsu et al.; Diagnostic and Prognostic Usefulness of N1, N8-Diacetylspermidine and N1, N12-Diacetylspermine in Urine as Novel Markers of Malignancy; Journal of Cancer Research and Clinical Oncology; Oct. 1997; pp. 539-545; vol. 123, Issue 10; Springer-Verlag; United States.

Li et al.; Macrophage Inhibitory Cytokine 1 Biomarker Serum Immunoassay in Combination with PSA Is a More Specific Diagnostic Tool for Detection of Prostate Cancer; PLOS One; Apr. 8, 2015; vol. 10, Issue 4; Public Library of Science; United States.

Ferro et al.; Prostate Health Index (Phi) and Prostate Cancer Antigen 3 (PCA3) Significantly Improve Prostate Cancer Detection at Initial Biopsy in a Total PSA Range of 2-10 ng/ml; PLOS One; Jul. 4, 2013; vol. 8, Issue 7; Public Library of Science; United States.

International Search Report and Written Opinion of PCT application No. PCT/CN2017/106589 issued from the International Search Authority dated Jan. 17, 2018.

Kadjane et al.; Improving Visible Light Sensitization of Luminescent Europium Complexes; Journal of Fluorescence; Oct 2, 2007; pp. 119-129; vol. 18, Issue 1; Springer.

Fletcher et. al.; Spermine Detection via Metal-mediated Ethynylarene 'Turn-on' Fluorescence Signaling; Sensors and Actuators B: Chemical; Nov. 1, 2014; vol. 207, Part A; pp. 843-848; Elsevier.

Chow et. al.; Design and Synthesis of Heterobimetallic Ru(II)-Ln(III) Complexes as Chemodosimetric Ensembles for the Detection of Biogenic Amine Odorants; Analytical Chemistry; Jul. 25, 2013; vol. 85, Issue 17; pp. 8246-8253; ACS Publications.

Liu et. al.; Highly Selective Colorimetric Detection of Spermine in Biosamples on Basis of the Non-crosslinking Aggregation of ssDNA-capped Gold Nanoparticles; Nov. 9, 2012; Talanta; vol. 106; pp. 255-260; Elsevier.

Martinez et.al.; Sensitive and Selective Plasmonic Assay for Spermine as Biomarker in Human Urine; Analytical Chemistry; Jan. 15, 2014; vol. 86, Issue 3; pp. 1347-1351; ACS Publications.

Kim et. al.; A Gold Nanoparticle-Based Fluorescence Turn-On Probe for Highly Sensitive Detection of Polyamines; Sep. 16, 2011; Chemistry: A European Journal; vol. 17, Issue 43; pp. 11978-11982; Wiley.

Tsoi et. al.; Urinary Polyamines: A Pilot Study on Their Roles as Prostate Cancer Detection Biomarkers; Sep. 6, 2016; PLOS ONE; vol. 11, No. 9; pp. 1-13; Public Library of Science.

Zhang et. al.; Surface Science of DNA Adsorption onto Citrate-Capped Gold Nanoparticles; Langmuir; Jan. 24, 2012; vol. 28, Issue 8; pp. 3896-3902; ACS Publications.

First Examination Report with Search Report of TW App. No. 107112944 issued by the Taiwan Intellectual Property Office (TIPO) of the ROC dated Jun. 4, 2019.

Tsoi et al.; Urinary Polyamines: A Pilot Study on Their Roles as Prostate Cancer Detection Biomarkers; PLOS ONE; Sep. 6, 2016; DOI:10.1371/journal.pone.0162217.

Abergel et al.; Using the Antenna Effect as a Spectroscopic Tool: Photophysics and Solution Thermodynamics of the Model Luminescent Hydroxypyridonate Complex [EuIII(3,4,3-LI(1,2-HOPO))]-; Inorganic Chemistry; Dec. 7, 2009; vol. 48, Issue 23; ACS Publications.

* cited by examiner

| Sample No. | Conc/ppm | Sample No. | Conc/ppm |
|---|---|---|---|
| 1 | 4.14 | 6 | 0.38 |
| 2 | 1.97 | 7 | 0.36 |
| 3 | 0.63 | 8 | 0.31 |
| 4 | 0.66 | 9 | 2.04 |
| 5 | 0.37 | 10 | 1.14 |

Figure 9B

URINARY POLYAMINES AS PROSTATE CANCER DETECTION BIOMARKERS

CROSS-REFERENCE TO RELATED APPLICATIONS

This application claims priority from U.S. Provisional Patent Application Ser. No. 62/409,361 filed on Oct. 17, 2016, and U.S. Provisional Patent Application Ser. No. 62/471,989 filed on Mar. 16, 2017 the disclosure of which is hereby incorporated by reference.

FIELD OF THE INVENTION

The present disclosure relates to methods for the detection and quantization of urinary polyamines and compositions for use therein. The methods and compositions described herein are useful in diagnosis of prostate cancer in patient.

BACKGROUND OF THE INVENTION

Prostate cancer (PCa) is the second most common cancer in men, and is one of the leading causes of mortality and results in momentous public health impact in many developed countries, including many Western European nations and the United States.

PCa is a disease of increasing significance worldwide. No exception is Hong Kong in this public health issue. With reference to the statistics of Hong Kong Cancer Registry, Hospital Authority, HKSAR, PCa ranked $3^{rd}$ for the most common cancers in men and $5^{th}$ for the most fatal cancers. Given the latency of early, treatable PCa and the lethality of its late and discernible stage, there is an urgent need for more sensitive and accurate diagnostic methods to detect early stage PCa, so that treatment outcome can be significantly improved with more lives being saved.

Current diagnosis of PCa relies on digital rectal examination (DRE) and serum prostate specific antigen (PSA) test, followed by transrectal ultrasound prostatic biopsy (TRUSPB) confirmation. Although DRE is a simple procedure, it causes discomfort to patients. DRE is also a strong-investigator-dependent technique, which results in poor accuracy for PCa diagnosis. In particular, DRE is not a good tool for the early detection of PCa, because most DRE positive PCa results are of advanced staging. Although the PSA test shows good sensitivity in detecting early stage PCa, elevated PSA levels have also been observed in patients with benign prostatic hyperplasia (BPH) and prostatitis, etc., which decreases the specificity of PSA for PCa.

Within the grey zone of the PSA test, the positive-predictive value has a small mean value of 21%. A wide variety of PSA methodologies, such as the PSA density of transition zone, free/total PSA ratio, p2PSA and Prostate Health Index have been developed to improve the performance of PSA measurement.

Transrectal ultrasonography guided prostate biopsy (TRUSPB) is currently the most common diagnostic approach for histological confirmation of PCa diasnosis. However, this procedure is very labor intensive and leads to significant discomfort and complications to patients.

As a result of the poor specificity of serum PSA test, many patients without PCa are subjected to TRUSPB and thus its potential complications. It is therefore essential to develop a more efficient detection kit for accurate, early stage PCa screening.

It is an objective of the present disclosure to provide a method for diagnosing PCa in a patient comprising detecting one or more urinary polyamines (such as, putrescine (Put), spermindine (Spd) and/or spermine (Spm)). The urinary polyamines are useful as biomarkers for PCa detection. The diagnostic power of the urinary polyamines was identified by comparing urinary polyamine concentrations in patients diagnosed with PCa, patients diagnosed with benign prostatic hyperplasia (BPH) and healthy controls (HC). Also provided herein are compositions and methods useful for detecting and quantifying the amount of the urinary polyamines in a patient.

SUMMARY OF THE INVENTION

Accordingly, the objective of this disclosure is to develop a novel, highly-sensitive and specific, and colour-changing polyamines tracer with the use of lanthanide complexes or AuNPs, and to examine the averaged urinary concentrations of polyamines from patients of different age groups and stages of prostate cancer to validate polyamines as a trustworthy biomarkers for early prostate cancer screening.

In a first aspect of the present disclosure there is provided is a compound of formula (1):

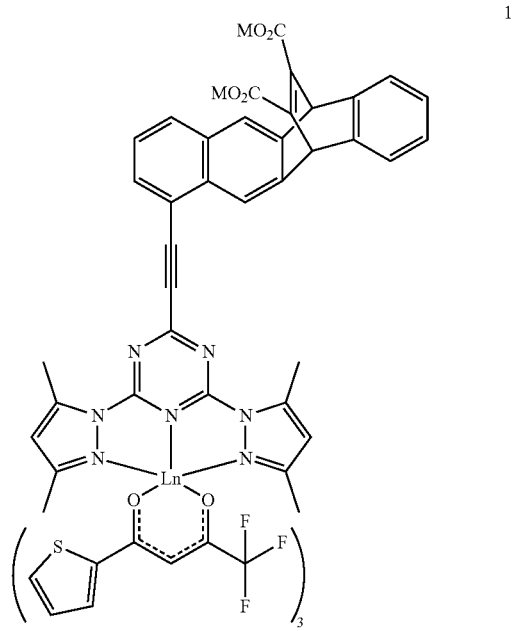

wherein,
Ln is a lanthanide metal; and
each M is independently selected from the group consisting of Na, Li, and K; or two M taken together represent Mg or Ca.

In a first embodiment of the first aspect of the present disclosure there is provided a compound of formula (1), wherein the lanthanide is europium.

In a second embodiment of the first aspect of the present disclosure there is provided a compound of formula (1), wherein M is Li.

In a second aspect of the present disclosure there is provided is a method of detecting one or more urinary polyamines, comprising the steps of:
a. providing a urine sample;
b. contacting the urine sample with a compound of formula (1) thereby forming a test sample; and c. detecting the presence of the one or more urinary polyamines in the test sample.

In a first embodiment of the second aspect of the present disclosure there is provided a method, wherein the urine sample is obtained from a human.

In a second embodiment of the second aspect of the present disclosure there is provided a method, wherein the urine sample is obtained from a human and the concentration of the one or more urinary polyamines is used to determine whether the human suffers from prostate cancer.

In a third aspect of the present disclosure there is provided is a method of detecting one or more urinary polyamines, comprising the steps of:
d. providing a urine sample;
e. contacting the urine sample with a nanoparticle comprising a gold nanoparticle and at least two ligands comprising citrate and single stranded DNA, wherein the molar ratio of single stranded DNA to gold nanoparticle is about 4:1 to about 3:1, thereby forming a test sample;
f. detecting the presence of the one or more urinary polyamines in the test sample.

In a first embodiment of the third aspect of the present disclosure there is provided a method, wherein the molar ratio of the single stranded DNA to the gold nanoparticle is between about 3.2:1 to about 3.0:1.

In a second embodiment of the third aspect of the present disclosure there is provided a method, wherein the molar ratio of the single stranded DNA to the gold nanoparticle is between about 3.2:1 to about 3.0:1 and the average diameter of the nanoparticle is about 1 nm to about 100 nm.

In a third embodiment of the third aspect of the present disclosure there is provided a method, wherein the molar ratio of the single stranded DNA to the gold nanoparticle is between about 3.2:1 to about 3.0:1 and the average diameter of the nanoparticle is about 2 nm to about 10 nm.

In a fourth embodiment of the third aspect of the present disclosure there is provided a method, wherein the single stranded DNA has between about 5 and about 50 nucleotides.

In a fifth embodiment of the third aspect of the present disclosure there is provided a method, wherein the urine sample has been subjected to a purification step prior to the step of contacting the urine sample with a nanoparticle to remove protein or salts.

In a six embodiment of the third aspect of the present disclosure there is provided a method, wherein the pH of the test sample in the step of detecting the presence of the one or more urinary polyamines is between about to 2 to about 8.

In a seventh embodiment of the third aspect of the present disclosure there is provided a method, wherein the step of detecting the presence of the one or more urinary polyamines further comprises determining the concentration of the one or more urinary polyamines.

In an eighth embodiment of the third aspect of the present disclosure there is provided a method, wherein the step of detecting the presence of the one or more urinary polyamines further comprises determining the concentration of the one or more urinary polyamines and the step of determining the concentration comprises visual comparison of the color of the test sample with a reference color chart or a spectroscopic method.

In a ninth embodiment of the third aspect of the present disclosure there is provided a method, wherein the urine sample is obtained from a human.

In a tenth embodiment of the third aspect of the present disclosure there is provided a method, wherein the concentration of the one or more urinary polyamines is used to determine whether the human suffers from prostate cancer.

In an eleventh embodiment of the third aspect of the present disclosure there is provided a method, wherein the concentration of the single stranded DNA is about 200 nM to about 300 nM and the concentration of the gold nanoparticle is about 50 nM to about 100 nM in the test sample.

In a twelfth embodiment of the third aspect of the present disclosure there is provided a method, wherein the concentration of the single stranded DNA is about 240 nM to about 260 nM and the concentration of the gold nanoparticle is about 75 nM to about 87 nM in the test sample.

In a fourth aspect of the present disclosure there is provided is a kit comprising a nanoparticle, wherein the nanoparticle comprises a gold nanoparticle and at least two ligands comprising citrate and single stranded DNA, wherein the molar ratio of single stranded DNA to gold nanoparticle is between is about 4:1 to about 3:1 and instructions for carrying out the method of the third aspect.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF THE DRAWINGS

The above and other objects and features of the present disclosure will become apparent from the following description of the various embodiments described herein, when taken in conjunction with the accompanying drawings, in which:

FIG. 9B shows the concentration of Spm level in 10 selected prostate cancer patients' urine samples for UV test.

```
12mer:
CGA CAA CCA CAA;

24mer:
CGA CAA CCA CAA CAC ACA ATC TGA;

36mer:
CGA CAA CCA CAA CAC ACA ATC TGA CGA CAA CCA CAA)
```

Figure 17:
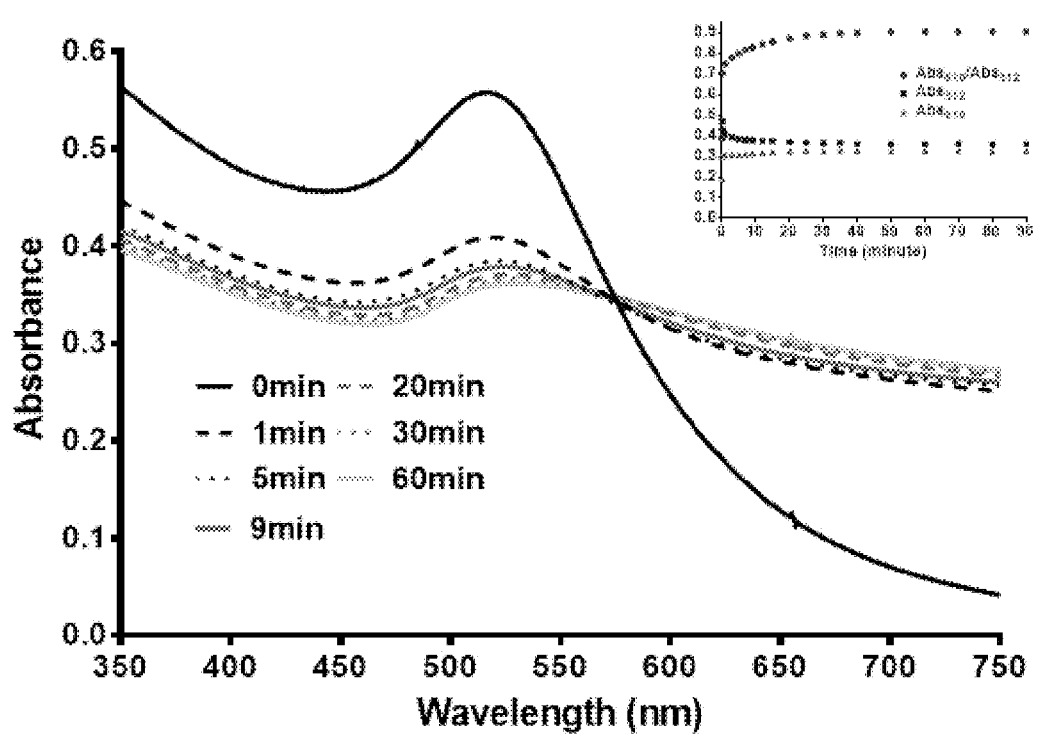

FIG. 17 shows the kinetics for Spm induced aggregation of DNA-AuNPs. (AuNPs: 80 nM; DNA: 25 nM; Spm: 6 μM) Inset: $Abs_{610}$, $Abs_{512}$ & their ratio against time.

Figure 18A:
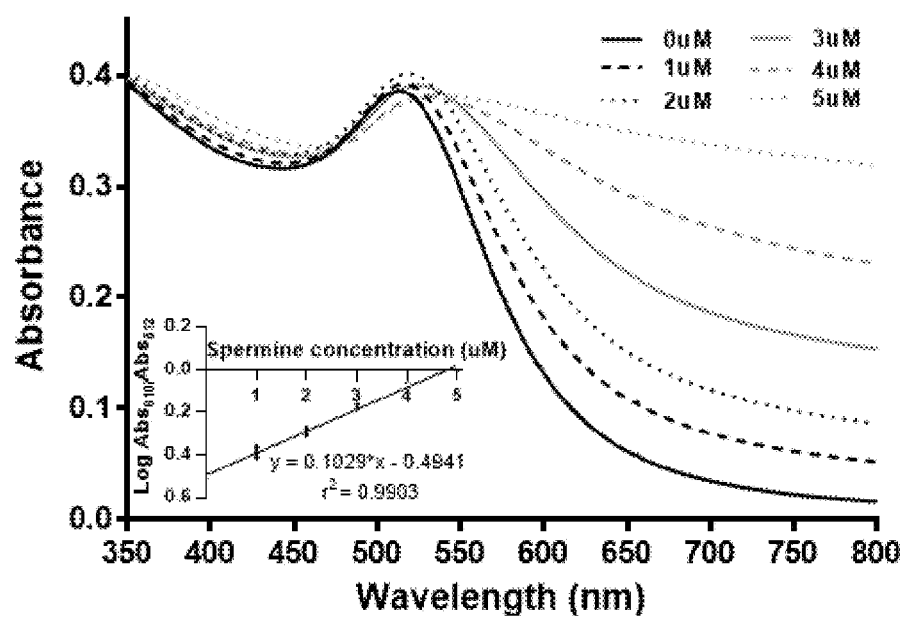

FIG. 18A shows Absorption spectra showing Spm induced aggregation on DNA capped AuNPs in blank matrix. Inset: Plot of normalized $Abs_{610}/Abs_{512}$ vs Spm concentration.

Figure 18B:
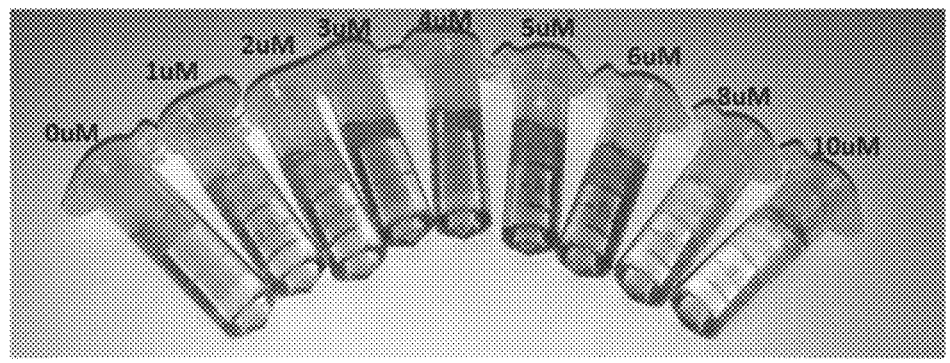

FIG. 18B shows the effect of Spm on visual color of AuNPs solution.

Figure 19:
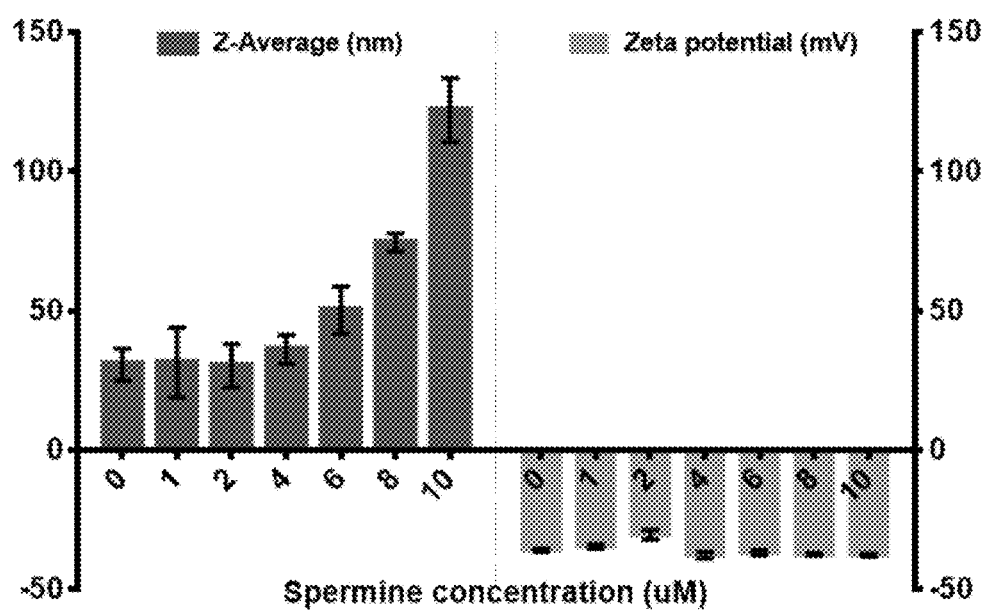

FIG. 19 shows DLS and zeta-potential measurements showing Spm induced aggregation of DNA-AuNPs.

Figure 20:
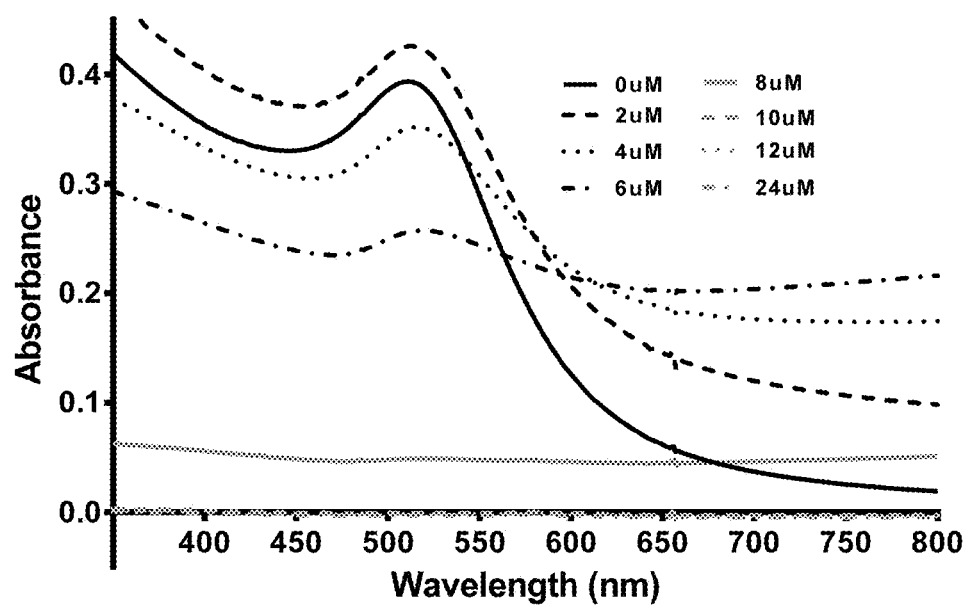

FIG. 20 shows the absorption spectrum showing Spm induced aggregation in the absence of DNA.

Figure 21A:
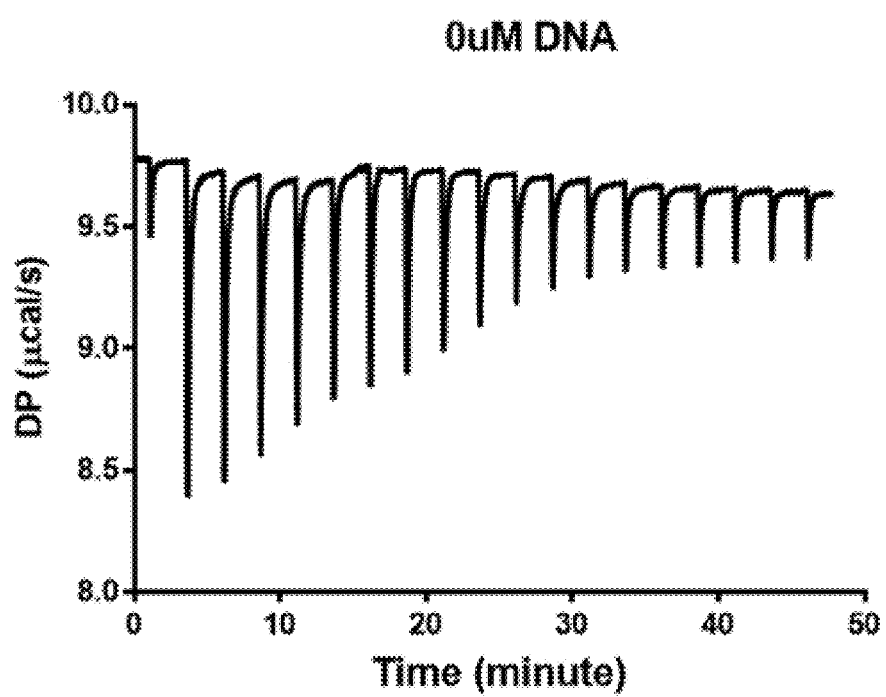

FIG. 21A shows heat flow of each injection as a function of time at 0 μM DNA concentration.

Figure 21B:
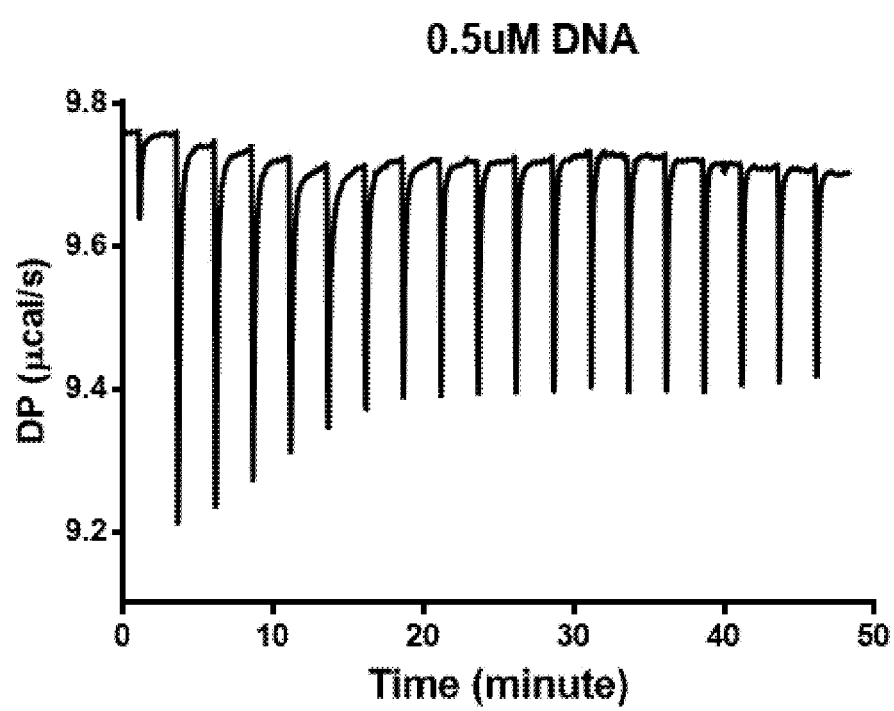

FIG. 21B shows heat flow of each injection as a function of time at 0.5 μM DNA concentration.

Figure 21C:
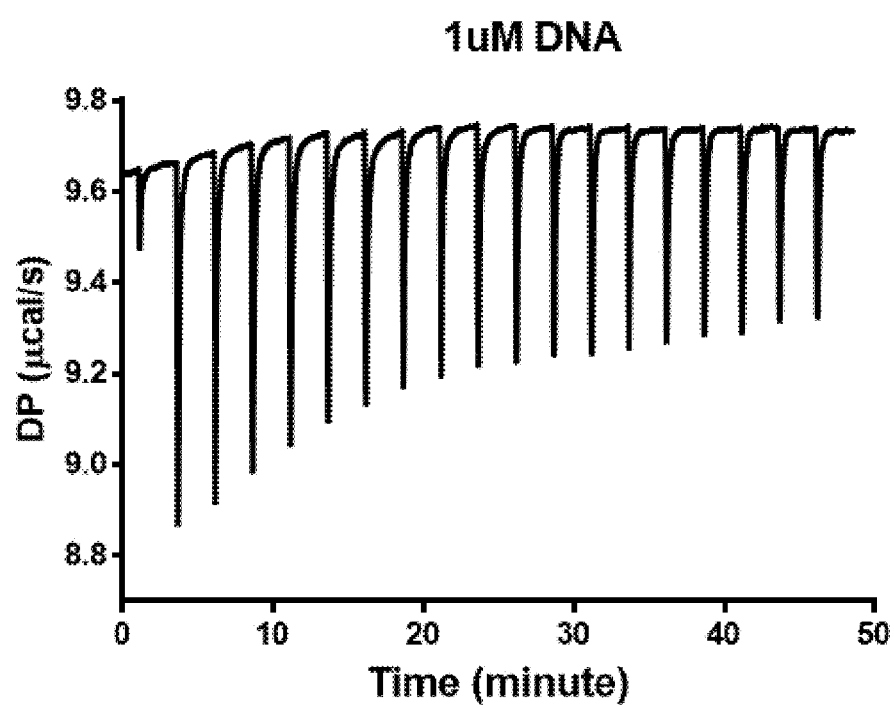

FIG. 21C shows heat flow of each injection as a function of time at 1 μM DNA concentration.

Figure 21D:
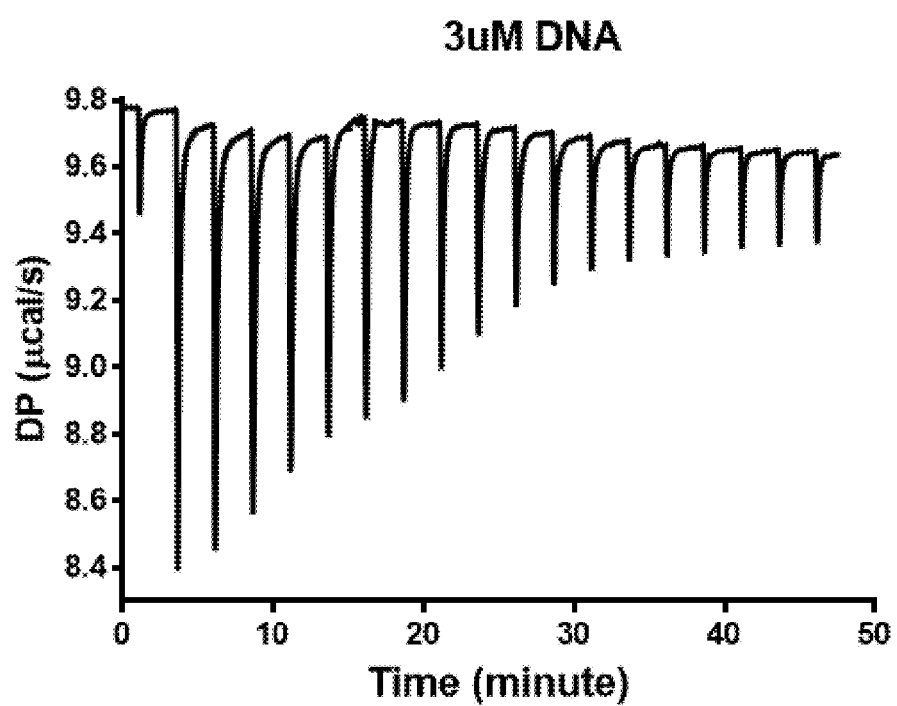

FIG. 21D shows heat flow of each injection as a function of time at 3 μM DNA concentration.

Figure 21E:
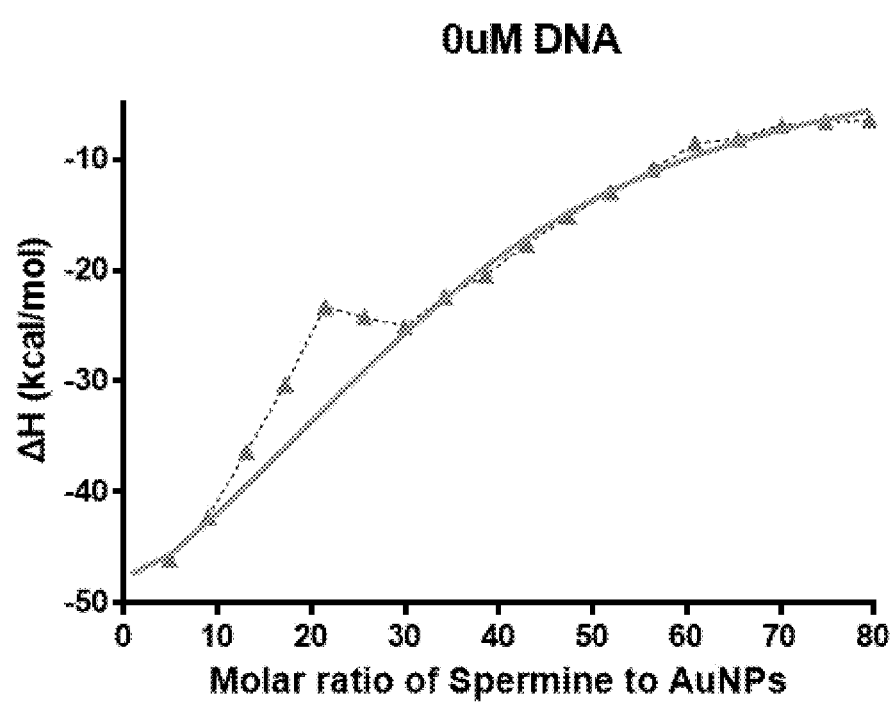

FIG. 21E shows the integration of each peak as a function of molar ratio of Spm to AuNPs at 0 μM DNA concentration.

Figure 21F:
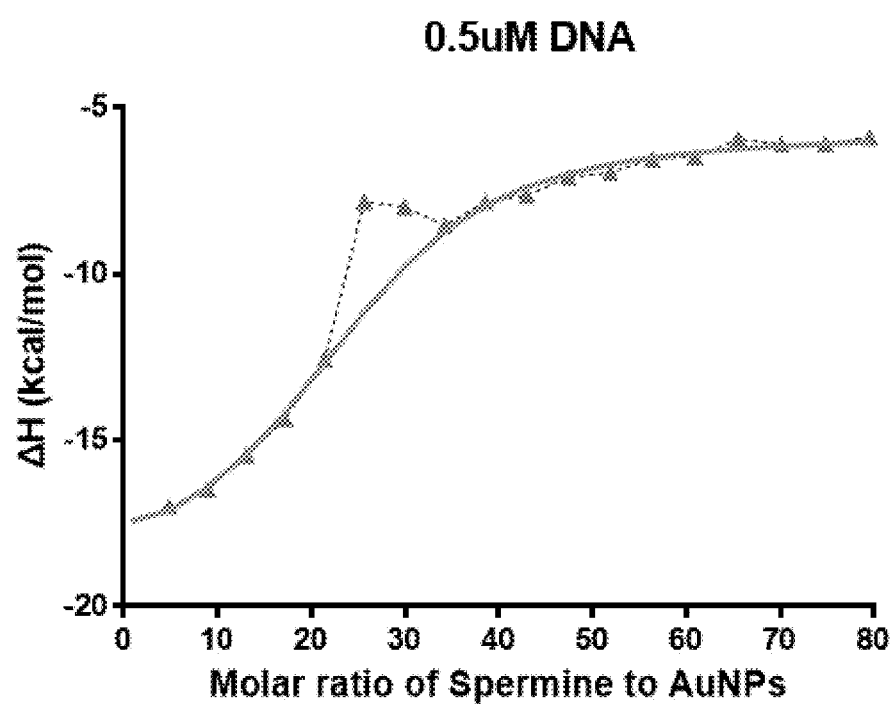

FIG. 21F shows the integration of each peak as a function of molar ratio of Spm to AuNPs at 0.5 μM DNA concentration.

Figure 21G:
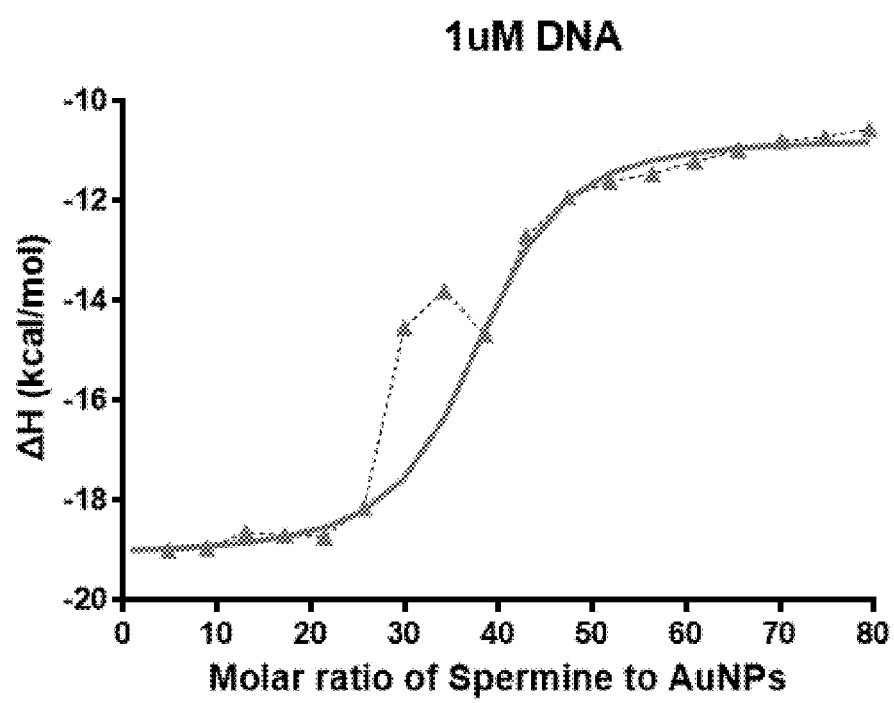

FIG. 21G shows the integration of each peak as a function of molar ratio of Spm to AuNPs at 1 μM DNA concentration.

Figure 21H:
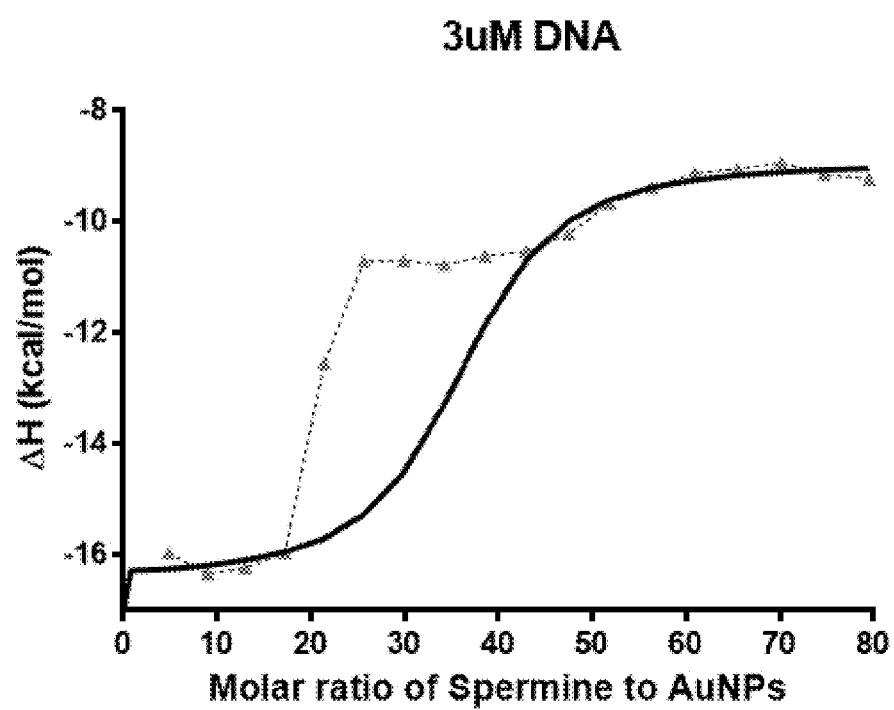

FIG. 21H shows the integration of each peak as a function of molar ratio of Spm to AuNPs at 3 μM DNA concentration.

Figure 22:
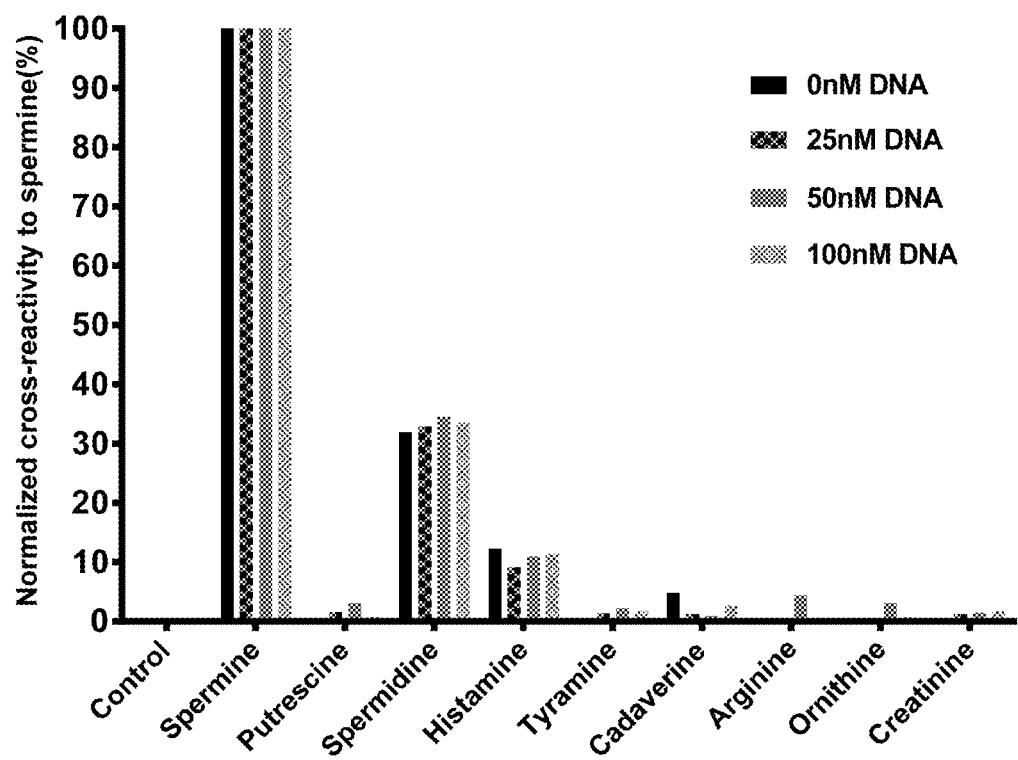

FIG. 22 shows the selectivity profile of current aptasensor at different DNA concentration. In each case control (only water) and Spm were normalized to 0 and 100% respectively.

Figure 23A:
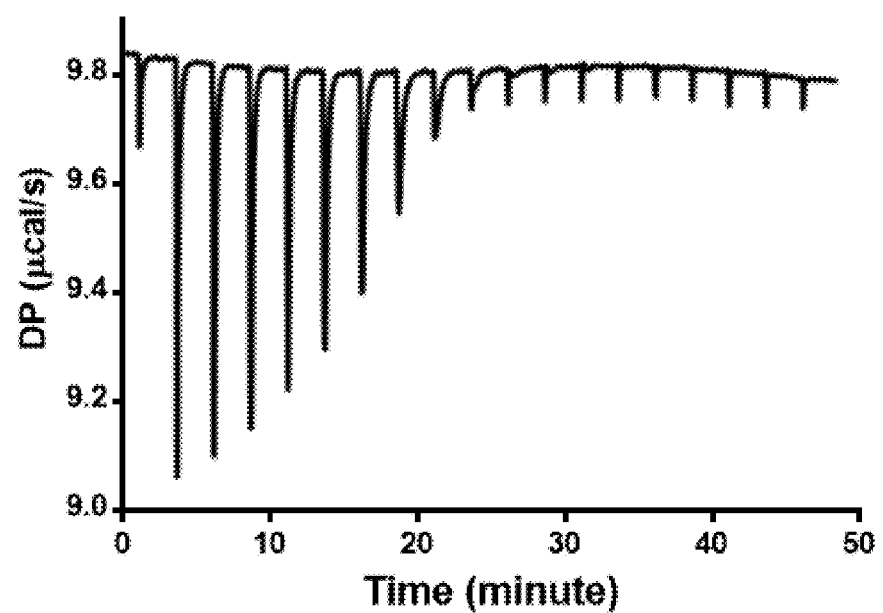

FIG. 23A shows the heat flow of each injection of Spm to DNA as a function of time.

Figure 23B:
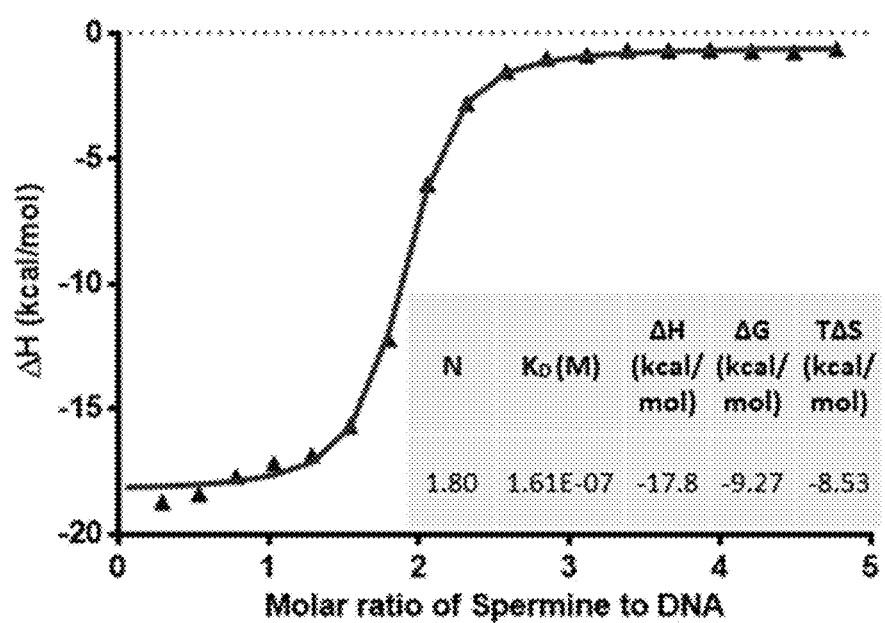

FIG. 23B shows the integration of each peak as a function of molar ratio of Spm to DNA. Inset: Thermodynamic parameters.

Figure 24:
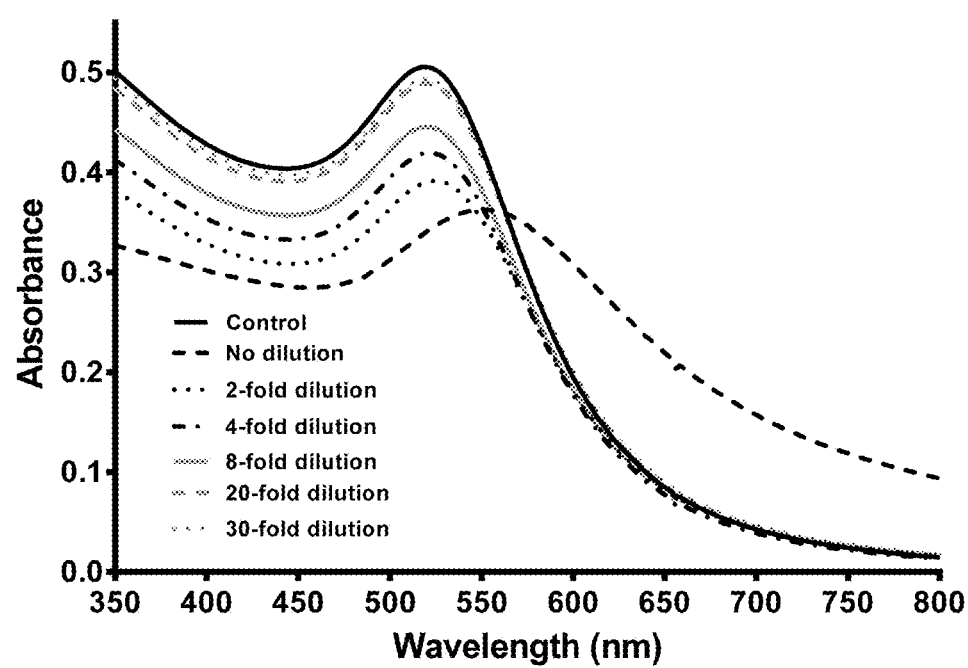

FIG. 24 shows the absorption spectra of DNA-AuNPs upon addition of artificial urine with different dilution factor.

Figure 25:
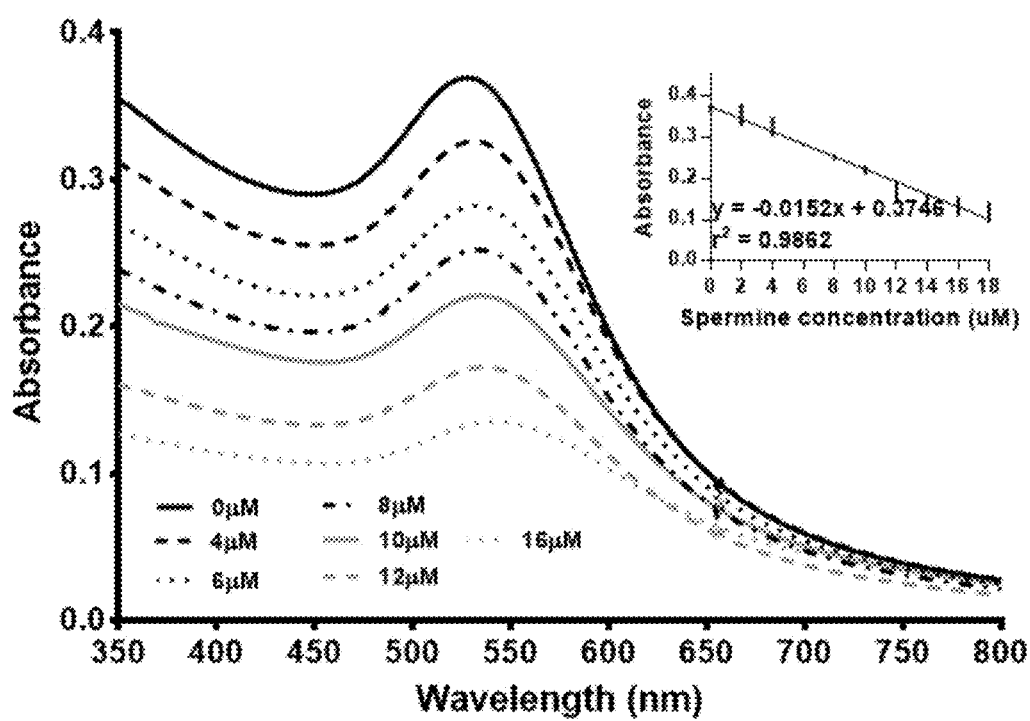

FIG. 25 shows the absorption spectra showing Spm induced aggregation on DNA capped AuNPs in artificial urine matrix. Inset: Plot of $Abs_{512}$ vs Spm concentration.

Figure 26:
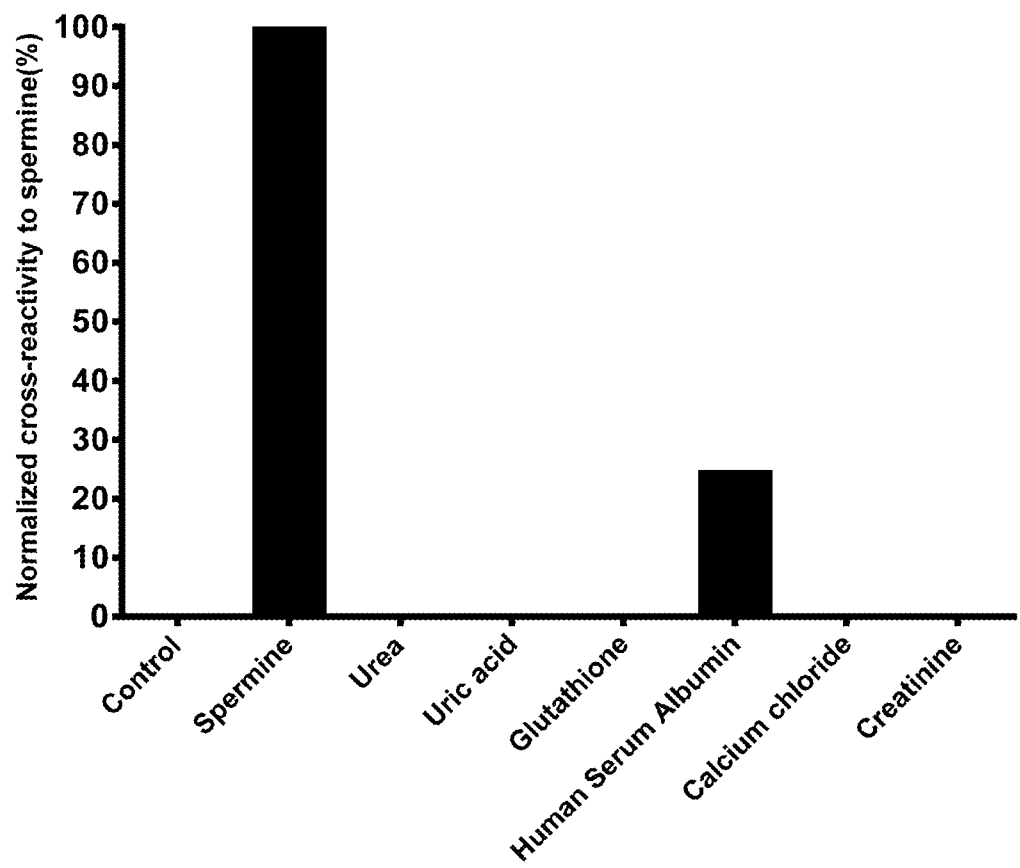

FIG. 26 shows the cross-reactivity of urinary components to Spm by developed aptasensor. In each case control (water) and Spm were normalized to 0 and 100% respectively. (Concentration used=4 μM)

Figure 27:
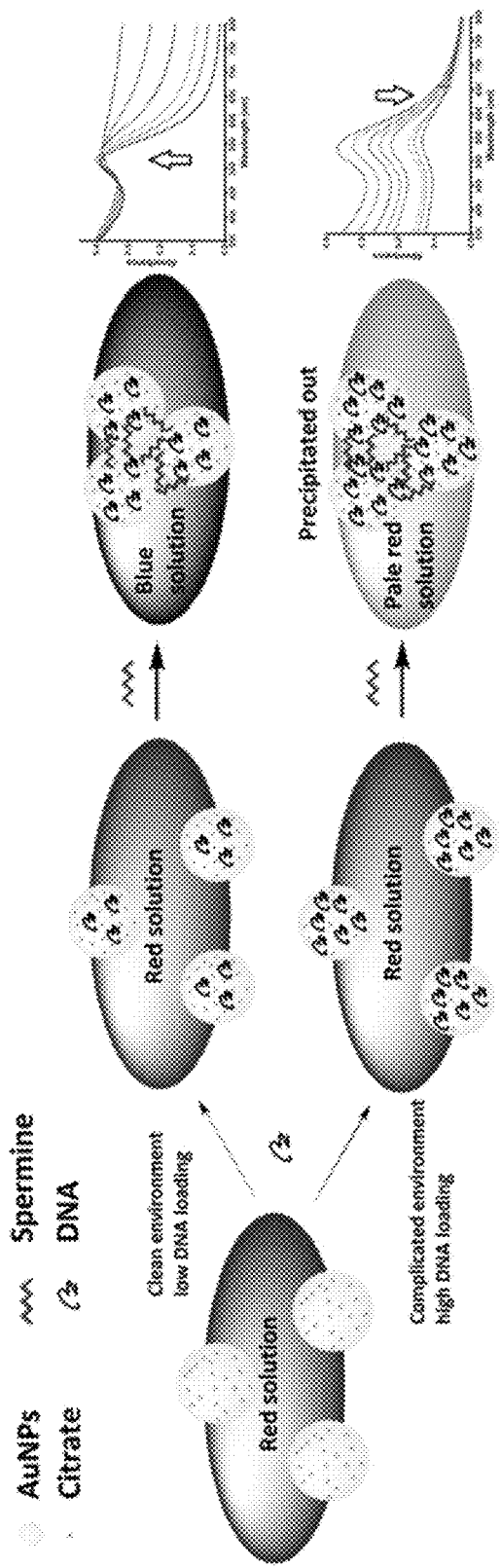

FIG. 27 shows the schematic diagram of the developed aptasensor for Spm sensing via two different pathways.

Figure 28A:
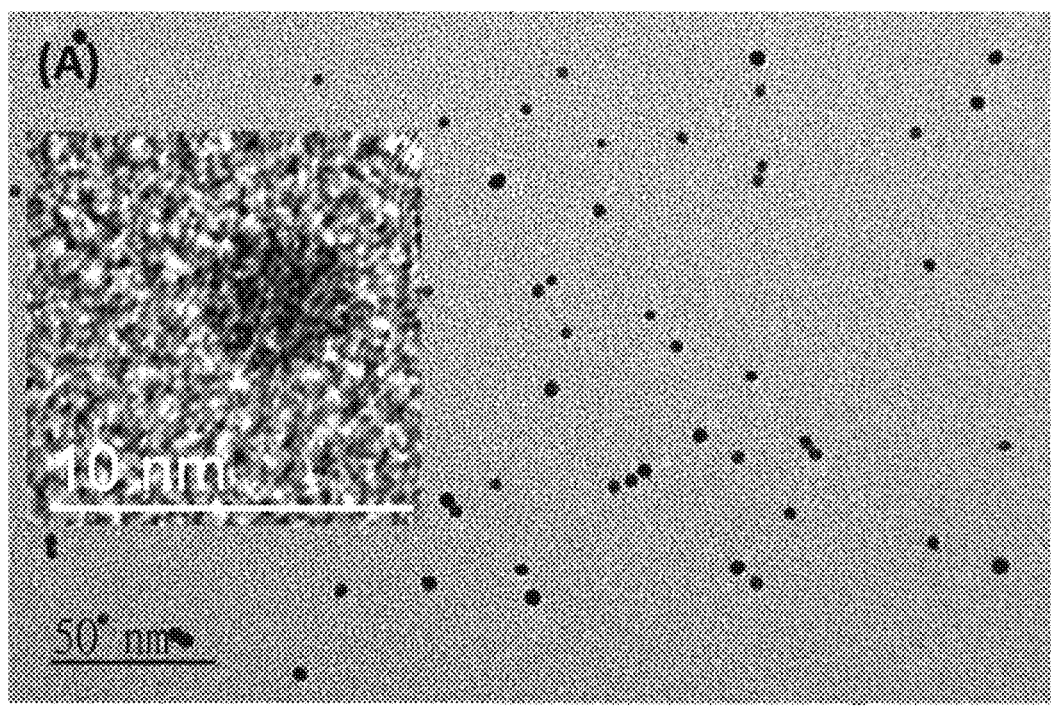

FIG. 28A shows the TEM images of citrate-AuNPs of size 4 nm. Inset: Magnified TEM image.

Figure 28B:
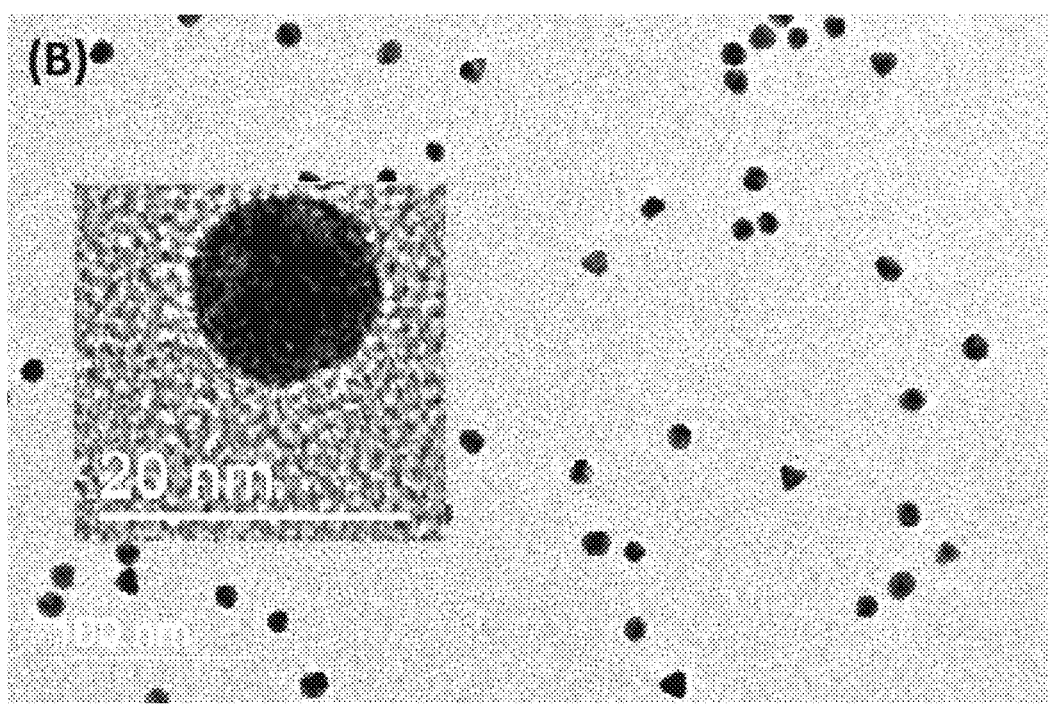

FIG. 28B shows the TEM images of citrate-AuNPs of size 13 nm. Inset: Magnified TEM image.

Figure 28C:
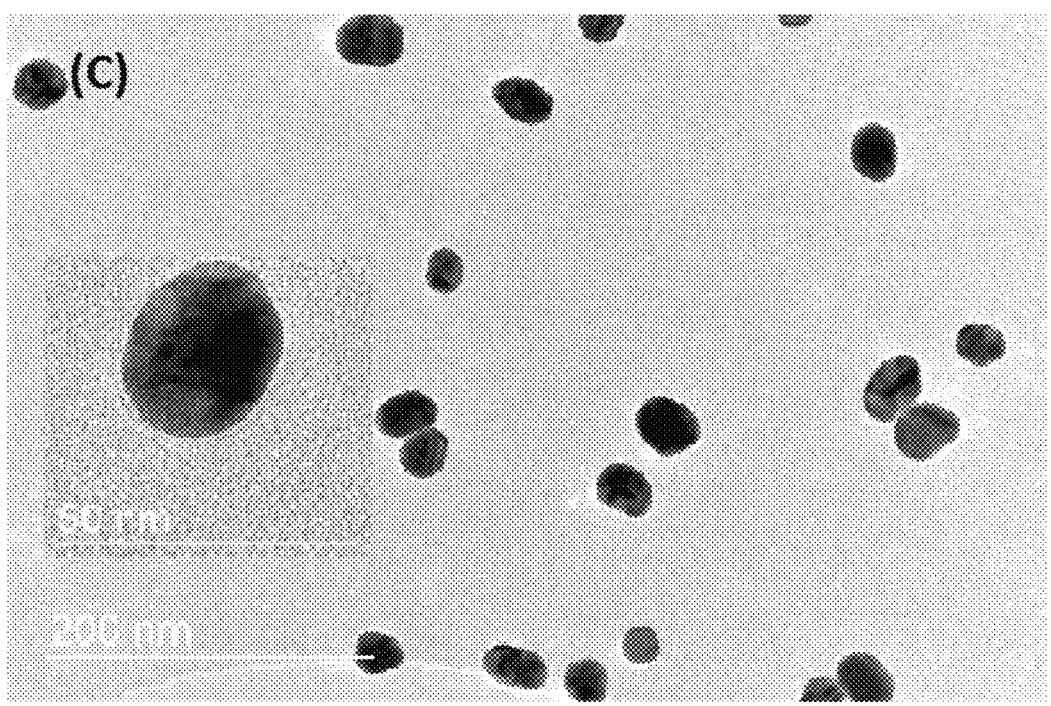

FIG. 28C shows the TEM images of citrate-AuNPs of size 27 nm. Inset: Magnified TEM image.

Figure 29:
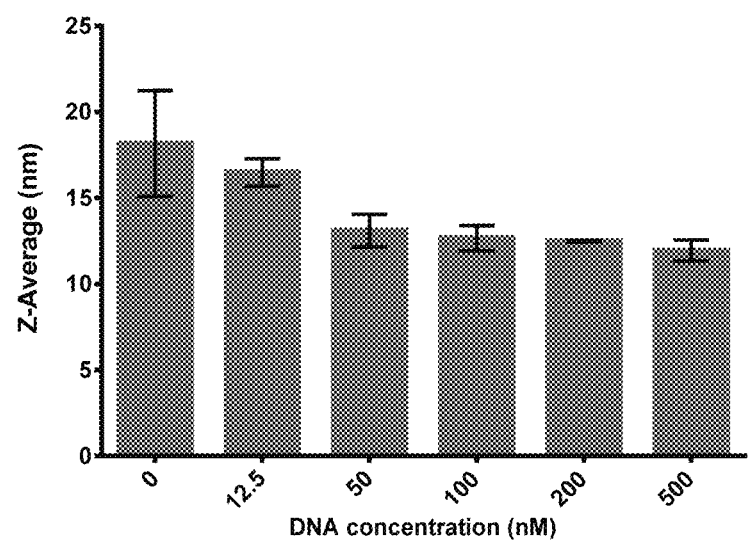

FIG. 29 shows DNA adsorption effect on DLS results of AuNPs. (AuNPs: 80 nM in 4 mM BR-buffer, pH=3.29)

Figure 30:
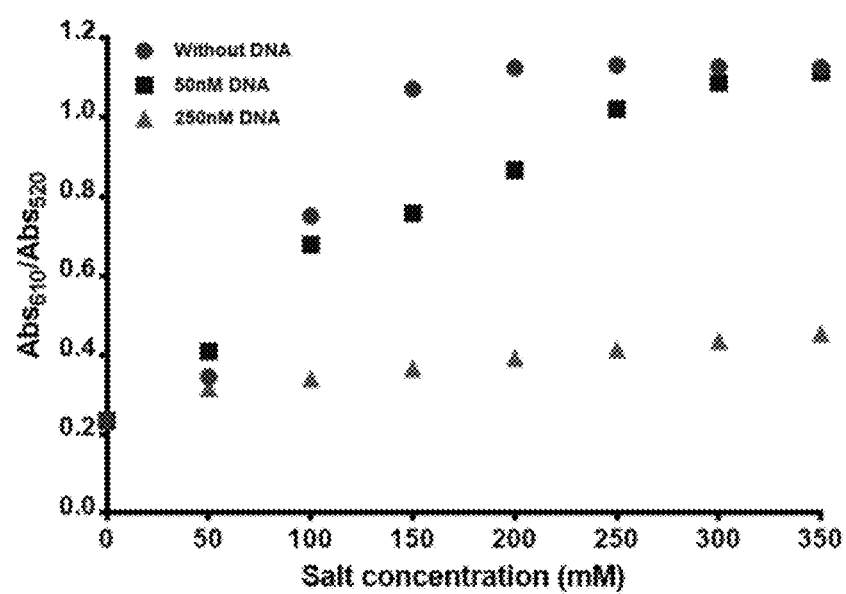

FIG. 30 shows DNA protection effect against 4 nm AuNPs aggregation at different NaCl concentration. (DNA concentration: 0, 50 and 250 nM)

Figure 31:
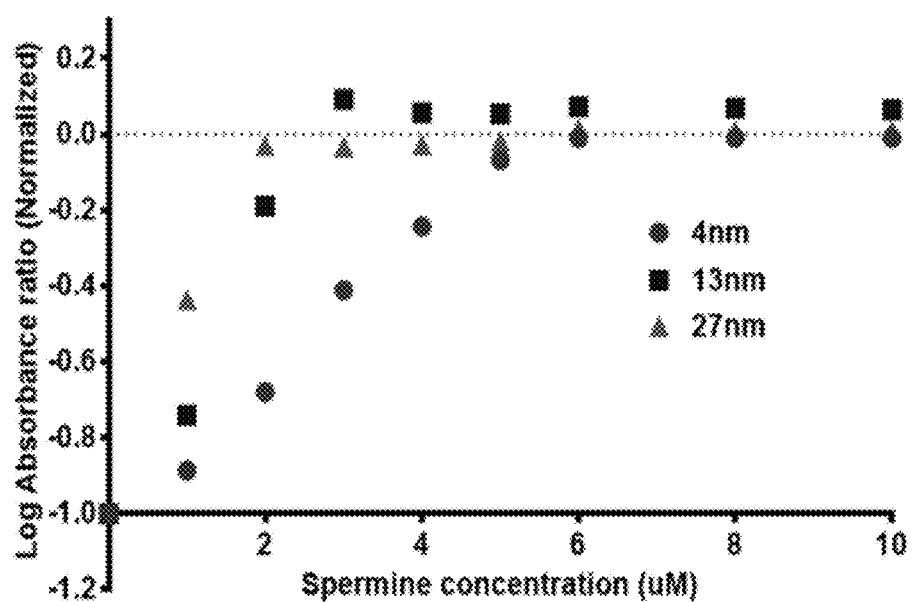

FIG. 31 shows the AuNPs size effect on calibration graph of Spm. (DNA concentration: 25 nM; pH=3.29; AuNPs concentration: 80 nM for 4 nm, 2.38 nM for 13 nm, 0.24 nM for 27 nm; concentration was chosen such that they gave similar absorbance value at their plasmonic peak; Plasmonic peak wavelength: 512 nm for 4 nm, 523 nm for 13 nm, 532 nm for 27 nm)

Figure 32A:
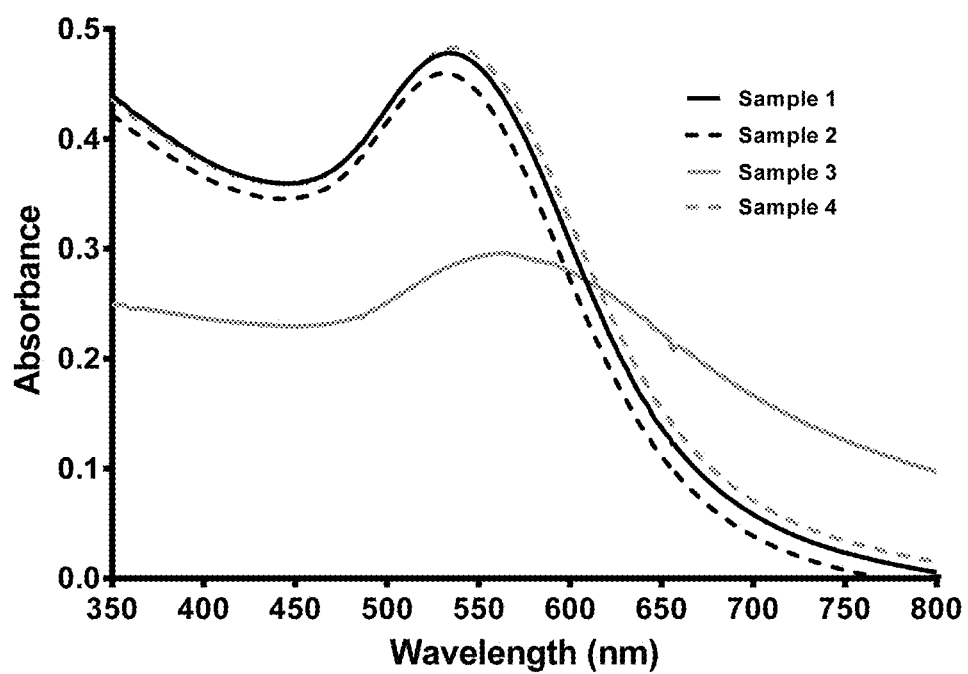

FIG. 32A shows Matrix effect of four urine samples before deproteinization.

Figure 32B:
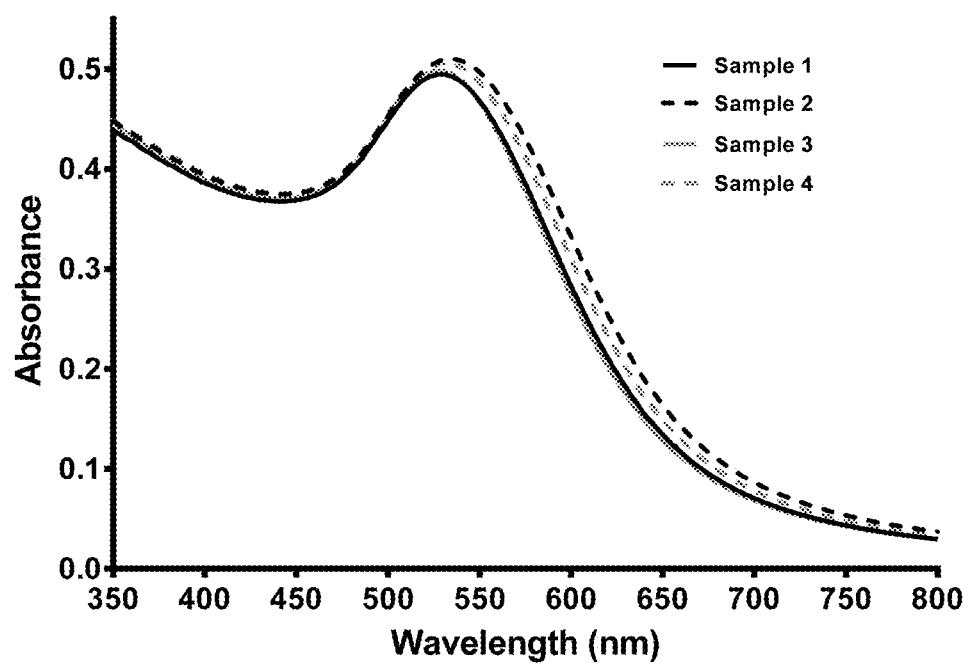

FIG. 32B shows Matrix effect of four urine samples after deproteinization.

Figure 32C:
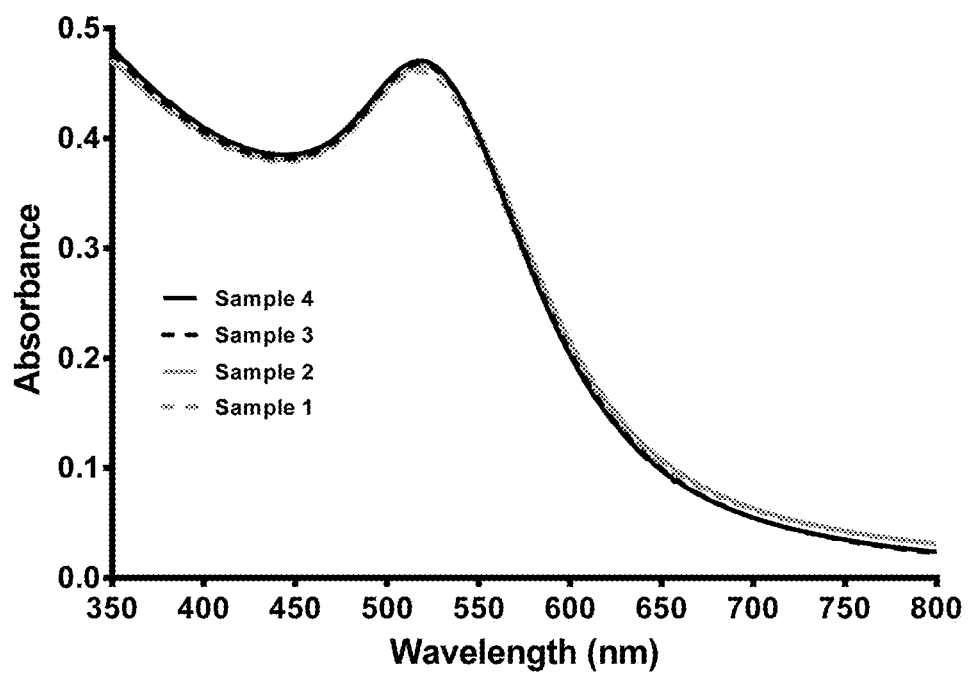

FIG. 32C shows Matrix effect of four urine samples after deproteinization and increasing DNA concentration to 100 nM.

Figure 33:
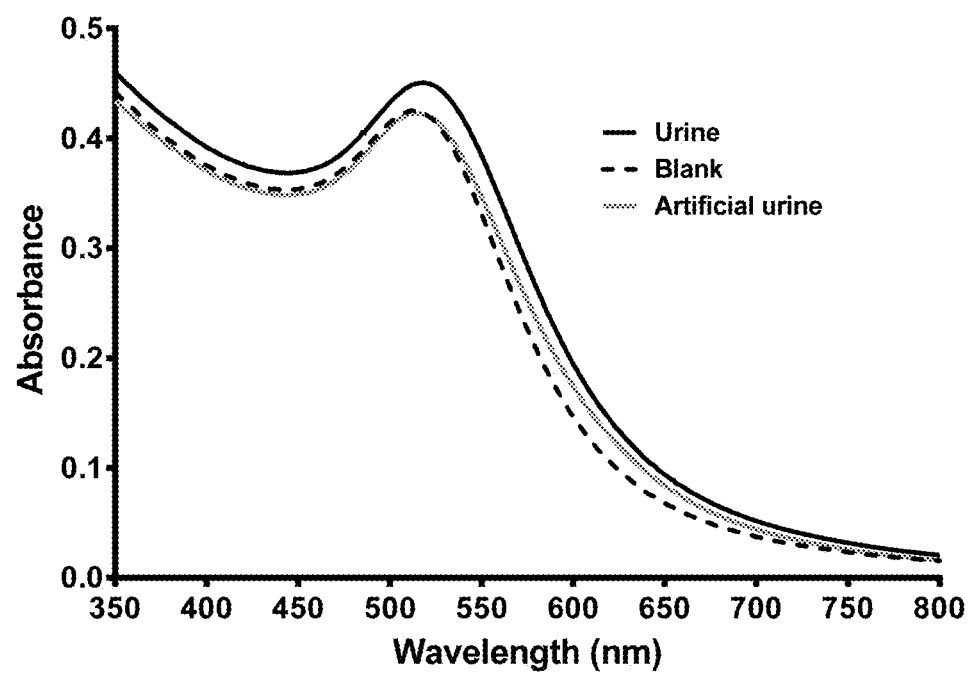

FIG. 33 shows the comparison of matrix effect of urine, blank ($H_2O$) and artificial urine.

DETAILED DESCRIPTION OF THE INVENTION

The present disclosure is not to be limited in scope by any of the specific embodiments described herein. The following embodiments are presented for exemplification only.

Three urinary polyamines (Put, Spd and Spm) were evaluated as biomarkers for PCa detection by comparing the concentrations of each in patients diagnosed with PCa, BPH patients and healthy patients. Through a well validated chromatographic method, urinary Spm had been shown to possess usefulness in differentiating PCa from non-cancerous disease states including BPH, and it could help to act as a secondary screening tool to serum PSA test to address its high false-positive rate when using 4.0 ng/ml as a cut-off point. Two kits were developed afterwards towards this novel biomarker and are described herein.

Part 1: Evaluation of Polyamines' Roles as PCa Biomarker
  Clinical Samples

Three subsets of patients for the clinical samples collection were assigned as follows: patients diagnosed with PCa, patients diagnosed with BPH, and HC. Written consent was acquired from all of the subjects. Enrolment of patients into the clinical study was reviewed and approved by the Clinical Research Ethical Committee of the Chinese University of Hong Kong, and the study was performed strictly according to the guidelines developed by that committee. Urine samples were obtained at noon time after lunch prior to prostatic biopsy from 165 male patients (age >50) having serum PSA level greater than 4.0 ng/ml between October 2014 and March 2016. These patients' urine samples were accepted only when they didn't have clinically active urinary tract infection which might pose a biasing effect. When patients did not agree to consent for the study, or they clinically showed evidence of other types of cancers, they were excluded from the sampling scheme.

Amongst these 165 patients, 66 were diagnosed as having PCa and the remaining 99 had no evidence of malignancy (NEM) by using TRUSPB as the reference standard. To further categorize these 99 NEM patients, using the criteria of prostate volume >30 ml as criteria, 88 were found to have BPH while others were considered as HC. All pathological examinations were conducted at Prince of Wales Hospital, The Chinese University of Hong Kong, Hong Kong under the supervision of experienced uro-pathologists.

Table 1 shows all the clinicopathologic characteristics of samples. All samples were stored at −20° C. until measurement. All measurements were conducted within three months after collection.

D, 95% CP) and heptafluorobutyric acid (HFBA, ≥99.0%) were purchased from Sigma-Aldrich (Hong Kong, China) and used without further purification. Strong Anion Exchange solid phase extraction (SPE) cartridges were obtained from Phenomenex (Strata, 100 mg/3 mL, USA). Centrifugation was performed using a Refrigerated centrifuge obtained from Eppendorf (5417R, Hong Kong, China).

Determination of Creatinine

The creatinine concentration inside urine samples were determined by LabAssay™ Creatinine assay (Wako, Japan). Briefly, urine samples and standards were thawed, deproteinized and centrifuged. The supernatant was separated and reacted with picric acid in alkaline solution to produce tangerine condensate through Jaffe reaction as reported in Bonsnes R W, Taussky H H. *On the colorimetric determination of creatinine by the Jaffé reaction. J Biol Chem.* 1945; 158(3):581-9. Quantitation of total creatinine inside samples was made by measurement of absorbance by a Clariostar Monochromator Microplate Reader (BMG Labtech, Hong Kong). Concentrated urine samples which exceeded the calibration points were diluted with water with appropriate dilution factor before sample preparation. Each sample was determined at least twice with Relative standard deviation (RSD) less than 15%.

TABLE 1

Clinicopathologic characteristics of patients.

| Characteristics | PCa (n = 66) | BPH (n = 88) | HC (n = 11) | p value (PCa vs BPH) | p value (PCa vs HC) | p value (BPH vs HC) |
|---|---|---|---|---|---|---|
| Age | | | | | | |
| Mean(SEM) | 69.6(0.8) | 66.9(0.6) | 64.9(1.1) | 0.018 | 0.027 | 0.245 |
| Median | 69 | 66 | 65 | | | |
| Range | 54-86 | 51-79 | 59-74 | | | |
| Preoperative PSA. ng/ml | | | | | | |
| Mean(SEM) | 46.39(8.61) | 12.39(1.57) | 26.54(7.51) | <0.0001 | 0.350 | 0.007 |
| Median | 15.60 | 8.60 | 8.50 | | | |
| Range | 4.20-299.00 | 4.40-98.50 | 4.3-66.00 | | | |
| Gleason score (GS) | | | | | | |
| 5 | 1 | | | | | |
| 6 | 26 | | | | | |
| 7 | 15 | | | | | |
| 8 | 10 | | | | | |
| 9 | 12 | | | | | |
| 10 | 2 | | | | | |
| Prostate volume (ml) | | | | | | |
| Mean(SEM) | 43.81(2.44) | 67.28(2.98) | 17.46(2.67) | <0.0001 | <0.0001 | <0.0001 |
| Median | 40.00 | 56.50 | 20.40 | | | |
| Range | 16.60-87.80 | 32.20-162.00 | 4.60-30.00 | | | |

Materials and Chemicals

Methanol was obtained from TEDIA (HPLC/Spectro grade, ≥99.9%). Acetonitrile was obtained from ACS (HPLC grade, ≥99.9%). Water was purified in a MilliQ Direct Water Purification System (Millipore, USA). All standard compounds, including 1,4-Diaminobutane (Put, 99%), spermidine (Spd, ≥99.0%), spermine (Spm, ≥99.0%), 1,4-Diamino(butane-$d_8$) dihydrochloride (98 atom % D), spermidine-(butane-$d_8$) trihydrochloride (98 atom % D, 95% CP), spermine-(butane-$d_8$) tetrahydrochloride (97 atom %

Standard Preparation for Determination of Polyamines

Stock solutions (5000 μg/ml) of each polyamine (Put, Spm, Spd) were prepared in water separately. The three stock solutions were mixed and diluted to give an intermediate standard (50 μg/ml), which was then used to prepare a series of working standards with polyamine concentrations of 10, 25, 50, 100, 250, 500, 1000 ng/ml in water. For internal standards, the stock solutions (5000 μg/ml) of each polyamine (Put-$d_8$, Spm-$d_8$, Spd-$d_8$) were prepared in water individually. The three stock solution were mixed and diluted to give an internal standard (IS) working solution (1 µg/ml) in water.

Sample/Standard Pretreatment for Determination of Polyamines

The sample preparation procedures followed the method developed by Häkkinen et al. *Analysis of free, mono-and diacetylated polyamines from human urine by LC-MS/MS. J Chromatogr B Analyt Technol Biomed Life Sci.* 2013; 941: 81-9 with little modifications. Firstly, urine samples/standards were thawed naturally and centrifuged for 5 minutes at 13000 rpm and room temperature. 120 µL of urine sample/standard supernatant and 60 µL of IS working solution were mixed with 420 of water. 550 µL of this well-mixed solution was passed through the SPE cartridges, which had been conditioned and equilibrated with 1 mL of methanol and water respectively. 450 µL of water was passed through the cartridge afterwards to elute out all polyamines. 400 µL of these SPE treated samples were then mixed with 100 µL of 10% HFBA, and the final mixture was ready for instrumental analysis. Concentrated urine samples which exceeded the calibration points were diluted with water with appropriate dilution factors before sample preparation.

Quality Control Samples for Determination of Polyamines

For each batch of sample analysis, three Quality control (QC) working solutions were analyzed to verify the accuracy of calibration curves and ensure comparability among batches. The solutions were prepared using analyzed control urine samples from our research group. The polyamines concentrations of controls' urine samples were determined and then mixed equally to give a pooled urine sample. Afterwards, three QC working solutions with different polyamine concentration range (low, medium and high) were prepared by mixing this pooled urine sample with standard solutions. For low polyamine concentration QC working solution, the SPE-treated pooled urine sample was mixed with SPE-treated 10 ng/ml standard in the 1:7 ratio. For medium polyamine concentration QC working solution, the SPE-treated pooled urine samples were mixed with SPE-treated 100 ng/ml standard in the 1:1 ratio. For high polyamine concentration QC working solution, the SPE-treated pooled urine sample was mixed with SPE-treated 1000 ng/ml standard in the 1:1 ratio.

Stability Studies

For stability study, Häkkinen et al. had previously demonstrated that both the standard mixtures and QC samples were stable after storing at six hours at room temperature (short-term stability), after storage at −20° C. and −80° C. respectively for two months (long-term stability) and after going three cycles of freezing and thawing before sample preparation (freeze thaw stability). For further verification, the content of polyamines and creatinine inside both standards and selected urine samples was analyzed. It was found that, upon five cycles of freeze and thaw, all the contents were still stable in six months' time when storing at −20° C. For the SPE-treated samples, it was stable for at least two days when storing at 4° C. and up to a year when storing at −20° C.

Instrumentation and Statistical Analysis

The quantitation of polyamines was performed by Ultra-high Performance Liquid Chromatography coupled with a triple quadrupole mass spectrometer (UPLC-MS/MS). LC separation was done by an Agilent 1290 Infinity Quaternary LC System while mass analyzing was done by an Agilent 6460 Triple Quadrupole mass spectrometer equipped with an Agilent Jet Stream technology electrospray ionization source. The column used was an Agilent EclipsePlus C18 RRHD (2.1×50 mm, 1.8 µm) protected with an Agilent SB-C18 guard column (2.1×5 mm, 1.8 µm).

The LC elution profiles were optimized as follows: Eluent A was water with 0.1% HFBA while eluent B was acetonitrile with 0.1% HFBA. Eluent A was decreased from 95% to 60% in 10 minutes. The gradient was then decreased from 60% to 10% of eluent A in 1 minute. Afterwards the gradient was held constant for 5 minutes. The gradient was then increased from 10% to 95% in 1 minute, followed by being held constant for 8 minutes. (Total run-time=25 minutes).

Autosampler and column temperature were set as 4° C. and 35° C. respectively. Injection was achieved by 5-second needle wash in Flush Port mode for 3 times with eluent B. In each time 10 µL was injected.

For the source parameter, drying gas (nitrogen) temperature was set as 300° C. with 5 l/min flow rate. Nebulizer pressure was 45 psi. Sheath gas temperature was set as 250° C. with 11 l/min flow rate. Capillary voltage was set as 3500V. For mass detection, scheduled multiple reaction monitoring (MRM) was performed. The information of MRM transitions can be found in Table 2.

TABLE 2

MRM transitions, dwell time, fragmentor, collision energy and cell accelerator voltage for Put, Spm, Spd and their corresponding internal standards

| | Precusor ion | Daughter ion | Dwell time (ms) | Fragmentor (V) | Collision energy (V) | Cell Accelerator Voltage (V) |
|---|---|---|---|---|---|---|
| Putrescine | 89 | 72* | 100 | 70 | 6 | 3 |
| Putrescine-$d_8$ | 97 | 80* | 100 | 70 | 6 | 3 |
| Spermidine | 146 | 112 | 100 | 90 | 10 | 3 |
| | 146 | 72* | 100 | 90 | 15 | 3 |
| Spermidine-$d_8$ | 154 | 120 | 100 | 90 | 10 | 3 |
| | 154 | 80* | 100 | 90 | 15 | 3 |
| Spermine | 203 | 129 | 100 | 90 | 10 | 3 |
| | 203 | 112* | 100 | 90 | 15 | 3 |
| Spermine-$d_8$ | 211 | 137 | 100 | 90 | 10 | 3 |
| | 211 | 120* | 100 | 90 | 15 | 3 |

*Denoted the quantifier transitions

The result was calculated using Agilent MassHunter Workstation software. Calibration curves were fitted linearly without any weighing. The correlation coefficients should not be smaller than 0.995. Acceptance values for each calibration points and quality control working solutions were ±30% to ensure accuracy. For precision verification, after every 10-sample injection each time, a 250 ng/ml standard was injected and checked if it can be reproduced (±15%).

For statistical analysis, the receiver operating characteristics (ROC) curve and the area under curve (AUC) were obtained by using GraphPad Prism 6 (GraphPad Software, San Diego, Calif., USA). A p value smaller than 0.05 (two-tailed) was considered as statistically significant during comparison based on Student's t-test.

Results

Urinary Polyamines Content

Figure 1:
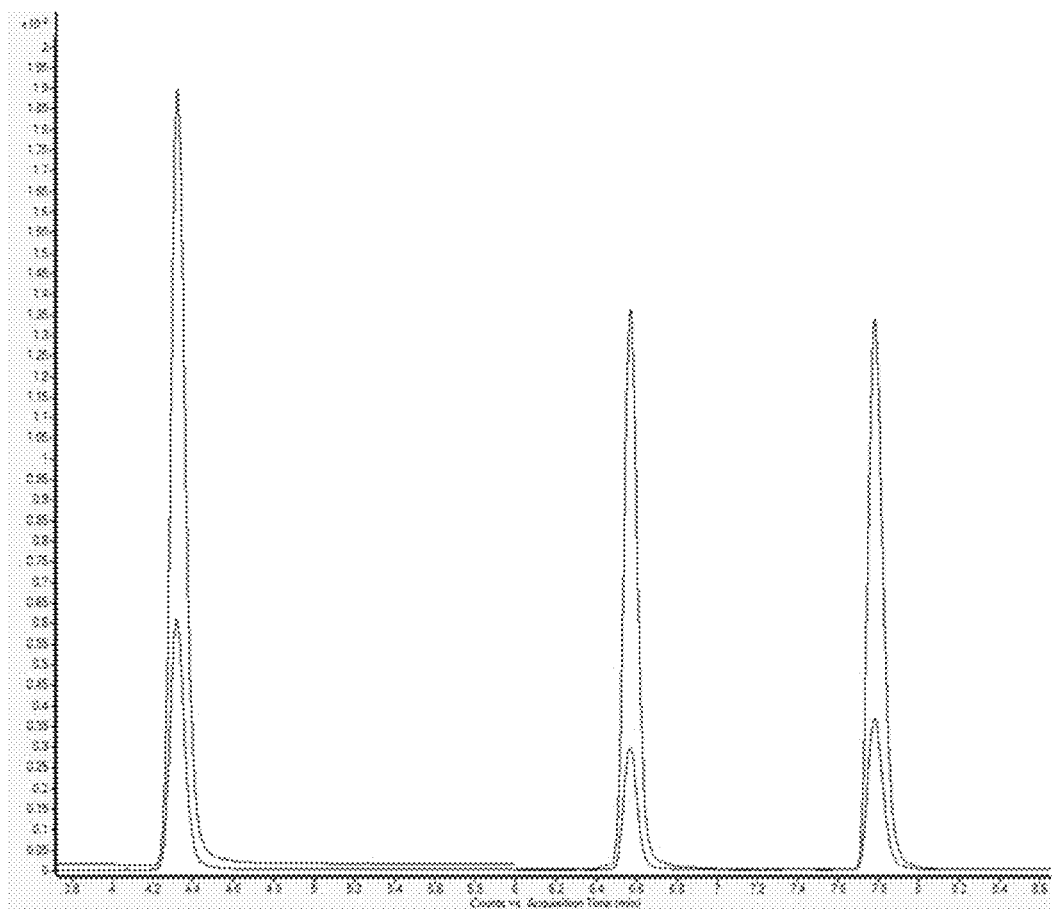
FIG. 1 shows the overlaid UPLC-MS/MS SRM chromatograms of 1000 ppb mixed polyamines standard (0-10 mins being shown). Put (Large peak, $t_R$=4.3 min), Put-$d_8$ (Small peak, $t_R$=4.3 min), Spd (Large peak, $t_R$=6.6 min), Spd-$d_8$ (Small peak, $t_R$=6.6 min), Spm (Large peak, $t_R$=7.8 min) and Spm-$d_8$ (Small peak, $t_R$=7.8 min).
Figure 5A:
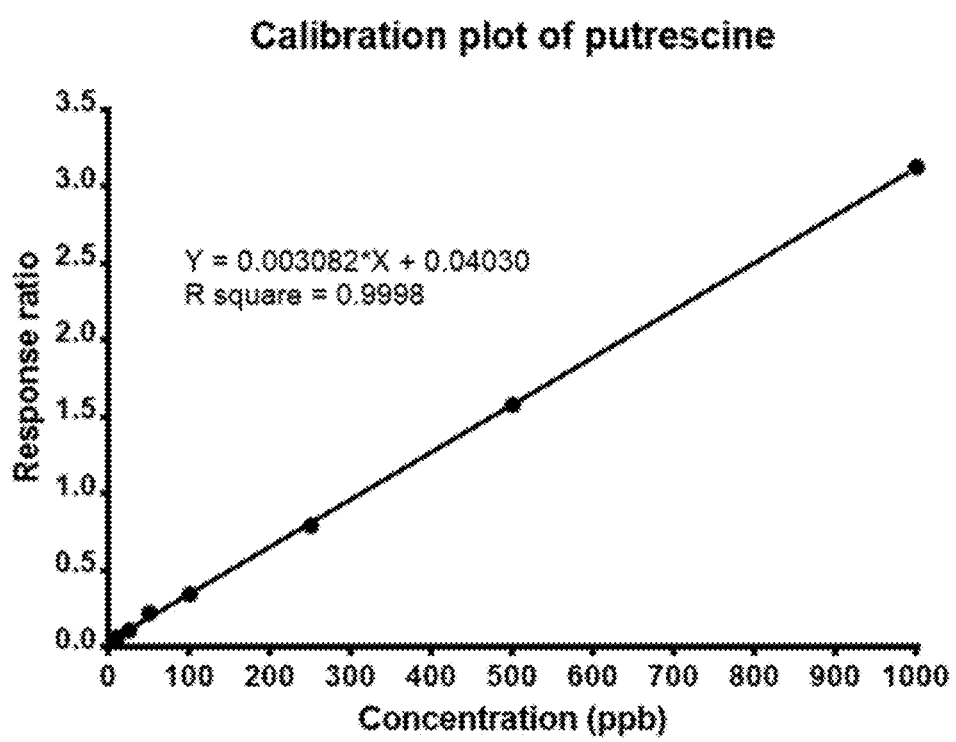
FIG. 5A shows the calibration graph for Put ($r^2$=0.9996).
Figure 5B:
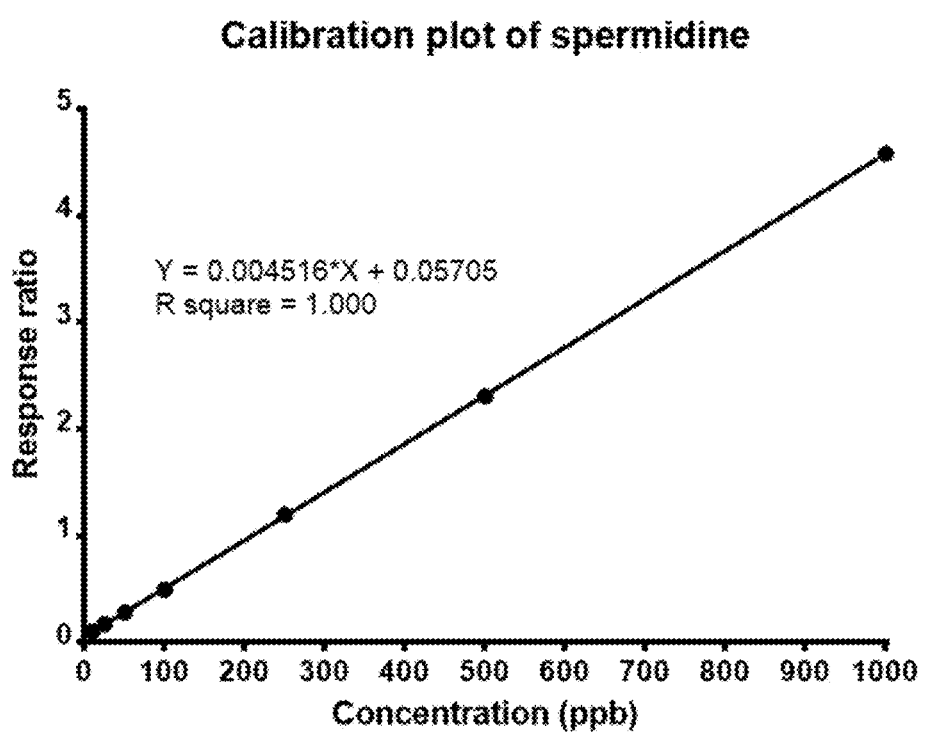
FIG. 5B shows the calibration graph for Spd ($r^2$=0.9993).
Figure 5C:
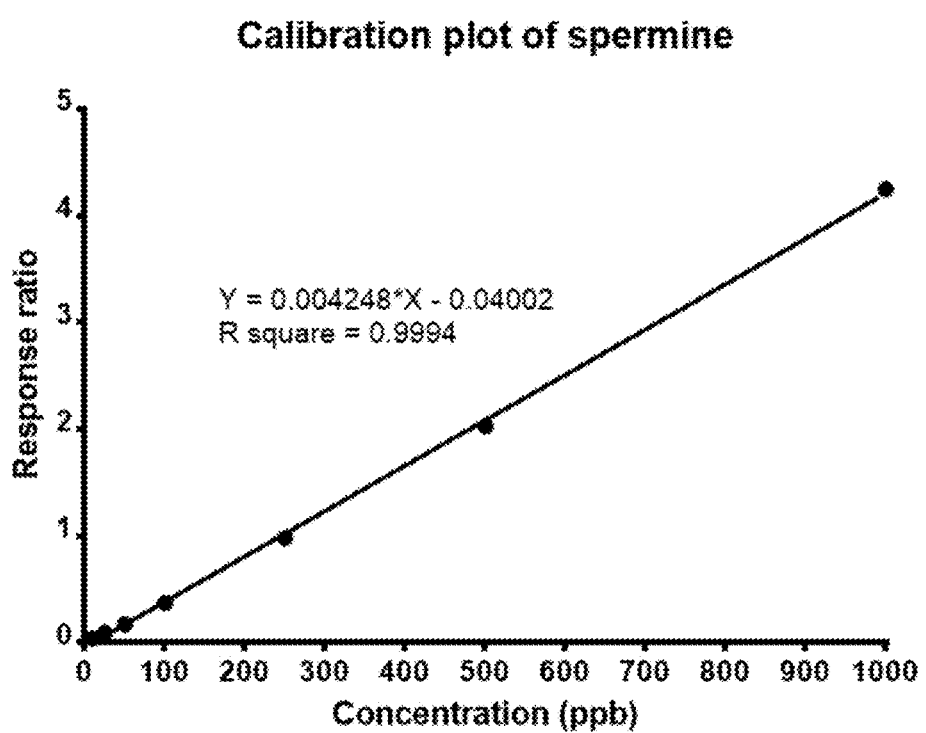
FIG. 5C shows the calibration graph for Spm ($r^2$=0.9995).

Put, Spd, Spm and their corresponding deuterated internal standards were successfully separated and quantified from all samples by UPLC-MS/MS. (FIG. 1) The calibration curves were all satisfactory with $r^2$ not less than 0.995 (FIG. 5A-FIG. 5C), and all QC measures passed which guaranteed the comparability between samples analyzed on different days. The mean urinary polyamines concentration for each patient was then normalized to their urinary creatinine levels and expressed as μmol/g of creatinine. (See Table 3 for creatinine results) This is to compensate for any diuresis processes hindering actual quantity measurements with reference to Jung K. *Enzyme activities in urine: how should we express their excretion? A critical literature review. Eur J Clin Chem Clin Biochem.* 1991; 29:725-9.

TABLE 3

Summary of creatinine results from all patients

|  | PCa (n = 66) | BPH (n = 88) | Healthy control (n = 11) | p value (PCa vs BPH) | p value (PCa vs HF) | p value (BPH vs HF) |
|---|---|---|---|---|---|---|
| Creatinine (ppm) |  |  |  |  |  |  |
| Mean (SEM) | 828.30 (76.82) | 970.40 (69.06) | 1143 (269.40) | 0.173 | 0.151 | 0.427 |
| Median | 671.31 | 751.80 | 951.98 |  |  |  |
| Range | 119.57-3102.61 | 171.43-3025.24 | 174.16-3183.77 |  |  |  |

Figure 2A:
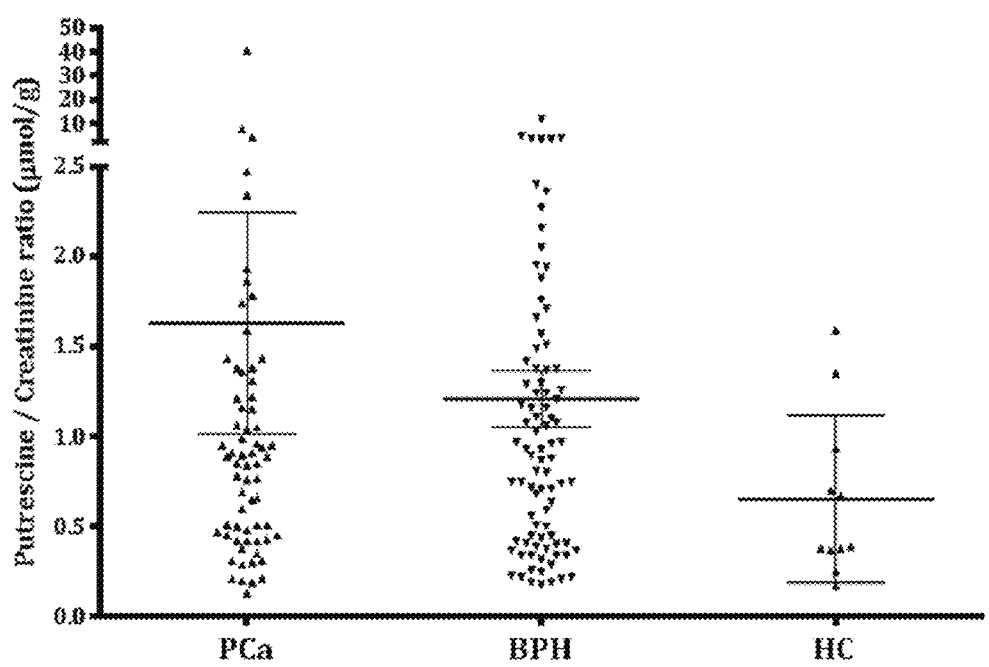
FIG. 2A shows the distribution of normalized Put values in PCa, BPH and HC.
Figure 2B:
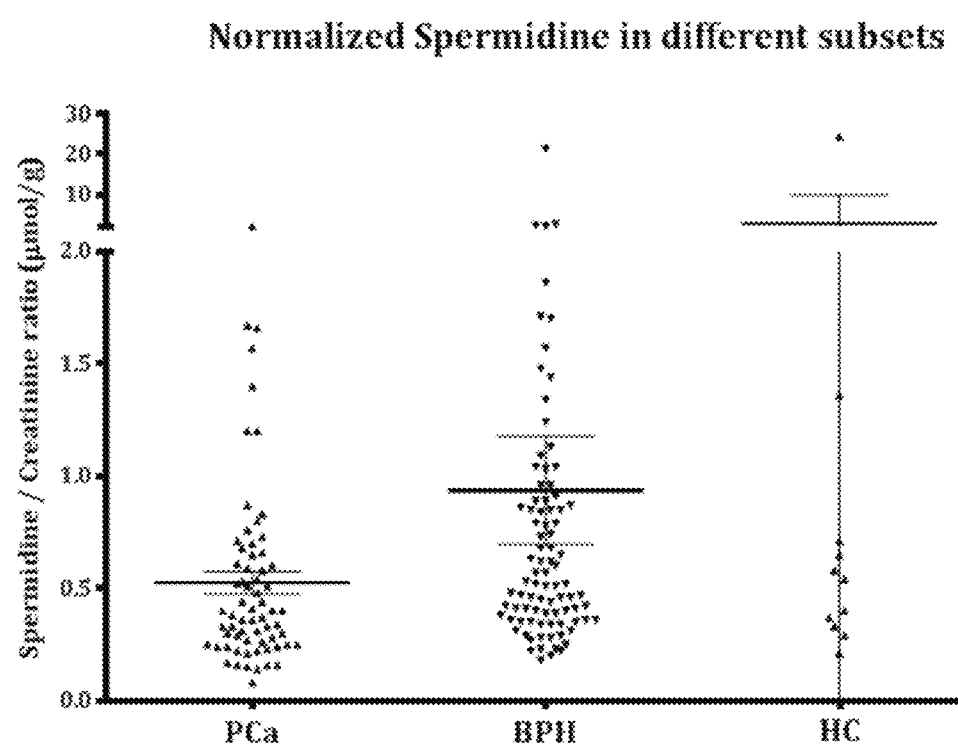
FIG. 2B shows the distribution of normalized Spd values in PCa, BPH and HC.
Figure 2C:
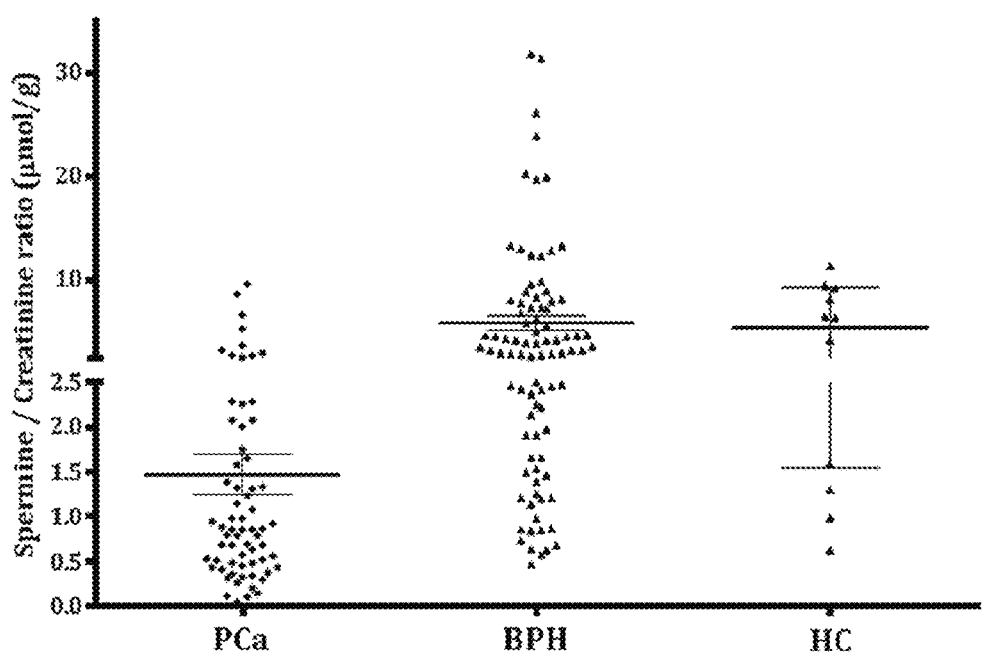
FIG. 2C shows the distribution of normalized Spm values in PCa, BPH and HC.

Table 4 and FIG. 2A to FIG. 2C show the data and graphical comparison of different subsets' normalized polyamines levels:

TABLE 4

Column statistics of normalized polyamine contents in different subsets. SEM represents the standard error of the mean.

|  | PCa | BPH | HC | p value (PCa vs BPH) | p value (PCa vs HC) | p value (BPH vs HC) |
|---|---|---|---|---|---|---|
| Normalized Put |  |  |  |  |  |  |
| Mean (SEM) | 1.63(0.61) | 1.21(0.16) | 0.65(0.14) | 0.459 | 0.522 | 0.212 |
| Median | 0.87 | 0.92 | 0.39 |  |  |  |
| Range | 0.13-40.64 | 0.18-12.04 | 0.17-1.59 |  |  |  |
| 25% Percentile | 0.45 | 0.41 | 0.37 |  |  |  |
| 75% Percentile | 1.24 | 1.38 | 0.93 |  |  |  |
| Normalized Spd |  |  |  |  |  |  |
| Mean (SEM) | 0.52(0.05) | 0.94(0.24) | 2.71(2.17) | 0.147 | 0.014 | 0.081 |
| Median | 0.39 | 0.52 | 0.54 |  |  |  |
| Range | 0.08-2.09 | 0.18-21.42 | 0.21-24.40 |  |  |  |
| 25% Percentile | 0.25 | 0.36 | 0.33 |  |  |  |
| 75% Percentile | 0.65 | 0.89 | 0.71 |  |  |  |
| Normalized Spm |  |  |  |  |  |  |
| Mean (SEM) | 1.47(0.22) | 5.87(0.71) | 5.43(1.17) | <0.0001 | <0.0001 | 0.833 |
| Median | 0.86 | 3.25 | 6.37 |  |  |  |
| Range | 0.05-9.57 | 0.47-31.78 | 0.63-11.36 |  |  |  |
| 25% Percentile | 0.48 | 1.72 | 1.30 |  |  |  |
| 75% Percentile | 1.82 | 7.65 | 9.18 |  |  |  |

The black bar in FIG. 2A to FIG. 2C indicates the mean value of each subset while the error bar indicates the corresponding SEM.

Among the three polyamines monitored, normalized Spm showed a significant decrease in PCa patients compared to non-cancerous cases including BPH patients and HC in terms of statistical means (Unpaired student's t-test). In detail, the mean value was 1.47 in PCa vs 5.87 in BPH vs 5.43 in HC. p values were <0.0001 in t-test, which means significant differences at the pre-set criteria of $p<0.05$. For normalized Put and Spd, no obvious enhancement or suppression could be observed by looking at their distributions or comparing their mean values by t-test. (Put: 1.63 in PCa vs 1.21 in BPH vs 0.65 in HC; Spd: 0.52 in PCa vs 0.94 in BPH vs 2.71 in HC)

Receiver Operating Characteristics Analysis

Figure 3:
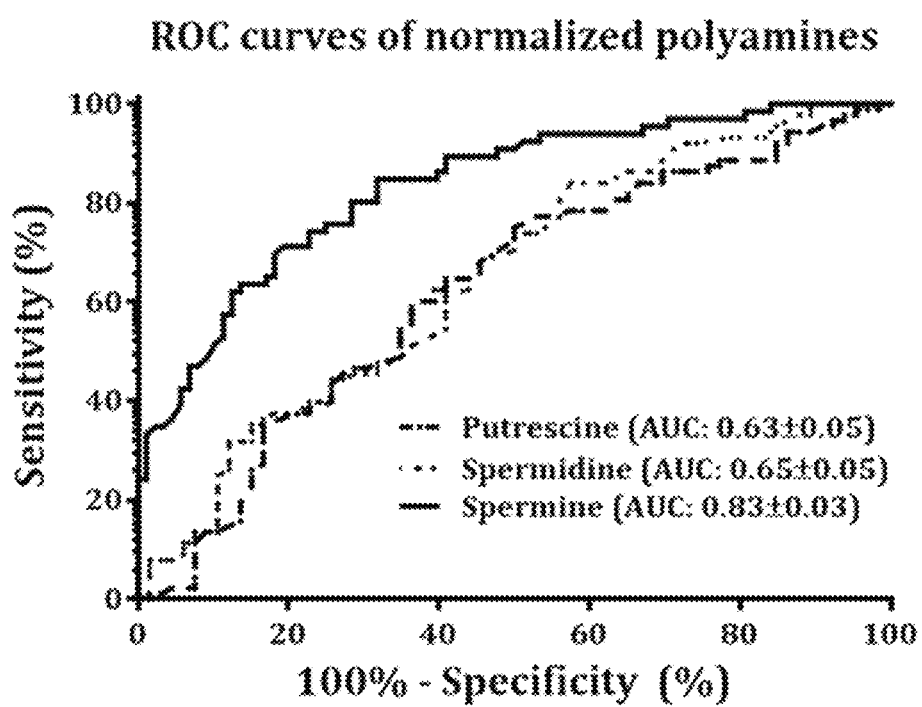
FIG. 3 shows the receiver operating characteristic analysis for normalized Put, Spd and Spm values.

FIG. 3 shows the ROC curves of the three normalized polyamines for evaluating the diagnostic power of the shortlisted polyamines for PCa diagnosis. The AUC for normalized Put, Spd and Spm were found to be 0.63±0.05, 0.65±0.05 and 0.83±0.03 respectively. The threshold values for Spm with the corresponding sensitivity and specificity were listed in Table 5.

TABLE 5

Sensitivity and Specificity for normalized Spm at different threshold values

| Threshold | Sensitivity (%) | 95% CI | Specificity (%) | 95% CI |
|---|---|---|---|---|
| <0.0800 | 1.515 | 0.03835% to 8.155% | 100. | 96.34% to 100.0% |
| <0.1150 | 3.03 | 0.3691% to 10.52% | 100 | 96.34% to 100.0% |
| <0.1350 | 4.545 | 0.9474% to 12.71% | 100 | 96.34% to 100.0% |
| <0.1800 | 6.061 | 1.676% to 14.80% | 100 | 96.34% to 100.0% |
| <0.2400 | 7.576 | 2.506% to 16.80% | 100 | 96.34% to 100.0% |
| <0.2900 | 9.091 | 3.410% to 18.74% | 100 | 96.34% to 100.0% |
| <0.3150 | 10.61 | 4.372% to 20.64% | 100 | 96.34% to 100.0% |
| <0.3250 | 12.12 | 5.381% to 22.49% | 100 | 96.34% to 100.0% |
| <0.3350 | 13.64 | 6.430% to 24.31% | 100 | 96.34% to 100.0% |
| <0.3550 | 15.15 | 7.512% to 26.10% | 100 | 96.34% to 100.0% |
| <0.3750 | 16.67 | 8.625% to 27.87% | 100 | 96.34% to 100.0% |
| <0.4000 | 18.18 | 9.763% to 29.61% | 100 | 96.34% to 100.0% |
| <0.4300 | 19.7 | 10.93% to 31.32% | 100 | 96.34% to 100.0% |
| <0.4450 | 22.73 | 13.31% to 34.70% | 100 | 96.34% to 100.0% |
| <0.4600 | 24.24 | 14.54% to 36.36% | 100 | 96.34% to 100.0% |
| <0.4800 | 24.24 | 14.54% to 36.36% | 98.99 | 94.50% to 99.97% |
| <0.5000 | 27.27 | 17.03% to 39.64% | 98.99 | 94.50% to 99.97% |
| <0.5200 | 28.79 | 18.30% to 41.25% | 98.99 | 94.50% to 99.97% |
| <0.5350 | 30.3 | 19.59% to 42.85% | 98.99 | 94.50% to 99.97% |
| <0.5500 | 31.82 | 20.89% to 44.44% | 98.99 | 94.50% to 99.97% |
| <0.5700 | 33.33 | 22.20% to 46.01% | 98.99 | 94.50% to 99.97% |
| <0.6050 | 34.85 | 23.53% to 47.58% | 97.98 | 92.89% to 99.75% |
| <0.6350 | 34.85 | 23.53% to 47.58% | 95.96 | 89.98% to 98.89% |
| <0.6600 | 36.36 | 24.87% to 49.13% | 94.95 | 88.61% to 98.34% |
| <0.6850 | 39.39 | 27.58% to 52.19% | 93.94 | 87.27% to 97.74% |
| <0.6950 | 40.91 | 28.95% to 53.71% | 93.94 | 87.27% to 97.74% |
| <0.7200 | 42.42 | 30.34% to 55.21% | 93.94 | 87.27% to 97.74% |
| <0.7650 | 42.42 | 30.34% to 55.21% | 92.93 | 85.97% to 97.11% |
| <0.7950 | 45.45 | 33.14% to 58.19% | 92.93 | 85.97% to 97.11% |
| <0.8200 | 46.97 | 34.56% to 59.66% | 92.93 | 85.97% to 97.11% |
| <0.8450 | 46.97 | 34.56% to 59.66% | 91.92 | 84.70% to 96.45% |
| <0.8550 | 48.48 | 35.99% to 61.12% | 90.91 | 83.44% to 95.76% |
| <0.8650 | 51.52 | 38.88% to 64.01% | 89.9 | 82.21% to 95.05% |
| <0.8800 | 53.03 | 40.34% to 65.44% | 88.89 | 80.99% to 94.32% |
| <0.9100 | 54.55 | 41.81% to 66.86% | 88.89 | 80.99% to 94.32% |
| <0.9400 | 56.06 | 43.30% to 68.26% | 88.89 | 80.99% to 94.32% |
| <0.9650 | 57.58 | 44.79% to 69.66% | 88.89 | 80.99% to 94.32% |
| <0.9850 | 57.58 | 44.79% to 69.66% | 87.88 | 79.78% to 93.58% |
| <1.035 | 60.61 | 47.81% to 72.42% | 86.87 | 78.59% to 92.82% |
| <1.110 | 62.12 | 49.34% to 73.78% | 86.87 | 78.59% to 92.82% |
| <1.145 | 62.12 | 49.34% to 73.78% | 85.86 | 77.41% to 92.05% |
| <1.175 | 63.64 | 50.87% to 75.13% | 85.86 | 77.41% to 92.05% |
| <1.205 | 63.64 | 50.87% to 75.13% | 84.85 | 76.24% to 91.26% |
| <1.225 | 63.64 | 50.87% to 75.13% | 82.83 | 73.94% to 89.67% |
| <1.250 | 65.15 | 52.42% to 76.47% | 82.83 | 73.94% to 89.67% |
| <1.280 | 65.15 | 52.42% to 76.47% | 81.82 | 72.80% to 88.85% |
| <1.305 | 65.15 | 52.42% to 76.47% | 80.81 | 71.66% to 88.03% |
| <1.320 | 66.67 | 53.99% to 77.80% | 80.81 | 71.66% to 88.03% |
| <1.335 | 68.18 | 55.56% to 79.11% | 80.81 | 71.66% to 88.03% |
| <1.365 | 69.7 | 57.15% to 80.41% | 80.81 | 71.66% to 88.03% |
| <1.425 | 71.21 | 58.75% to 81.70% | 79.8 | 70.54% to 87.20% |
| <1.480 | 71.21 | 58.75% to 81.70% | 78.79 | 69.42% to 86.36% |
| <1.520 | 71.21 | 58.75% to 81.70% | 77.78 | 68.31% to 85.52% |
| <1.560 | 71.21 | 58.75% to 81.70% | 76.77 | 67.21% to 84.67% |
| <1.585 | 72.73 | 60.36% to 82.97% | 76.77 | 67.21% to 84.67% |
| <1.620 | 72.73 | 60.36% to 82.97% | 75.76 | 66.11% to 83.81% |
| <1.655 | 74.24 | 61.99% to 84.22% | 75.76 | 66.11% to 83.81% |
| <1.705 | 74.24 | 61.99% to 84.22% | 73.74 | 63.93% to 82.07% |
| <1.830 | 75.76 | 63.64% to 85.46% | 73.74 | 63.93% to 82.07% |
| <1.940 | 75.76 | 63.64% to 85.46% | 71.72 | 61.78% to 80.31% |
| <1.990 | 75.76 | 63.64% to 85.46% | 70.71 | 60.71% to 79.43% |
| <2.045 | 77.27 | 65.30% to 86.69% | 70.71 | 60.71% to 79.43% |
| <2.105 | 80.3 | 68.68% to 89.07% | 70.71 | 60.71% to 79.43% |
| <2.175 | 80.3 | 68.68% to 89.07% | 69.7 | 59.64% to 78.53% |
| <2.235 | 80.3 | 68.68% to 89.07% | 68.69 | 58.59% to 77.64% |
| <2.255 | 80.3 | 68.68% to 89.07% | 67.68 | 57.53% to 76.73% |
| <2.270 | 81.82 | 70.39% to 90.24% | 67.68 | 57.53% to 76.73% |
| <2.325 | 84.85 | 73.90% to 92.49% | 67.68 | 57.53% to 76.73% |
| <2.390 | 84.85 | 73.90% to 92.49% | 66.67 | 56.48% to 75.82% |
| <2.415 | 84.85 | 73.90% to 92.49% | 65.66 | 55.44% to 74.91% |
| <2.435 | 84.85 | 73.90% to 92.49% | 64.65 | 54.40% to 73.99% |
| <2.455 | 84.85 | 73.90% to 92.49% | 63.64 | 53.36% to 73.07% |
| <2.465 | 84.85 | 73.90% to 92.49% | 62.63 | 52.33% to 72.15% |
| <2.485 | 84.85 | 73.90% to 92.49% | 61.62 | 51.30% to 71.22% |

TABLE 5-continued

Sensitivity and Specificity for normalized Spm at different threshold values

| Threshold | Sensitivity (%) | 95% CI | Specificity (%) | 95% CI |
|---|---|---|---|---|
| <2.510 | 84.85 | 73.90% to 92.49% | 60.61 | 50.28% to 70.28% |
| <2.585 | 86.36 | 75.69% to 93.57% | 60.61 | 50.28% to 70.28% |
| <2.665 | 86.36 | 75.69% to 93.57% | 59.6 | 49.26% to 69.34% |
| <2.715 | 87.88 | 77.51% to 94.62% | 59.6 | 49.26% to 69.34% |
| <2.770 | 89.39 | 79.36% to 95.63% | 59.6 | 49.26% to 69.34% |
| <2.800 | 89.39 | 79.36% to 95.63% | 58.59 | 48.24% to 68.40% |
| <2.820 | 89.39 | 79.36% to 95.63% | 57.58 | 47.23% to 67.45% |
| <2.845 | 89.39 | 79.36% to 95.63% | 56.57 | 46.23% to 66.50% |
| <2.895 | 89.39 | 79.36% to 95.63% | 55.56 | 45.22% to 65.55% |
| <2.935 | 89.39 | 79.36% to 95.63% | 54.55 | 44.22% to 64.59% |
| <2.965 | 89.39 | 79.36% to 95.63% | 53.54 | 43.23% to 63.62% |
| <3.110 | 90.91 | 81.26% to 96.59% | 53.54 | 43.23% to 63.62% |
| <3.235 | 90.91 | 81.26% to 96.59% | 52.53 | 42.24% to 62.66% |
| <3.245 | 90.91 | 81.26% to 96.59% | 51.52 | 41.25% to 61.68% |
| <3.380 | 92.42 | 83.20% to 97.49% | 50.51 | 40.27% to 60.71% |
| <3.555 | 92.42 | 83.20% to 97.49% | 49.49 | 39.29% to 59.73% |
| <3.625 | 92.42 | 83.20% to 97.49% | 48.48 | 38.32% to 58.75% |
| <3.760 | 93.94 | 85.20% to 98.32% | 48.48 | 38.32% to 58.75% |
| <3.920 | 93.94 | 85.20% to 98.32% | 47.47 | 37.34% to 57.76% |
| <4.055 | 93.94 | 85.20% to 98.32% | 46.46 | 36.38% to 56.77% |
| <4.170 | 93.94 | 85.20% to 98.32% | 45.45 | 35.41% to 55.78% |
| <4.205 | 93.94 | 85.20% to 98.32% | 44.44 | 34.45% to 54.78% |
| <4.235 | 93.94 | 85.20% to 98.32% | 43.43 | 33.50% to 53.77% |
| <4.290 | 93.94 | 85.20% to 98.32% | 42.42 | 32.55% to 52.77% |
| <4.430 | 93.94 | 85.20% to 98.32% | 41.41 | 31.60% to 51.76% |
| <4.560 | 93.94 | 85.20% to 98.32% | 40.4 | 30.66% to 50.74% |
| <4.595 | 93.94 | 85.20% to 98.32% | 39.39 | 29.72% to 49.72% |
| <4.625 | 93.94 | 85.20% to 98.32% | 38.38 | 28.78% to 48.70% |
| <4.695 | 93.94 | 85.20% to 98.32% | 37.37 | 27.85% to 47.67% |
| <4.880 | 93.94 | 85.20% to 98.32% | 36.36 | 26.93% to 46.64% |
| <5.180 | 93.94 | 85.20% to 98.32% | 35.35 | 26.01% to 45.60% |
| <5.440 | 95.45 | 87.29% to 99.05% | 35.35 | 26.01% to 45.60% |
| <5.700 | 95.45 | 87.29% to 99.05% | 34.34 | 25.09% to 44.56% |
| <6.055 | 95.45 | 87.29% to 99.05% | 33.33 | 24.18% to 43.52% |
| <6.305 | 95.45 | 87.29% to 99.05% | 32.32 | 23.27% to 42.47% |
| <6.435 | 95.45 | 87.29% to 99.05% | 31.31 | 22.36% to 41.41% |
| <6.555 | 95.45 | 87.29% to 99.05% | 30.3 | 21.47% to 40.36% |
| <6.685 | 96.97 | 89.48% to 99.63% | 30.3 | 21.47% to 40.36% |
| <7.000 | 96.97 | 89.48% to 99.63% | 29.29 | 20.57% to 39.29% |
| <7.270 | 96.97 | 89.48% to 99.63% | 28.28 | 19.69% to 38.22% |
| <7.310 | 96.97 | 89.48% to 99.63% | 27.27 | 18.80% to 37.15% |
| <7.540 | 96.97 | 89.48% to 99.63% | 26.26 | 17.93% to 36.07% |
| <7.885 | 96.97 | 89.48% to 99.63% | 25.25 | 17.06% to 34.98% |
| <8.060 | 96.97 | 89.48% to 99.63% | 24.24 | 16.19% to 33.89% |
| <8.130 | 96.97 | 89.48% to 99.63% | 23.23 | 15.33% to 32.79% |
| <8.245 | 96.97 | 89.48% to 99.63% | 21.21 | 13.64% to 30.58% |
| <8.495 | 96.97 | 89.48% to 99.63% | 20.2 | 12.80% to 29.46% |
| <8.755 | 98.48 | 91.84% to 99.96% | 20.2 | 12.80% to 29.46% |
| <8.880 | 98.48 | 91.84% to 99.96% | 19.19 | 11.97% to 28.34% |
| <9.040 | 98.48 | 91.84% to 99.96% | 18.18 | 11.15% to 27.20% |
| <9.335 | 98.48 | 91.84% to 99.96% | 17.17 | 10.33% to 26.06% |
| <9.520 | 98.48 | 91.84% to 99.96% | 16.16 | 9.530% to 24.91% |
| <9.560 | 98.48 | 91.84% to 99.96% | 15.15 | 8.736% to 23.76% |
| <9.700 | 100 | 94.56% to 100.0% | 15.15 | 8.736% to 23.76% |
| <10.60 | 100 | 94.56% to 100.0% | 14.14 | 7.953% to 22.59% |
| <11.85 | 100 | 94.56% to 100.0% | 13.13 | 7.181% to 21.41% |
| <12.38 | 100 | 94.56% to 100.0% | 12.12 | 6.423% to 20.22% |
| <12.63 | 100 | 94.56% to 100.0% | 11.11 | 5.679% to 19.01% |
| <12.93 | 100 | 94.56% to 100.0% | 10.1 | 4.951% to 17.79% |
| <13.15 | 100 | 94.56% to 100.0% | 9.091 | 4.242% to 16.56% |
| <13.29 | 100 | 94.56% to 100.0% | 8.081 | 3.553% to 15.30% |
| <16.50 | 100 | 94.56% to 100.0% | 7.071 | 2.890% to 14.03% |
| <19.83 | 100 | 94.56% to 100.0% | 6.061 | 2.256% to 12.73% |
| <20.11 | 100 | 94.56% to 100.0% | 5.051 | 1.660% to 11.39% |
| <22.08 | 100 | 94.56% to 100.0% | 4.04 | 1.112% to 10.02% |
| <25.01 | 100 | 94.56% to 100.0% | 3.03 | 0.6293% to 8.601% |
| <28.75 | 100 | 94.56% to 100.0% | 2.02 | 0.2456% to 7.108% |
| <31.57 | 100 | 94.56% to 100.0% | 1.01 | 0.02557% to 5.500% |

The relationship between polyamines and cancer has long been investigated by scientists. It is generally believed that increase of polyamine levels in blood or urine reflect the enhanced levels of polyamine synthesis in rapid-growing cancer tissues/cells, since they are associated with increased cell proliferation, decreased apoptosis and increased expression of genes affecting tumor invasion and metastasis.

In Russell D H. *Increased polyamine concentrations in the urine of human cancer patients. Nat New Biol.* 1971; 233(39):144-5 firstly reported the increase of urinary polyamines levels in various solid tumors, including ovarian teratoma, rectal carcinoma, lymphosarcoma, osteogenic sarcoma and acute myelocytic leukaemia. Kyoko Hiramatsu et al. $N^1,N^{12}$-*Diacetylspermine as a Sensitive and Specific Novel Marker for Early-and Late-Stage Colorectal and Breast Cancers. Clin Cancer Res.* 2005; 11(8):2986-90 reported an increase in $N^1,N^{12}$-Diacetylspermine in patients with early and late stage colorectal and breast cancers and established its role to be a novel marker for these cancers. In cases of cervical cancer, Lee et al. *Altered urinary profiles of polyamines and endogenous steroids in patients with benign cervical disease and cervical cancer. Cancer Lett.* 2003; 201(2): 121-31 had shown a significant elevation in polyamines level in Put, Spd and Spm. For hepatic cancer, Liu et al. *Determination of polyamine metabolome in plasma and urine by ultrahigh performance liquid chromatography-tandem mass spectrometry method: Application to identify potentialpotential markers for human hepatic cancer. Anal Chim Acta.* 2013; 791:36-45 monitored the level differences between polyamines, polyamine precursors and catabolites in both patients' plasma and urines. By analyzing these results carefully, indeed it could be observed that different kinds of polyamines showed different variations depending on the type of cancers. The claim of urinary polyamine levels elevating in cancer cases is not specific enough.

Nevertheless, very few reports focused on detecting the effects of PCa on urinary polyamines levels, which in turn might provide a potential diagnostic tool for this increasing common cancer. In 1975 Fair et al. *Urinary polyamine levels in the diagnosis of carcinoma of the prostate. J Urol.* 1975; 114(1):88-92 had reported a significant elevation of urinary Spd content in PCa patients by electrophoresis, but not Put and Spm. Horn et al. *Relationship of urinary polyamines to tumor activity and tumor volume in patients. Cancer Res.* 1984; 44(10):4675-8 analyzed urinary Spd and Put content from patients with tumors in either breast, stomach, prostate, female genital tract, or metastatic carcinomas of unknown origins by LC with fluorometric detector in 1984 yielding an indeterminant conclusion. With the advance of analytical field, in the current disclosure, the potential abilities of three natural polyamines: Put, Spd and Spm, as urinary biomarkers for screening of PCa were evaluated by UPLC-MS/MS. Through a well validated method using separate deuterated internal standards for correcting matrix effects for each polyamine, it is believed that the analytical performance was much more reliable.

The observation of a declined level in urinary Spm actually was reasonable from results of previous literatures about PCa studies. Although only a limited number of tissue specimens had been examined, van der Graaf et al. *Proton MR spectroscopy of prostatic tissue focused on the detection of spermine, a possible biomarker of malignant behavior in prostate cancer. MAGMA* 2000; 10(3): 153-9 reported a reduced Spm content in tumor prostatic tissues compared to normal and benign hyperplastic prostatic tissues by high performance liquid chromatography with fluorometric detector. Swanson et al. *Proton HR-MAS spectroscopy and quantitative pathologic analysis of MRI/3D-MRSI-targeted postsurgical prostate tissues. Magn Reson Med.* 2003; 50(5): 944-54 also reported a decreased Spm level in prostate tissue samples by Proton high-resolution magic angle spinning nuclear magnetic resonance spectroscopy and quantitative histopathology. High grade cancer prostate tissue could be distinguished from low grade cancer tissue by decreased concentrations of Spm and citrate, as reported by GF Giskeødegård et al *Spermine and citrate as metabolic biomarkers for assessing prostate cancer aggressiveness. PLoS One* 2013; 8(4):e62375. Apart from direct monitoring of prostate tissue, Serkova et al. *The metabolites citrate, myo-inositol, and spermine are potential age-independent markers of prostate cancer in human expressed prostatic secretions. Prostate.* 2008; 68(6), 620-8 reported that in human expressed prostatic secretions, citrate, myo-inositol and Spm are potentially important markers of PCa, and all of them showed a decreased level in PCa patients compared to control samples. With respect to these previous research projects, a decrease in urinary Spm content could be foreseen, because urine represents a fluid closely related to exfoliated cancer cells and secreted prostatic products from the prostate. In essence, urine has the advantages of ready availability and the collection of which is non-invasive. Therefore the discovery of a useful urine PCa biomarker is inspiring to the current medical situation for reducing unnecessary biopsies and arranging patients for appropriate therapies.

Figure 4:
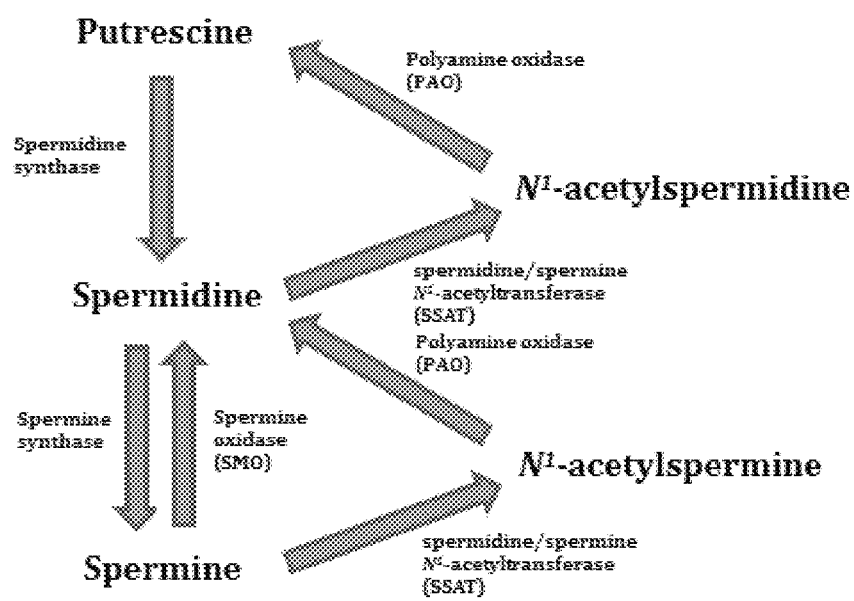
FIG. 4 shows the polyamine metabolic pathway (focusing on Put, Spd and Spm only).

To explain the declined level of Spm in PCa patients, the exact mechanisms lack clear evidence and are still under research. Schipper et al. *Polyamines and prostatic cancer. Biochem Soc Trans.* 2003; 31(2):375-80 suggested a possible explanation that changes of cell organization caused by cancer cell proliferation finally result in a decreased luminal volume, which in turn reduces the amount of secreted compounds in prostate tissue, prostatic fluid or even urine. But this could hardly explain why only urinary Spm level declined. Leo et al. *Non-destructive quantitation of spermine in human prostate tissue samples using HRMAS 1H NMR spectroscopy at 9.4 T FEBS Letters.* 2001; 494(1-2):112-6 reported that Spm was a proposed endogeneous inhibitor to prostate cancer growth, and a linear correlation was found between Spm content and the volume percentage of normal prostatic epithelial cells as quantified by histopathology. And in recent studies it was suggested that dysregulation of polyamine metabolism, or more specifically polyamine catabolism, may be involved in carcinogenesis. Increases in spermine oxidase (SMO) and spermidine/spermine $N^1$-acetyltransferase (SSAT) expression were observed in both precursor prostatic inflammatory atrophy lesions and early prostatic intraepithelial neoplastic lesions, which resulted in a depletion of Spm content (FIG. 4).

This hypothesis is also supported by the observation of a significant increase in urinary diacetylspermine content in patients with urogenital malignancies resulted from the enzymatic action of S SAT, as reported by Hiramatsu, et al. *Diagnostic and prognostic usefulness of $N^1$, $N^8$-diacetylspermidine and $N^1,N^{12}$-diacetylspermine in urine as novel markers of malignancy. J Cancer Res Clin Oncol.* 1997; 123(10):539-45. Therefore the observation of a decrease in urinary Spm, as described herein, is in line with previous findings and suggested mechanisms. Without being bound by theory, it is hypothesized that the action of SMO and SSAT counteracted each other so no significant changes were found for Spd.

Nevertheless, unlike what GF Giskeødegård et al. *Spermine and citrate as metabolic biomarkers for assessing prostate cancer aggressiveness. PLoS One* 2013; 8(4): e62375 reported that prostatic Spm content can act as a biomarker to assess PCa aggressiveness, determinant definitive conclusion on whether urinary Spm shows similar cancer grade-differentiating ability could be established from the data disclosed herein. From the results, a drop in high grade cancer (GS=8-10) was observed comparing with low grade cancer (GS≤6), albeit not that significant. (1.23 in High grade vs 1.47 in low grade; p=0.611) Instead, it acts like a diagnostic biomarker working in accordance with TRUSPB for PCa diagnosis.

Figure 6:
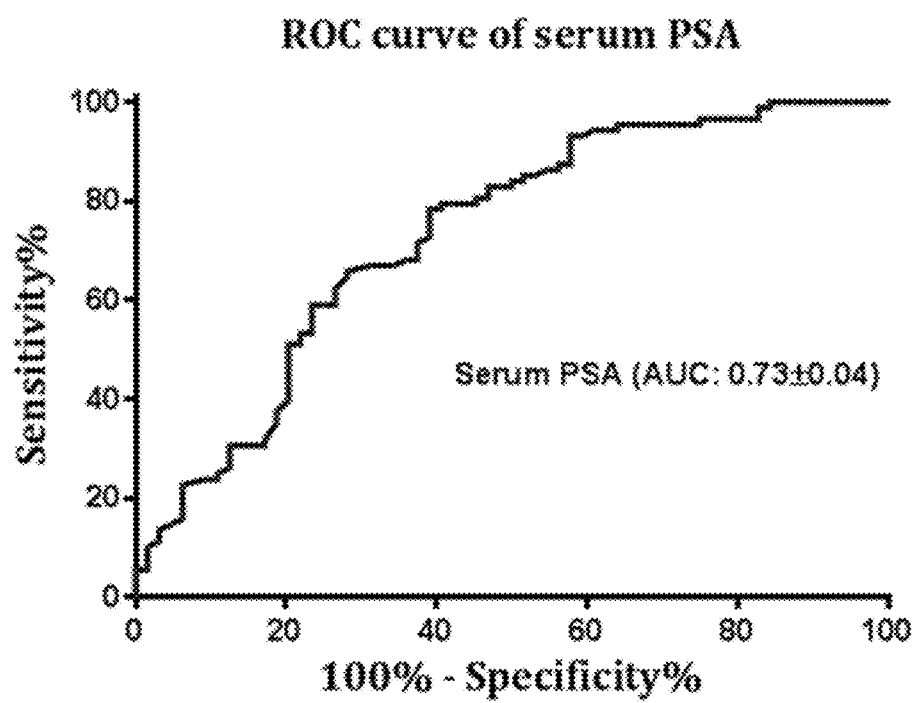
FIG. 6 shows the receiver operating characteristics curve for serum PSA test.

The PSA test leaves much to be desired as a primary screening test. It has been shown to cause over-diagnosis especially in patients showing values in the grey zone. For example, serum PSA alone demonstrated fair sensitivity and specificity of 65% and 47% respectively. Li et al. *Macrophage inhibitory cytokine 1 biomarker serum immunoassay in combination with PSA is a more specific diagnostic tool for detection of prostate cancer. PLoS One.* 2015; 10(4): e0122249 reported an even poorer sensitivity and specificity for it in their study (Sensitivity=54.8%, Specificity=57.1%, AUC=0.684). Another large-scale study by Ferro et al. *Prostate Health Index (Phi) and Prostate Cancer Antigen 3 (PCA3) significantly improve prostate cancer detection at initial biopsy in a total PSA range of 2-10 ng/ml. PLoS One* 2013; 8(7):e67687 showed that total PSA only gave AUC value of 0.52±0.07. When focusing on patients with PSA>4.0 ng/ml, the PSA test shows the best screening performance (AUC=0.73±0.04; See FIG. 6), but it is still poorer than that of urinary Spm testing methods described herein. Sensitivity and specificity were 67.05% and 68.75% respectively. Therefore urinary Spm is able to act as a secondary screening test to men with serum PSA>4.0 ng/ml to differentiate PCa and non-cancerous cases including BPH for supplementing PSA test.

To conclude on the basis of the first part of the present disclosure, the potential roles of the three main urinary polyamines as PCa biomarkers were evaluated. Among Put, Spd and Spm, Spm demonstrated an outstanding diagnostic performance for PCa, in particular for patients with elevated serum PSA level, upon comparison of their levels in PCa and BPH patients. Its AUC value is 0.83±0.03. This could help the current medical challenge brought by poor specificity of serum PSA test. And with our developed lanthanide based bioprobes, we can achieve a simple and quick quantification for PCa screening.

Part 2: Synthesized Lanthanide Complexes for Spm Sensing

A series of lanthanide compounds (1) was developed that is useful in the colorimetric quantitative and qualitative analysis of urinary polyamines.

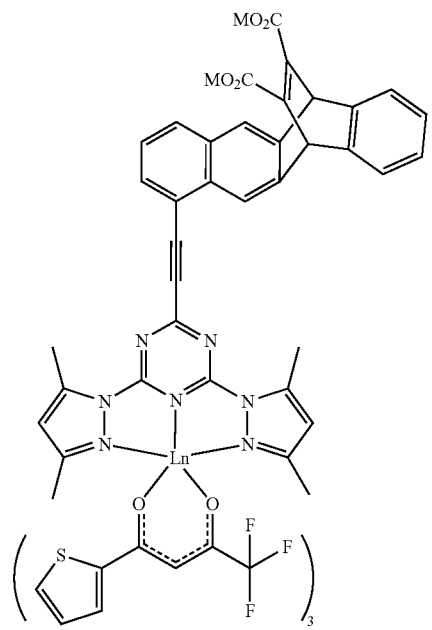

wherein,
Ln is a lanthanide metal; and
each M is independently selected from the group consisting of Na, Li, and K; or two M taken together represent Mg or Ca. In certain embodiments, two M taken together represent Mg, Ca, Sr, or Ba.

In certain embodiments, Ln is selected from the group consisting of La, Ce, Pr, Nd, Pr, Nd, Pm, Eu, Gd, Tb, Dy, Ho, Er, Tm, Yb, and Lu. In certain embodiments, Ln is $Eu^{3+}$.

In certain embodiments, M is Li and Ln is $Eu^{3+}$.

Figure 7A:
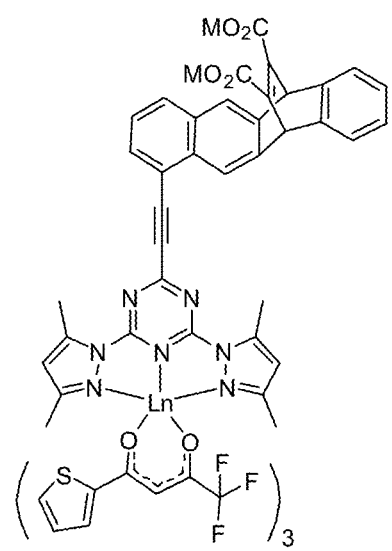
FIG. 7A shows the chemical structure of compound 1. (EuL1)
Figure 7B:
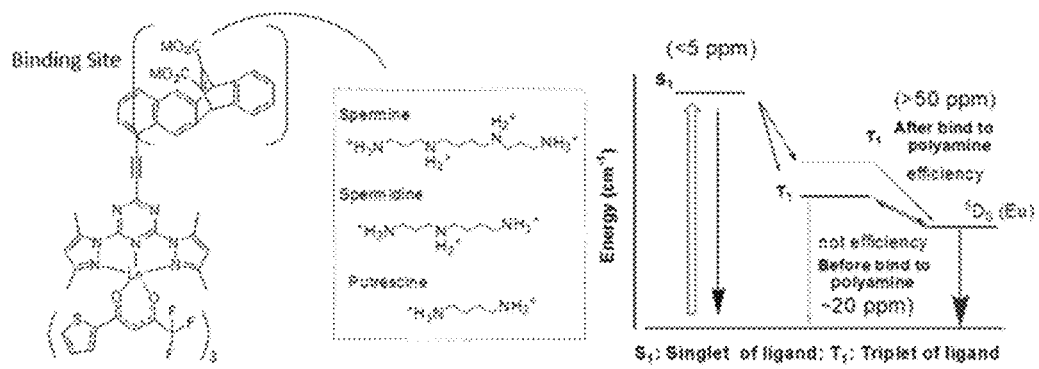
FIG. 7B shows the schematic representations of colour changing lanthanide-based polyamines chemosensors where the design is based on polyamine-activated f-f emission.
Figure 7B:
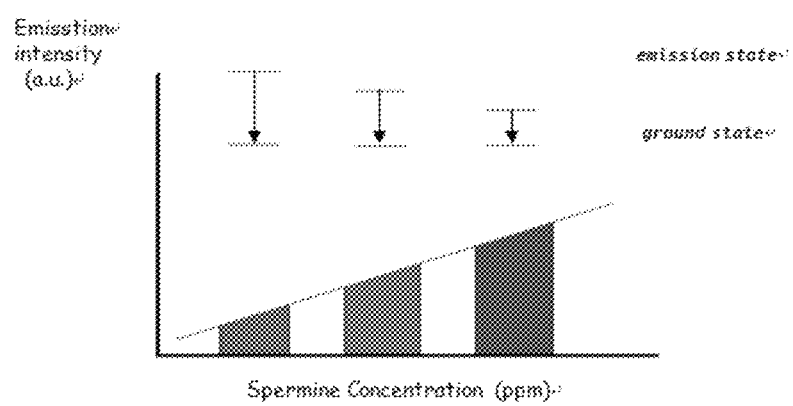
Figure 7B:
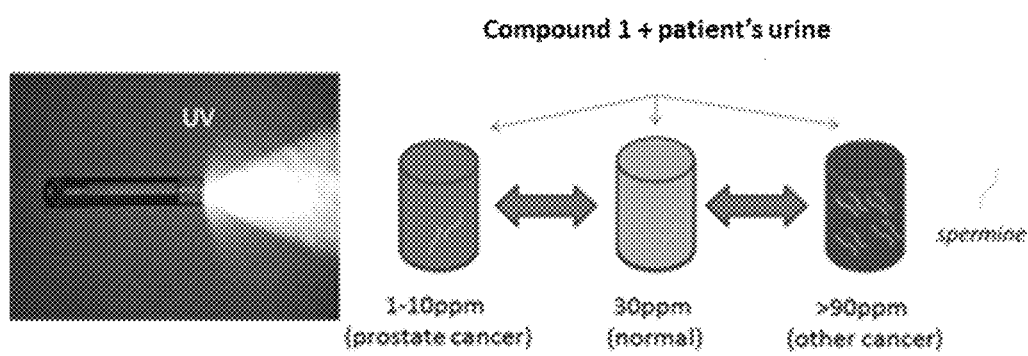

Put and n-butylamine are significantly less effective than Spm and Spd in binding multiple poly(p-phenylene ethnylene (PPE) chains (i.e., the upper portion of the compound of Formula (I)) to form tightly associated aggregates with enhanced inter-chain exciton migration. Therefore, a chemical sensor based on nonspecific electrostatic interactions could still exhibit some selectivity between similar analytes, with high means, it binds better to Spm (+4 charged) and Spd (+3 charged) and worse to putrescine (+2 charged) and n-butylamine (+1 charged) (FIGS. 7A-7B).

Figure 8A:
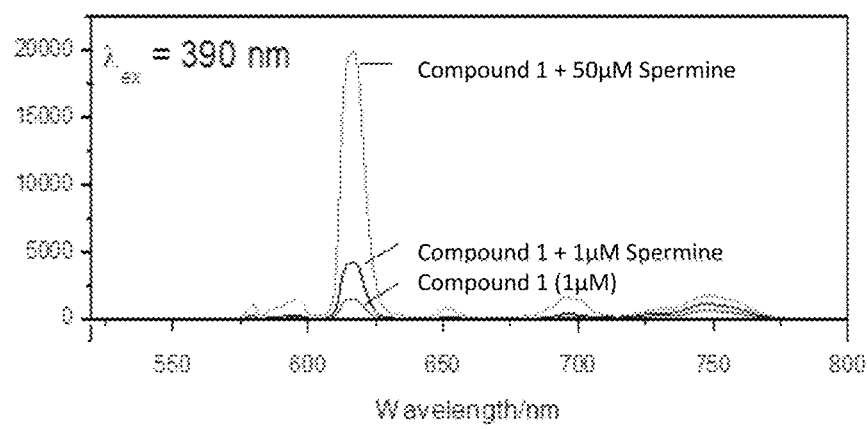
FIG. 8A shows Eu emission enhancement after compound 1 (1 μM) binds with Spm (1 μM).
Figure 8B:
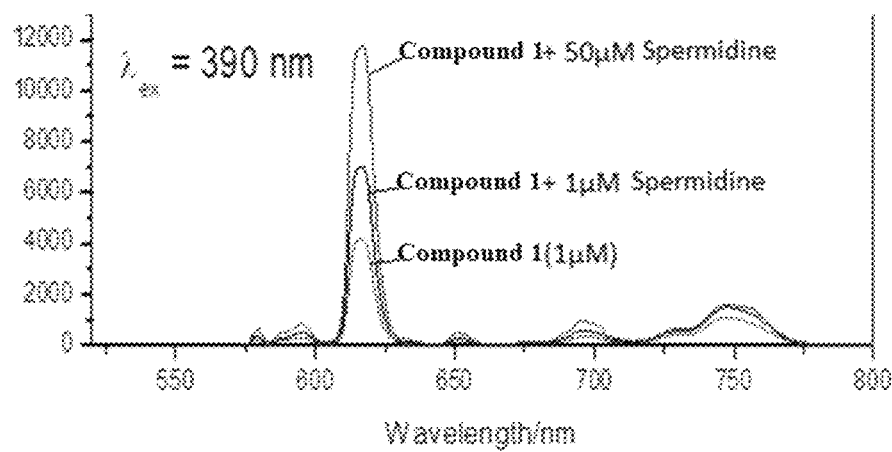
FIG. 8B shows Eu emission enhancement after compound 1 (1 μM) binds with Spd (50 μM).
Figure 8C:
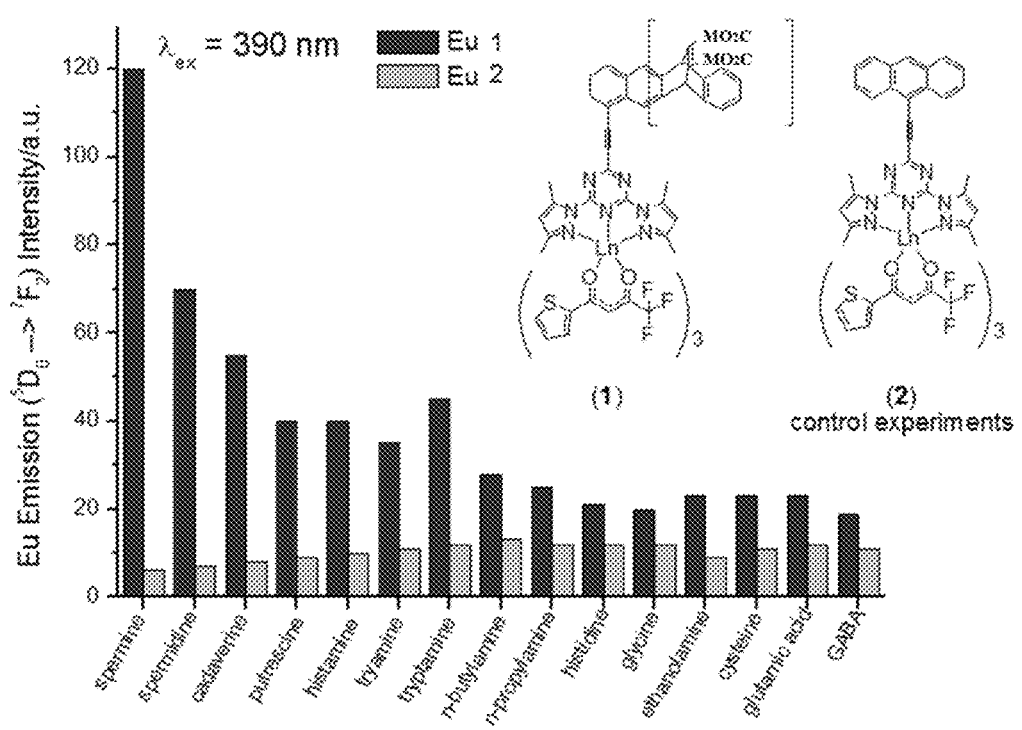
FIG. 8C shows the selectivity of compound 1 for Spm and Spd over various biogenic amines and cations in aqueous DMSO (3%-DMSO).

Ligation of the Newly Developed Chromophore to Lanthanide Complexes Reveals Strong Binding and Specific Selectivity for Polyamines Through Linear/Two-Photon Excitation Compound 1 was synthesized with the polyamines-specific binding site. (compound 1, FIG. 7B) The conjugated system controlled the triplet state of triazine-based ligand and gives green emission of the ligand. The two anionic groups in compound 1 (FIG. 7B) served as the binding to the positive charge polyamine, which is thermodynamically favourable. The multicationic analyte can interrupt the conjugated system in the complex. Four structural red f-f ($^5D_0 \rightarrow ^7F_J$, J=1-6) emission bands can be obtained from compound 1 upon excitation at 390 nm (FIGS. 8A-8C). The quantum yield (Φ) and lifetime of compound 1 are 0.05 and 0.83 ms respectively in the solution of $DMSO:H_2O$. After the complexes bind with the Spm and Spd (50 M), the emission intensity and quantum yield increase by more than 30% (the concentration of Spm and Spd in tumor blood samples are ~10 M and 46 M respectively).

Titration of Europium Compound (1) with Spm and Spd

The significant f-f emission enhancement can be visualized under UV-excitation after compound 1 binds with polyamines (FIGS. 8A and 8B). The control experiments had been done with the europium compound 2 (FIG. 7A); no significant emission changes can be observed with the addition of polyamines. (Inset of FIG. 8C—motif structure of compound 1 without anionic binding sites for polyamine) Binding ratio (1:1) and constant ($3\times10^{-5}$M) between compound 1 and polyamines had been determined by the $^5D_0 \rightarrow ^7F_2$ emission intensity with various concentration of Spm. The lifetime variations of the binding of polyamines had been monitored rather than emission. (Responsive millisecond lifetime changes have great potential for the new generation of in-situ polyamine sensors with the help of time gated system; it can eliminate the nano-/micro-second interference in the fluid/blood samples)

Selectivity of Europium Compound (1) for Spm and Spd

The selectivity of the chemosensors for Spm and Spd over other bioactive cations, such as $K^+$, $Na^+$, $Ca^{2+}$, and other biogenic amines is presented in FIG. 8B. This is particularly important because these biogenic amines can interfere with the response of polyamines to the proposed complexes in-situ. No significant interference is observed by other biogenic amines and cations. The selectivity of compound 1 for Spm and Spd is significantly greater than that for other common bioactive cations and biogenic amines (FIG. 8B). Control experiments were also conducted with a control europium complex, which did not exhibit any significant $^5D_0 \rightarrow ^7F_2$ emission enhancement in the presence of all of the tested biogenic amines and cations.

Preliminary Clinical Trial with 10 Prostate Cancer Patients' Urine Samples

Figure 9A:
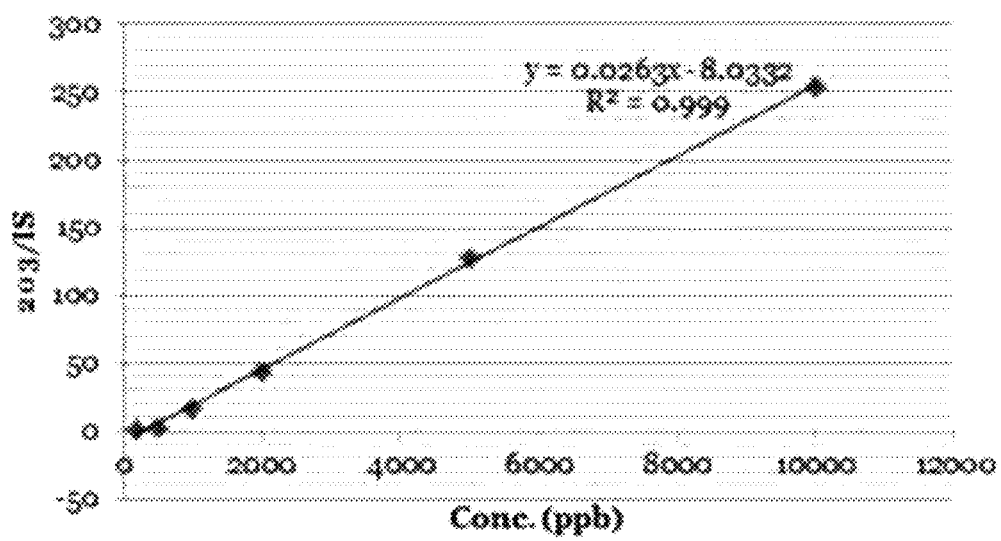
FIG. 9A shows the calibration of Spm level in 10 prostate cancer patients' urine samples.

More than 150 urine samples from prostate cancer patients were collected and analyzed for their Spm level by the standard protocol. (Creatinine level done by Jaffe's method and polyamine level checked with LC-MS/MS). The calibration curve of numerous polyamines (FIG. 9A), such as Spm—FIG. 9B and Spd have been worked out and the concentrations of these polyamine levels had been sorted out. The level determined was similar to the findings from Dr. Häkkinen in 2014.

Figure 10:
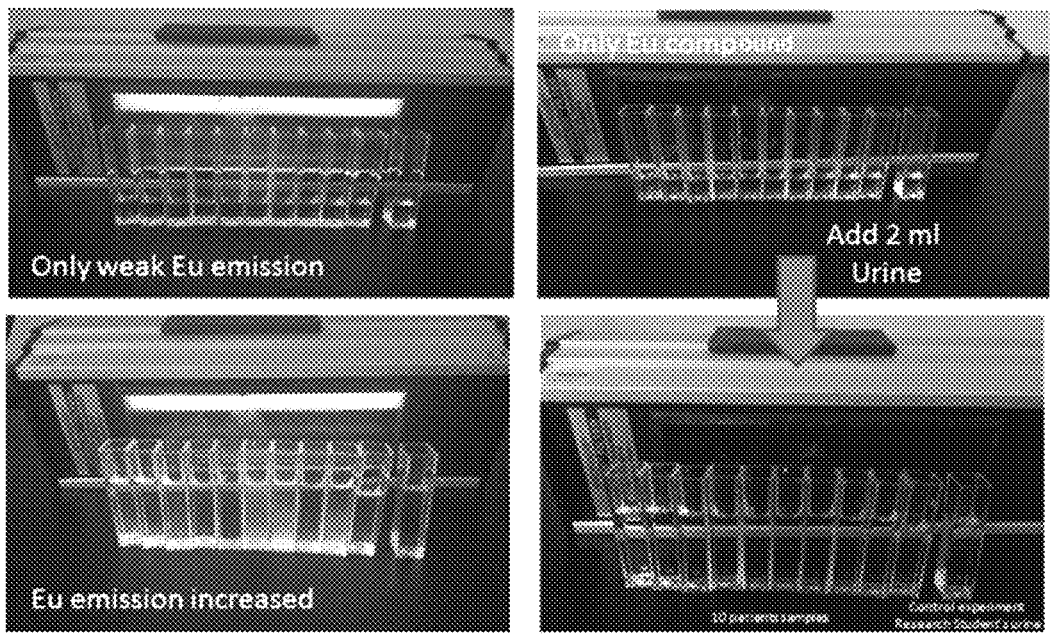
FIG. 10 shows the photographs of europium compound 1 (10 μM in aqueous solution) showing the color change in the presence of 10 prostate cancer patients urine samples under UV excitation. One urine sample from the research student was examined as the control experiment.

A series of prostate cancer patient's urine samples were selected for pre-clinical trial. Their polyamine contents were pre-determined by LC and shown in FIGS. 9A-9B. In FIG. 10, the photograph of compound 1 (10 mM in aqueous solution) shows the color change only in the presence of 10 prostate cancer patient's urine samples under the UV light. The polyamine concentration of the urine samples are evaluated by LCMS and internal standard.

Experiment-wise, 2 mL of patient urine samples will be added into 1 mL europium sensor solution (final concentration of the Eu sensor will be 50 µM). The samples will be placed in the spectrofluorometer and the responsive emission and emission lifetime signal changes will be monitored. The inventor also will monitor the emission spectra of the proposed complexes with the urine from the healthy volunteers as the control.

Figure 11:
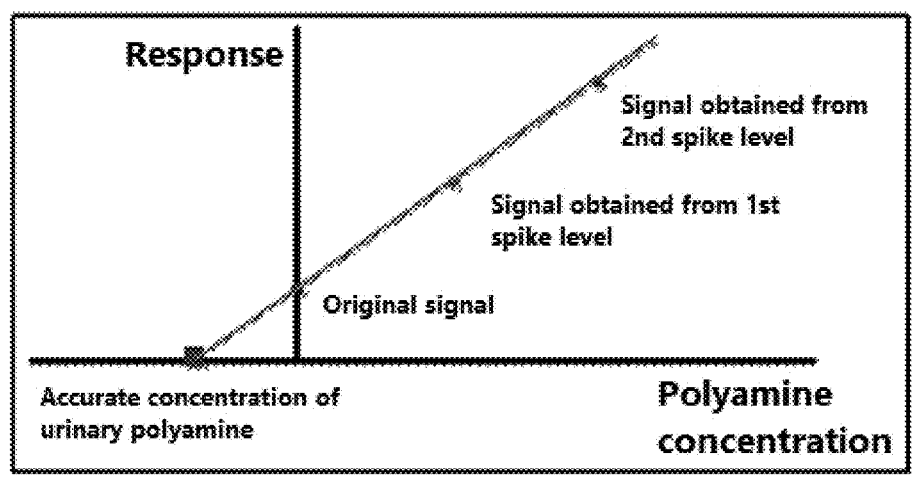
FIG. 11 shows the standard addition approach to define the concentrations of polyamines in urine samples.

Standard addition method, as shown in FIG. 11, will be used for the quantification by our developed bioprobe, which is a common method to solve the problems from matrix effect. Briefly, the signal of polyamines in urine sample will be measured and the result is plotted at concentration=x. The reading of 2 spiked levels will be measured, usually the 1 fold and 2 folds of the original concentration. The concentration of spiked level is written at x+A and x+B respectively. Upon extrapolating to the zero signal at the x-axis, the concentrations of polyamines in urine samples can be determined on the x-axis.

The mean values obtained by the two approaches were compared by Student's t tests where $P<0.05$ is considered to be statistically significant. There are not much differences between the readings obtained from luminescent complexes and the HPLC-MS/MS ($P<0.05$) and those readings are varied in a small range (% RSD<10). The inventor can conclude that the inventor's luminescent complexes are sensitive and reliable to detect polyamines in the urine samples. Analysis of the variation of sample frequency with Spm/Spd concentrations will be undertaken using standard statistical packages running in Origin. Equations are used to model a Gaussian distribution.

Determination of the Binding Affinity and Selectivity of Compound 1 with Spm/Spd in Aqueous Solution The developed compound 1 was examined through fluorescence and fluorescence lifetime titrations with various concentrations of the target Spm/Spd in solution and in biological media (simulated level of Spm—1.2 µM/Spd—11.9 µM in urine/blood). The physiological properties and detection limits of these sensors for Spm/Spd were also determined. Measurements were taken after attaining equilibrium, and the emission of the europium was monitored. Luminescent responses in terms of $I_0/(I-I_0)$ (where I and $I_0$ are the measured and blank luminescence intensities, respectively) were plotted as a function of the analyte concentration. For the determination of the binding strengths of the various analyte adducts, a series of analyte solutions at known concentrations were mixed with the Spm/Spd solutions at various concentrations. The binding constant, KB, was estimated from the ratio between the y-intercept and the slope that is to be obtained from the line of best fit using Benesi-Hildebrand equations. The signal changes of the lanthanide complex after binding with Spm/Spd may be induced by various mechanisms, such as the electron transfer process (Rehm-Weller equation) and redox potentials, and transient absorption with flash photolysis have been applied to understand the mechanism responsible for the change of the signal after the inventor's lanthanide systems tagging Spm/Spd.

A further embodiment of the present disclosure relates to an improved method for detecting Spm using an aptasensor gold nanoparticles (AuNPs).

Gold nanoparticles (AuNPs) emerged as a biocompatible nanomaterial and have been widely used in biomedical engineering and bioanalytical applications. For example colorimetric biosensing probes useful for detecting a wide variety of chemical species have been developed based on the red-shifting of their unique surface plasmon resonance band. Response can be viewed directly by naked eye upon any modulations of the aggregation state by the target analyte.

Disclosed herein is a comprehensive study on this phenomenon in connection with urinary polyamines. Different parameters of the diagnostic probe were evaluated, including the AuNPs size, DNA length, concentration, and pH towards. Based on these experiments, two sensing mechanisms of aptasensor were identified: depending on the amount of DNA being added, it either sensed based on the aggregation of DNA-AuNPS, which results in the red-shift of plasmonic band, or the precipitation of DNA-AuNPS which results in the decline of plasmonic band. The developed aptasensor could intelligently detect Spm via two different sensing mechanisms simply by changing the DNA concentration without complicated procedures. (FIG. 26)

The aptasensor also demonstrated good results in spike analysis of both artificial and clinical urine samples, and is capable of providing a useful secondary screening tool for of the quick detection of SPM, supplementing the conventionally used serum PSA test and potentially improving the outcome of PCa screening.

For the purposes of this disclosure, the terms "DNA", "DNA aptamer", and "single stranded DNA" are used interchangeably and refer to polynucleotides existing substantially in single strand form (e.g., greater than >60%, 70%, 80%, 90%, 95%, 98%, 99%, or 99.9% exists in single stranded form) not bound to a complimentary sequence. Examples, of single stranded DNA as disclosed herein include DNA aptamer 12mer: CGACAACCACAA (SEQ ID NO:1); DNA aptamer 24mer: CGACAACCACAACACACAATCTGA (SEQ ID NO:2); and DNA aptamer 36mer: CGACAACCACAACACACAATCTGACGACAACCACAA (SEQ ID NO:3).

Materials and Instrument

All chemicals were acquired from Aldrich (Hong Kong, China) and Meryer (Shanghai, China). DNA aptamers (12mer: CGACAACCACAA (SEQ ID NO:1); 24mer: CGACAACCACAACACACAATCTGA (SEQ ID NO:2); 36mer: CGACAACCACAACACACAATCTGACGACAACCACAA (SEQ ID NO:3)) were obtained from Invitrogen (Hong Kong, China). Britton-Robinson (BR) buffer was prepared by mixing equal molar ratio of phosphoric acid, boric acid and acetic acid, and the pH was then tuned using sodium hydroxide solution. Artificial urine was prepared according to a recipe elsewhere. All standard solutions were prepared in Milli-Q water. For urine samples, they were collected from Princes of Wales Hospital, The Chinese University of Hong Kong.

The transmission electron microscope (TEM) images of as-prepared AuNPs were captured using a JEOL Model JEM-2011 (JEOL, Beijing, China). Dynamic Light Scattering (DLS) and zeta-potential measurements were achieved by a Zetasizer Nano-ZS90 System (Malvern Instruments, Shanghai, China). The UV-Vis absorption spectra were recorded using a Cary 8453 UV-Vis Spectrometer (Agilent, Hong Kong, China). Isothermal Titration calorimetry study was achieved using MicroCal PEAQ-ITC Automated System (Malvern Instruments, Shanghai, China).

For urine sample analysis, liquid chromatography separation was done by an Agilent 1290 Infinity Quaternary LC System while mass analysis was done by an Agilent 6460 Triple Quadrupole mass spectrometer equipped with an Agilent Jet Stream technology electrospray ionization source (Agilent, Hong Kong, China). All the incubations were performed on a KS 260 Basic Orbital Shaker (IKA, Hong Kong, China).

Synthesis of Citrate-AuNPs

Figure 12:
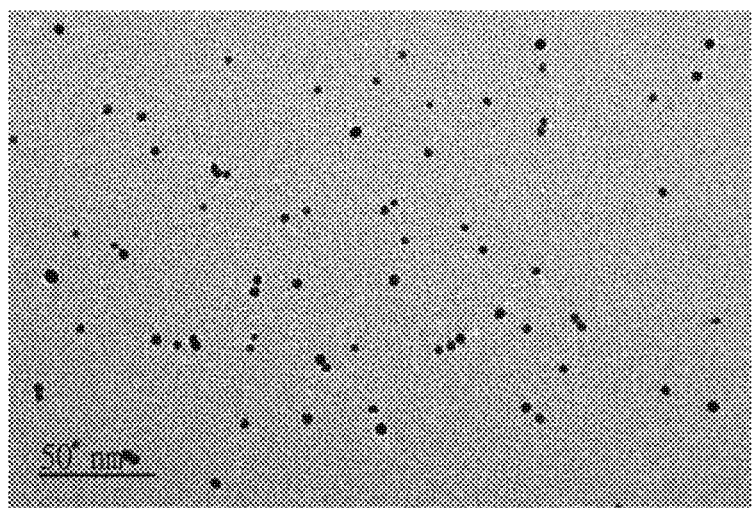
FIG. 12 shows the TEM image of citrate-AuNPs solution.

Three different sizes (4 nm, 13 nm, 27 nm) of AuNPs were prepared. For 4 nm citrate-AuNPs, synthesis of colloidal citrate-AuNPs was performed according to a previous published literature Gu, Y. J.; Cheng, J.; Lin, C. C.; Lam, Y. W.; Cheng, S. H.; Wong, W. T. *Toxicol. Appl. Pharm.* 2009, 237(2), 196. Briefly, chloroauric acid solution was mixed with trisodium citrate solution, then freshly-prepared sodium borohydride solution was added and left for 2 hours. For 13 nm and 27 nm AuNPs, the synthesis was done by the well-known Turkevich method, where trisodium citrate was used as both the reducing agent and capping ligands under refluxing condition. Final size as determined from TEM was 4.09±0.65 nm, 12.8±1.3 nm and 27.2±4.2 nm. (FIGS. 28A-28C). (FIG. 12) Concentration was calculated to be 114.54 nM for 4 nm AuNPs using equations suggested by Liu, et al. *Colloid. Surface. B* 2007, 58(1), 3. Concentration was calculated to be 14.15 nM and 1.53 nM for 13 nm and 27 nm AuNPs respectively using equations suggested by Liu et al. 4 nm AuNPs were employed for majority of experiments, and different batches' absorbance and wavelength of plasmonic band did not show significant deviations.

In certain embodiments, the size of the AuNP is between about 1 nm to about 100 nm. In certain embodiments, the size of AuNP is between about 1 nm to about 90 nm, about 1 nm to about 80 nm, about 1 nm to about 70 nm, about 1 nm to about 60 nm, about 1 nm to about 50 nm, about 1 nm to about 40 nm, about 1 nm to about 30 nm, about 1 nm to about 20 nm, about 1 nm to about 10 nm, about 2 nm to about 10 nm, or about 2 nm to about 7 nm.

Quantitative Detection of Spm by AuNPs

Firstly, 80 nM as-prepared AuNPs was vortex-mixed with 25 nM DNA aptamer inside 4 mM BR buffer (pH=3.29) for selective adsorption to take place. Spm standard/sample solution was then added and incubated for 40 minutes. The mixture was then ready for UV-Vis absorption, DLS and zeta-potential measurements. In complicated matrices like artificial urine and clinical urine, DNA concentration was raised to 100 nM to provide a better protection.

Optimization of Working Conditions

Several parameters including AuNPs size (4, 13, 27 nm), DNA aptamer concentration (12.5, 25, 50, 100 & 200 nM), DNA length effect (12mer, 24mer & 36mer), pH (1.81, 3.29, 4.96, 6.99, 8.98 & 11.0) and length of incubation time were optimized based on the sensitivity towards Spm.

Sample Pretreatment Procedures

Briefly, a urine sample was thawed naturally and centrifuged for 5 minutes at 13000 rpm and 25° C. Then it was passed through strong anion exchange solid phase extraction cartridge (Phenomenex, Strata, 100 mg/3 ml, USA) to retain unwanted organic acids, phenolic compounds and carbohydrates. Afterwards the solution was treated with concentrated perchloric acid for further deproteinization, which was then removed by neutralization using potassium hydroxide solution to form insoluble potassium perchlorate salt. Finally it was centrifuged again to obtain supernatant, filtered with 0.22 uM PES filter and further diluted in water.

Isothermal Titration Calorimetry Study

For the study of interactions between DNA/citrate AuNPs and Spm, the AuNPs was firstly pre-concentrated using Amicon Ultra-15 30K centrifugal filter (Millipore, Hong Kong, China). Afterwards, 0.5 µM AuNPs and different concentration of DNA aptamer (0, 0.5, 1 & 3 µM) were firstly mixed and placed into the sample cell. 0.25 mM Spm solution was then gradually added for recording the temperature change per injection (24, per injection in 150 s interval at 25° C.).

For the study of selectivity of citrate against polyamines analogs, 1 mM trisodium citrate solution was firstly placed into sample cell, then 0.8 mM of different polyamine analogs solution was injected independently for recording the temperature under the above-mentioned conditions.

Data was then fitted the binding model of one site of binding and analyzed by the MicroCal PEAQ-ITC Analysis software.

Quantitative Detection of Spm by UPLC-MS/MS

The quantitation of Spm was performed by Ultra-high Performance Liquid Chromatography coupled with a triple quadrupole mass spectrometer (UPLC-MS/MS). LC separation was done by an Agilent 1290 Infinity Quaternary LC System while mass analyzing was done by an Agilent 6460 Triple Quadrupole mass spectrometer equipped with an Agilent Jet Stream technology electrospray ionization source. The column used was an Agilent EclipsePlus C18

RRHD (2.1×50 mm, 1.8 μm) protected with an Agilent SB-C18 guard column (2.1×5 mm, 1.8 μm).

The LC elution profiles were optimized as follows: Eluent A was water with 0.1% HFBA while eluent B was acetonitrile with 0.1% HFBA. Eluent A was decreased from 95% to 60% in 10 minutes. The gradient was then decreased from 60% to 10% of eluent A in 1 minute. Afterwards the gradient was held constant for 5 minutes. The gradient was then increased from 10% to 95% in 1 minute, followed by being held constant for 8 minutes. (Total run-time=25 minutes).

Autosampler and column temperature were set as 4° C. and 35° C. respectively. Injection was achieved by 5-second needle wash in Flush Port mode for 3 times with eluent B. In each time 10 μL was injected.

For the source parameter, drying gas (nitrogen) temperature was set as 300° C. with 5 L/min flow rate. Nebulizer pressure was 45 psi. Sheath gas temperature was set as 250° C. with 11 L/min flow rate. Capillary voltage was set as 3500V. For mass detection, scheduled multiple reaction monitoring (MRM) was performed.

Results & Discussion

Working Principle

Figure 13:
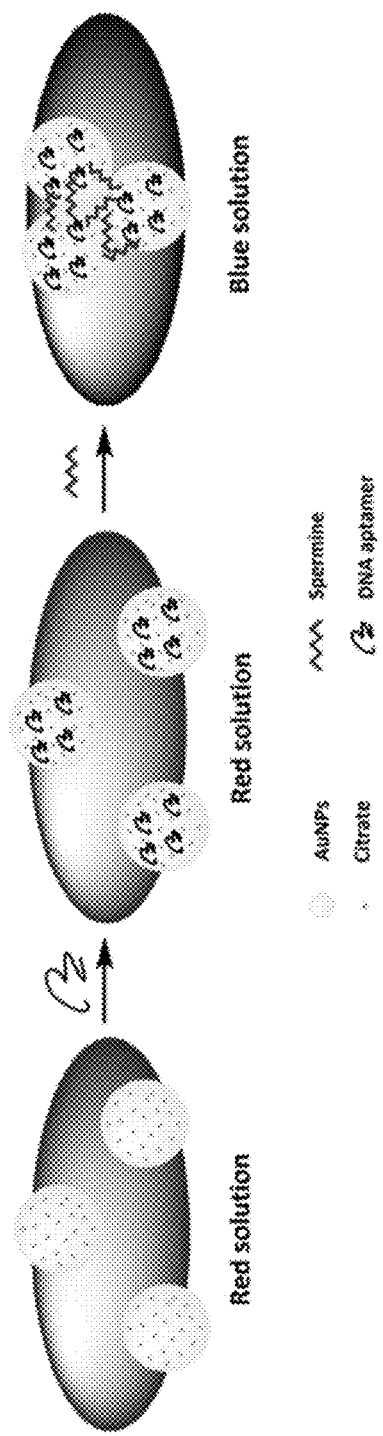
FIG. 13 shows the schematic diagram of current developed aptasensor.

Sensitive and specific sensing towards Spm was achieved by the current developed aptasensor via two stages: The first stage, as being demonstrated in FIG. 27, started with the selective adsorption of DNA aptamer onto surface of citrate-AuNPs, which is induced by a low pH working condition and the later addition of Spm for neutralizing the negative charge on surface of AuNPs. Zhang et al. *Langmuir* 2012, 28, 3896 has systematically studied the adsorption process and proposed a binding model before. Citrate ligands were being displaced since DNA could adopt an extended conformation to strengthen the binding with AuNPs surface. This phenomena can be observed by studying the DLS result that with more DNA, the hydrodynamic size of AuNPs became smaller and smaller due to the displacement of citrate layer by a more compact DNA molecule. (FIG. 29) The better stabilization effect by DNA was also reflected from that decrease in Z-average value in acidic condition, which could make AuNPs aggregate. This protection effect against aggregation was also shown in another experiment (FIG. 30), which clearly demonstrated that the aggregation driven by the presence of salt had slowed down at a high DNA capping condition. The second stage was the addition of positively charged SPM for inducing further DNA adsorption by shielding the negative charges on both AuNPs and DNA aptamer, and as results weakening the repulsion force for AuNPs aggregation. FIG. 13 shows the working principle of the aptasensor. The extent of aggregation would therefore allow an indirect quantitation of SPM content in a convenient and fast manner.

To further study the driving force of citrate displacement by DNA, it was well studied before that the presence of salt would screen the charge repulsion between negatively charged AuNPs and DNA. In the inventors' case, the AuNPs are used directly without any clean-up. Therefore a lot of free citrate molecules and side products from sodium borohydride would act as such screening sources for DNA adsorption. A proof-of-concept experiment was performed to remove these free salts by ultrafiltration. It was found that without them, DNA cannot attach and the AuNPs would aggregate immediately upon addition of acidic BR buffer for protonating the citrate groups, even in the presence of DNA. And vice versa, when stock AuNPs solution was used, aggregation did not happen. This confirms the importance of free citrate and other salts for the aptasensor to function properly.

Optimization of Working Conditions

Working condition parameters as discussed below were studied and optimized carefully so as to maximize the analytical performance of the aptasensor for SPM sensing in urine. This was achieved by studying the slope of SPM calibration graphs, which reflects the corresponding sensitivity in each case, and the linear working range to fit the urinary content of SPM. The first parameter the inventors studied was the size effect of AuNPs. As being illustrated in FIG. 31, by taking logarithm of the absorbance ratio at 610 nm and their plasmonic peaks, the sensitivity becomes greater and linear range become narrower with the increase of AuNPs size. Considering the fact that most urine samples have urinary Spm content in the range of 0-15 μM, 4 nm AuNPs seemed to be the best choice for later experiments by providing the widest and most appropriate linear working range. Without wishing to be bound by theory, it was believed that the number of AuNPs was smaller in cases of larger AuNPs, which resulted in a greater tendency to aggregate at the same concentration of Spm being added into the AuNPs solution.

Figure 14:
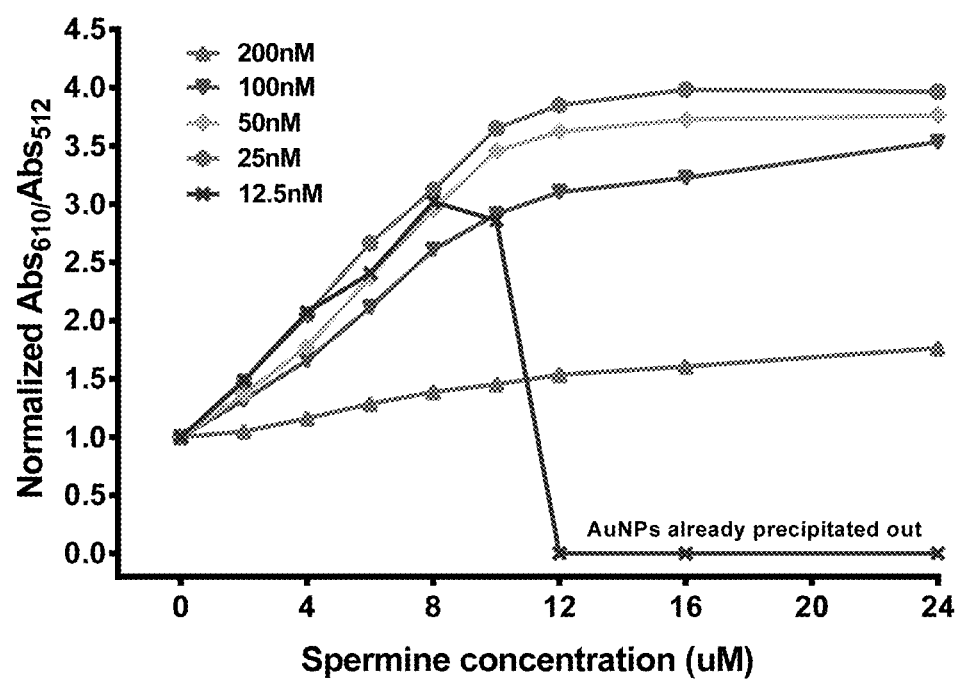
FIG. 14 shows DNA effect on Spm calibration graph.

The second parameter is the DNA concentration. (FIG. 14 and Table 6) Basically, in all cases the observed curve was linear initially, which then gradually leveled off. And with more DNA, a wider linear working range was obtained at the cost of sensitivity. Due to the nature of non-cross-linking aggregation approach in this method, the preparation of DNA-AuNPs through tedious target-directed surface modifications was not necessary. Flexibility was therefore conferred on users to tune the working range simply by changing the DNA amount added to AuNPs. Finally, the concentration of DNA aptamers for detection of Spm/Spd ranges from 20 nM to 500 nM and 25 nM was chosen as the optimal concentration.

TABLE 6

Summarized results on the linear equation, $R^2$ and linear range of Spm calibration graphs at different DNA concentration.

| DNA concentration (nM) | Equation | R2 | Linear range |
|---|---|---|---|
| 12.5 | y = 0.2305x + 1.0134 | 0.9975 | 0-4 uM |
| 25 | y = 0.2657x + 0.9893 | 0.9988 | 0-6 uM |
| 50 | y = 0.2258x + 0.9987 | 0.9968 | 0-10 uM |
| 100 | y = 0.1972x + 1.0578 | 0.9959 | 0-10 uM |
| 200 | y = 0.0529x + 0.9981 | 0.9926 | 0-16 uM |

The ratio of single stranded DNA to the gold nanoparticle can be selected, based in part on the complexity of the test sample.

In certain embodiments, for example, when the test sample consists of a complex matrix (e.g., clinical samples, artificial urine, artificial blood, or other samples with high quantities of interfering analytes), the molar ratio of the single stranded DNA to the gold nanoparticle is between about 4:1 to about 3:1 in the test sample. In certain embodiments, the molar ratio the single stranded DNA to the gold nanoparticle is between about 4:1 to about 3:1, about 3.9:1 to about 3:1, about 3.8:1 to about 3:1, about 3.7:1 to about 3:1, about 3.6:1 to about 3:1, about 3.5:1 to about 3:1, about 3.4:1 to about 3:1, about 3.3:1 to about 3:1, about 3.2:1 to about 3:1, or about 3.2:1 to about 3.1:1 in the test sample.

In other embodiments, for example, when the test sample consists of a simple matrix, the molar ratio of the single stranded DNA to the gold nanoparticle is between about 1:3 to about 1:4 in the test sample. In certain embodiments, the molar ratio of the single stranded DNA to the gold nanoparticle is between about 1:3 to about 1:4, about 1:3 to about 1:3.9, about 1:3 to about 1:3.8, about 1:3 to about 1:3.7, about 1:3 to about 1:3.6, about 1:3 to about 1:3.5, about 1:3 to about 1:3.4, about 1:3.1 to about 1:3.4, or about 1:3.1 to about 1:3.3 in the test sample.

In certain embodiments, for example, when the test sample consists of a complex matrix (e.g., clinical samples, artificial urine, artificial blood, or other samples with high quantities of interfering analytes), the concentration of the single stranded DNA is about 200 nM to about 300 nM and the concentration of the gold nanoparticle is about 50 nM to about 100 nM in the test sample. In certain embodiments, the concentration of the single stranded DNA is about 220 nM to about 280 nM and the concentration of the gold nanoparticle is about 60 nM to about 100 nM; the concentration of the single stranded DNA is about 240 nM to about 260 nM and the concentration of the gold nanoparticle is about 70 nM to about 100 nM; the concentration of the single stranded DNA is about 245 nM to about 255 nM and the concentration of the gold nanoparticle is about 70 nM to about 90 nM; or the concentration of the single stranded DNA is about 245 nM to about 255 nM and the concentration of the gold nanoparticle is about 75 nM to about 85 nM in the test sample.

In certain embodiments, the concentration of the single stranded DNA is about 240 nM to about 260 nM and the concentration of the gold nanoparticle is about 75 nM to about 87 nM in the test sample.

Figure 15:
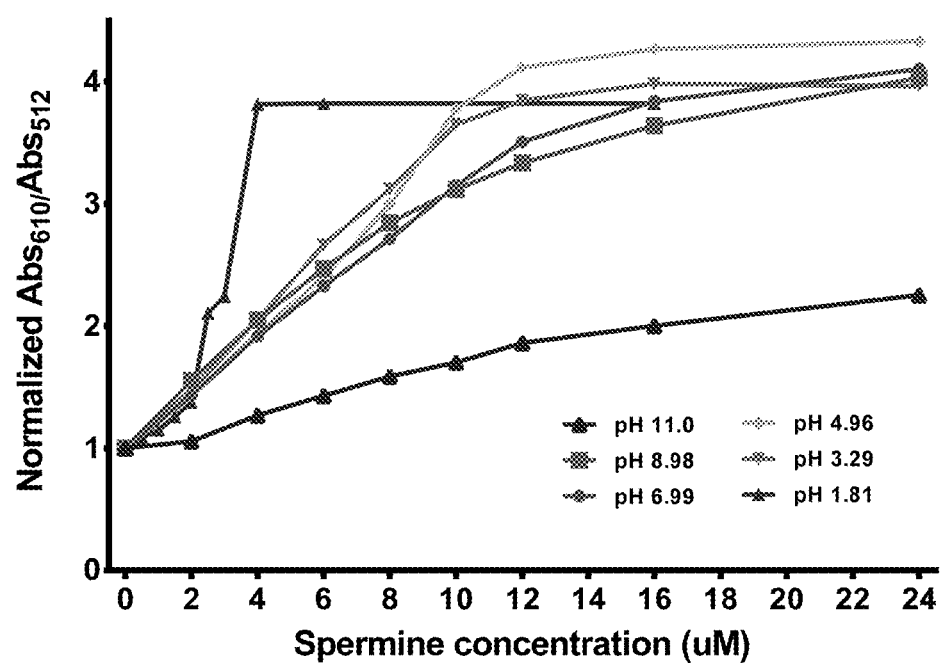
FIG. 15 shows the pH effect on Spm calibration graph.

The third parameter was the pH. (FIG. 15 and Table 7) The observed data indicated that the aptasensor worked well in acidic medium, which is essential to maintain Spm (pKa=7.90, 8.83, 9.97 & 10.79) in its +4 charge state. A low pH condition also helped DNA to adsorb onto AuNPs more easily. Finally, the pH value of the medium for detection of Spm/Spd ranges from 3 to 8 and 3.29 was chosen as the optimal pH.

TABLE 7

Summarized results on the linear equation, $R^2$ and linear range of Spm calibration graphs at different pH.

| pH | Equation | $R^2$ | Linear range |
|---|---|---|---|
| 3.29 | y = 0.2657x + 0.9893 | 0.9988 | 0-6 uM |
| 4.96 | y = 0.2510x + 0.9708 | 0.9944 | 0-10 uM |
| 6.99 | y = 0.2021x + 1.0845 | 0.9945 | 0-12 uM |
| 8.98 | y = 0.2321x + 1.0862 | 0.9914 | 0-8 uM |
| 11.0 | y = 0.0822x + 0.8323 | 0.9996 | 2-8 uM |

In certain embodiments, the method is conducted at a pH between about 2 to about 8, about 2 to about 7, about 2 to about 6, about 2 to about 5, about 2 to about 4, about 3 to about 4, or about 3 to about 3.5.

In certain embodiments, the method is conducted at a pH between about 3 to about 8, about 3 to about 7, about 3 to about 6, about 3 to about 5, about 3 to about 4, or about 3 to about 3.5.

Figure 16:
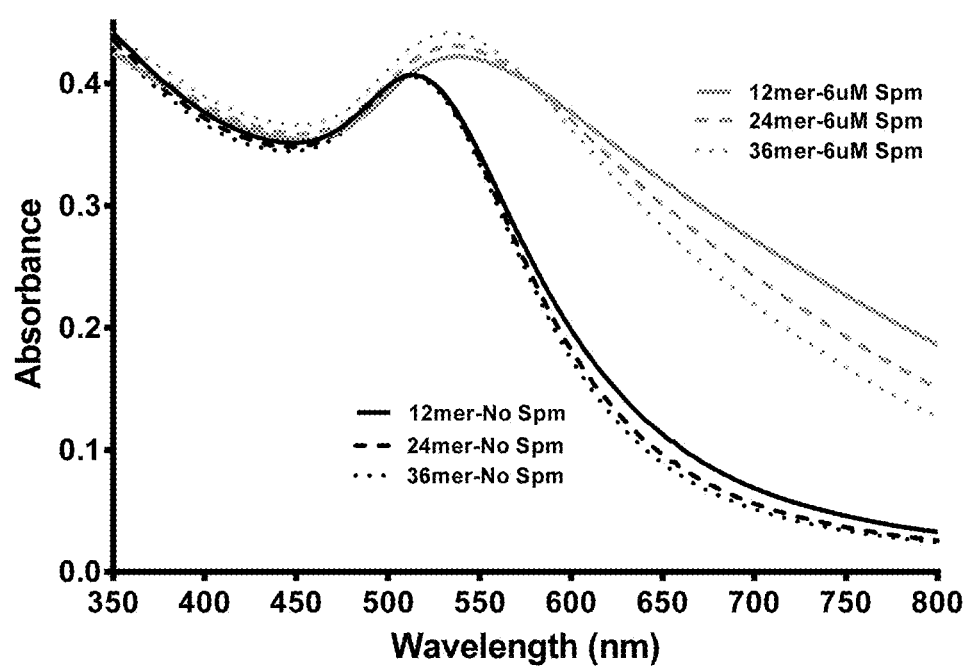
FIG. 16 shows the Absorption spectrum showing DNA length effect. (DNA sequence.

For the effect of DNA length, longer aptamer yields a more stable AuNP complex and protects AuNPs better from aggregation. (FIG. 16) When considering the absorbance change, 24-mer was the greatest so it was chosen. The last parameter was the monitoring of aggregation kinetics, and it was determined that 40 min was enough for reaching equilibrium. (FIG. 17)

In certain embodiments, the single stranded DNA has a length of about 5 nucleotides to about 50 nucleotides, about 5 nucleotides to about 45 nucleotides, about 5 nucleotides to about 40 nucleotides, about 5 nucleotides to about 35 nucleotides, about 5 nucleotides to about 30 nucleotides, about 10 nucleotides to about 30 nucleotides, about 15 nucleotides to about 30 nucleotides, or about 20 nucleotides to about 30 nucleotides.

Under the final optimal conditions, a linear Spm calibration curve from 0-5 µM can be fitted by least square linear regression. (FIGS. 18A and 18B) The equation was y=0.129x−0.4941, with limit of detection (LOD) and limit of quantitation (LOQ) calculated to be 15.25 nM (3.09 ng/ml) by the 3σ of Spm-free AuNPs solution and 50.82 nM respectively. After switching to 4 nm AuNPs, it demonstrated a noteworthy improvement in both sensitivity and working range. DLS and zeta-potential were also measured under the described conditions. (FIG. 19) The particle size increased with elevating Spm concentration for causing a larger degree of aggregation, but unlike the results from Liu et al. *Talanta* 2013, 106, 255 for 13 nm AuNPs, the inventor's results showed that the size of the citrate-Au nanoparticles for detection of Spm/Spd ranges from 1 nm to 100 nm and the zeta-potential of 4 nm AuNPs remained nearly constant instead of gradually restoring to a more positive level. This might be due to most SPM molecules being embedded in the core of aggregates.

Mechanistic Study on AuNPs Aggregation

During the optimization of DNA concentration, it was surprising to observe a drop of sensitivity to Spm when more DNA was added during the assay. This contradicted the accepted theory that Spm-induced aggregation occurred through DNA molecules by the ion-bridging effect. A control experiment in the absence of DNA was performed to gain more information. Surprisingly, the Spm-induced aggregation process could still be detected and exhibited faster initial kinetics rates, as compared with assays conducted in the presence of DNA. (FIG. 20) It seemed the presence of citrate groups originally capped on AuNPs could not be neglected and they contributed significantly to the aggregation process.

To have a deeper insight into the mechanism, the inventors performed several ITC experiments: Same amount of citrate capped AuNPs was firstly mixed with different DNA concentrations (0, 0.5, 1 and 3 µM) separately. Spm solution was then added gradually and the temperature change was measured for each injection. The results are shown in FIGS. 21A-21H and Table 8. In each case, the binding isotherm showed an enthalpic peak deviating from the fitting model. Rautaray et al *Langmuir* 2005, 21, 5185 reported a similar observation when they studied the interaction of $Ca^{2+}$ and aspartic acid-capped AuNPs, suggesting the peak was due to the aggregation of AuNPs as a consequence of neutralization of charge by $Ca^{2+}$ ion.

TABLE 8

Thermodynamic parameters of the binding of Spm to AuNPs at differen tDNA concentration.

| DNA concentration (µM) | $K_D$ (M) | ΔH (kcal/mol) | ΔG (kcal/mol) | TΔS (kcal/mol) |
|---|---|---|---|---|
| 0 | 8.13E−06 | −67.9 | −6.95 | −61.0 |
| 0.5 | 2.03E−06 | −13.4 | −7.77 | −5.68 |
| 1 | 3.45E−07 | −8.40 | −8.82 | 0.418 |
| 3 | 4.72E−07 | −7.52 | −8.63 | 1.12 |

When more DNA was added, the enthalpic peak gradually shifted to the right as at higher molar ratios of SPM to AuNP, implying that the AuNPs aggregation could only be initiated at a higher concentration of SPM. This data matched well with the results from UV-Vis absorption measurements which revealed the decline of sensitivity towards SPM at a higher DNA concentration. After analyzing the thermodynamic parameters, it could be concluded that the Spm-induced aggregation mainly happened via an enthalpy-driven electrostatic/hydrogen-bonding interaction with both DNA and citrate as reflected from the comparatively large negative values of ΔH. The entropy component gradually became more favorable as the DNA concentration increased, but enthalpy remained as the major driving force. Therefore, the drop of ΔH strength with increasing DNA concentrations implied the weakening of such electrostatic/hydrogen-bonding interactions (Table 9). From these results, it was hypothesized that Spm interacted with AuNPs electrostatically primarily through the surface citrate ligands, but not through DNA aptamers. The role of DNA in the current aptasensor was to displace surficial citrate ligands to provide protection to AuNPs, and concurrently to control the extent of citrate-Spm interaction and thus AuNPs' aggregation rate and therefore the analytical performance of the aptasensor.

TABLE 9

Thermodynamic parameters of the binding of DNA to different polyamine analogs.

| Analyte | Fitness of binding model | $K_D$ (M) | ΔH (kcal/mol) | ΔG (kcal/mol) | TΔS (kcal/mol) |
|---|---|---|---|---|---|
| Spermine | Good | $1.10 \times 10^{-6}$ | −7.83 | −8.13 | 0.308 |
| Spermidine | Good | $1.11 \times 10^{-6}$ | −4.44 | −8.13 | 3.69 |
| Histamine | Good | $1.27 \times 10^{-5}$ | −3.61 | −6.68 | 3.07 |
| Putrescine | Good | $3.97 \times 10^{-5}$ | −7.29 | −7.37 | 0.08 |
| Arginine | Good | $1.42 \times 10^{-5}$ | −4.59 | −6.61 | 2.03 |
| Tyramine | Good | $3.06 \times 10^{-5}$ | −13.6 | −6.16 | −7.46 |
| Cadaverine* | Good | $9.33 \times 10^{-6}$ | 1.06 | −6.86 | 7.93 |
| Ornithine | Cannot be fitted | N/A | N/A | N/A | N/A |
| Control (water) | Cannot be fitted | N/A | N/A | N/A | N/A |

*Cadaverine interacted with DNA following an endothermic pathway.

To further confirm the importance of surface citrate during aggregation, an additional ITC experiment was conducted to study the interactions between pure citrate ligands and other polyamine analogs. (Table 10) Although there are three carboxylate groups in free citrate for interaction, only one remained when being capped onto AuNPs; and the ΔH strength sequence (Spermine>Spermidine>Histamine>Putrescine>Arginine>Tyramine=Cadaverine=Ornithine=Creatinine=Control) was very similar to that of the cross-reactivity sequence (Spermine>Spermidine>Histamine>Putrescine=Arginine=Tyramine=Cadaverine=Ornithine=Creatinine=Control) determined from UV-Vis absorption measurements but not to that of the DNA. Table 9 and 10 for the summarized thermodynamics data of free citrate and DNA obtained from ITC. (FIG. 22) This result showed the importance of citrates in achieving aggregation.

TABLE 10

Thermodynamic parameters of the binding of citrate to different polyamine analogs.

| Analytes | Binding | N (sites) | $K_D$ (M) | ΔH (kcal/mol) | ΔG (kcal/mol) | TΔS (kcal/mol) |
|---|---|---|---|---|---|---|
| Spermine | Binding | 1.40E−02 | 1.26E−06 | −36.9 | −8.05 | −28.8 |
| Spermidine | Binding | 3.80E−02 | 2.11E−06 | −18.4 | −7.74 | −10.7 |
| Histamine | Binding | 9.96 | 6.56E−03 | −15.6 | −2.98 | −12.7 |
| Putrescine | Binding | 4.10E−02 | 1.41E−06 | −14.5 | −7.98 | −6.54 |
| Arginine | Binding (Poor) | 3.68 | 3.65E−03 | −6.45 | −3.33 | −3.13 |
| Tyramine | Binding (Poor) | 0.102 | 3.88E−06 | −0.24 | −7.38 | 7.14 |
| Cadaverine | No binding | N/A | N/A | N/A | N/A | N/A |
| Ornithine | No binding | N/A | N/A | N/A | N/A | N/A |
| Creatinine | No binding | N/A | N/A | N/A | N/A | N/A |
| Control (water) | No binding | N/A | N/A | N/A | N/A | N/A |

Finally, to study if DNA really took part in the interactions, the selectivity profile of AuNPs against polyamine analogs at different DNA concentrations was monitored. Each of their cross-reactivity was determined by comparing the $Abs_{610}/Abs_{512}$ to that of Spm. Upon modulating the capping ratio by adding more DNA for displacing citrate, a change on the overall selectivity profile of AuNPs was expected. However, after normalization, FIG. 22 indicated that there was not much change among different conditions, meaning that DNA indeed had no or very little interactions with Spm and other analogs in causing any changes in the overall selectivity of AuNPs. While pure DNA alone showed some electrostatic interactions with Spm in the isothermal titration calorimetry (ITC) experiment (FIGS. 23A-23B), DNA adsorbed on AuNPs surface is believed to have adapted an extended conformation, maximizing its surface contact and strengthening the binding with AuNPs. This DNA compaction process may disfavor further interaction with Spm.

Application of Aptasensor in Real Samples

To demonstrate that the current developed aptasensor was fitted for its intended purpose for detecting Spm, its applicability was being tested in one of the most Spm-content concerning sample: urine. Artificial urine was prepared to mimic clinical urine during early investigation. Unfortunately, under the described optimal condition, the aptasensor failed to work properly since artificial urine contains a high salt concentration which could effectively screen negative charges for aggregation. AuNPs could not tolerate it even in the absence of Spm. The origin of such an undesired aggregation was a result of insufficient AuNPs protection by the surfactants. Clearly addition of only 25 nM DNA was not enough for working in such complicated matrix and to provide further protection, the working DNA concentration was elevated to 250 nM. FIG. 24 showed the titration profile of DNA-AuNPs absorption spectrum against artificial urine with different dilution factor. With more matrix components, which were mainly inorganic salts, the absorbance of plasmonic peak declined gradually owing to the greater extent of DNA adsorption. Results showed that 250 nM DNA was enough to protect AuNPs from aggregation up to two-fold diluted artificial urine.

Spm was spiked into artificial urine and FIG. 25 showed the absorption spectrum and corresponding calibration curve. Surprisingly, AuNPs responded to Spm with a totally different mechanism compared to that in blank matrix. As revealed from the absorption pattern, with a higher Spm concentration, the plasmonic peak declined gradually similar to the previous titration study of artificial urine matrix effect. It confirmed that Spm could also help to screen negative charges like salts and induced further DNA adsorption. Therefore a greater extent of DNA adsorption or even AuNPs precipitation was observed upon addition of Spm and both of them accounted for the drop of plasmonic band. The decrease was also found to correlate with Spm concentration with a linear relationship, and the LOD for Spm was calculated to be 473.29 nM. A wider linear calibration curve from 0-18 µM could be obtained which matched perfectly with that of general urinary Spm content. Spike analysis in artificial urine by a matrix-match calibration approach gave both satisfactory recovery and reproducibility. (Table 11)

TABLE 11

Determination of spiked SPM in artificial urine specimen. (n = 3)

| Sample | Amount spiked (µM) | Average recovery (%) | Relative standard deviation (%) |
|---|---|---|---|
| Artificial urine | 2.0 | 87.90 | 5.46 |
| | 4.0 | 100.61 | 0.07 |
| | 6.0 | 94.76 | 2.65 |
| | 8.0 | 106.70 | 2.01 |
| Urine 1 | 3.0 | 98.80 | 9.52 |
| Urine 2 | 3.0 | 121.98 | 7.76 |
| Urine 3 | 3.0 | 104.09 | 4.21 |

To further demonstrate the applicability of the aptasensor for a fast urinary Spm screening, three clinical urine samples from cancerous patients were selected for further spike analysis. Before that, common urinary components (Urea, uric acid, glutathione, human serum albumin, calcium salt and creatinine) were tested to check if they interfered seriously with Spm sensing. (FIG. 26) Results showed that only human serum albumin would cause slight AuNPs aggregation since proteins tend to be highly charged molecules. Therefore all the pre-spiked clinical urine samples were passed through Amicon centrifugal filter to remove any large protein molecules and then analysed by the aptasensor again by a matrix-match calibration approach. The satisfactory accuracy and relative standard deviation values demonstrated the applicability of the aptasensor in real samples. (Table 12)

TABLE 12

Determination of spiked SPM in clinical urine specimen. (n = 3)

| Clinical sample | Amount spiked (µM) | Average recovery (%) | Relative standard deviation (%) |
|---|---|---|---|
| 1 | 3.0 | 98.80 | 9.52 |
| 2 | 3.0 | 121.98 | 7.76 |
| 3 | 3.0 | 104.09 | 4.21 |

To demonstrate the usefulness of current developed aptasensor, the Spm content of low concentration Spa human urine was evaluated. Four urine samples with insignificant Spm level, as determined by UPLC-MS/MS (<5 ppb), were chosen for studying the matrix effect. Unfortunately, the matrix effect differed from sample to sample, especially in urine sample 3 (green curve in FIGS. 32A-32C) which caused serious aggregation on AuNPs even in the absence of Spm. It was believed that proteins may be the cause of interference in the urine, so the use of perchloric acid for deproteinization to precipitate the unwanted proteins was incorporated into the method. FIGS. 32A-32C present the benefit of deproteinization of the urine sample in the method. However, a small difference was still seen and this could pose a negative effect on real sample analyses. The origin of such an unequal initial aggregation state was due to insufficient protection of AuNPs, therefore the DNA concentration was further optimized. After elevating the DNA concentration from 25 nM to 100 nM, the results were eventually identical. FIG. 25 showed the calibration curve inside the urine matrix. A wider linear Spm calibration curve from 0-10 µM can be fitted by least square linear regression. The equation was y=0.03843x−0.4344, with LOD and LOQ calculated to be 178 nM and 594 nM respectively. A completely different aggregation pattern was also noticed when compared to that in blank matrix.

The matrix effect of urine with that of blank and artificial urine solution was compared, but no distinct differences were observed. (FIG. 33) Therefore in the later spike analysis, the matrix-match calibration approach was employed. Table 13 shows the results of spike analysis in three urine specimen at two spike levels on two different days. The recovery and reproducibility were both satisfactory.

TABLE 13

Spike Analysis in urine specimen (n = 2)

| Sample | Amount spiked (µM) | Average recovery (%) | Relative standard deviation (%) |
|---|---|---|---|
| Urine 1 | 1.0 | 93.26 | 6.60 |
| | 3.0 | 98.80 | 9.52 |
| Urine 2 | 1.0 | 99.29 | 4.90 |
| | 3.0 | 121.98 | 7.76 |
| Urine 3 | 1.0 | 93.51 | 2.68 |
| | 3.0 | 104.09 | 4.21 |

To further show that the aptasensor was fit for intended purpose of fast urinary Spm screening, the original Spm level present in selected urine samples was determined. Results were compared to that of UPLC-MS/MS which acted as a reference method. (Table 14)

TABLE 14

Quantitation of Spm in urine specimen by UPLC-MS/MS and current developed method

| | By UPLC-MS/MS | | By developed aptasensor | | |
|---|---|---|---|---|---|
| | Average spermine found (µM) | RSD (%) | Average spermine found (µM) | RSD (%) | Average recovery (%) |
| Urine 5 | 29.18 | 2.51 | 28.52 | 5.06 | 97.75 |
| Urine 6 | 13.26 | 0.92 | 14.33 | 2.02 | 108.08 |
| Urine 7 | 10.75 | 1.17 | 12.94 | 7.61 | 120.34 |

Optical Method for Determination of Urinary Biogenic Amines by Metal-Organic Framework (MOF)

The rapidly emerging interest in the evaluation of biogenic amines especially Spd and Spm has brought up new demands for efficacious technical methods. These amines are abundantly present in human urinary excretion. For the simultaneous quantification of Spd and Spm in both aqueous and urinary phase, an optical method relying on the efficient application of Metal-Organic Framework (MOF) is currently under development. The sensor is designed in such a way that the framework offers unsaturated metal ions coordination spheres for the penetration and binding of small and cationic species. The complementarity of binding sites that prevailed in biogenic amine and steric requirements of the cation coordination sphere will govern the selectivity for biogenic amine, providing a good specificity towards target amines.

The method will allow visual naked-eye determination as the color of the aqueous solution of MOF upon the addition of Spd and Spm individually. Further titration experiments of MOF sensor against increasing concentration of Spd and Spm will be performed to examine the linear relation of absorbance for quantitative purpose. Eventually, the real sample application of proposed MOF sensor will be validated using artificial urine and clinical urine samples from prostate cancer patients. Any modulations in chromogenic signals being observed; i.e., change in color of the sensor solution when reacting with urinary biogenic amines, will allow a simple and direct quantitation of these high-interest analyzes for cancer screening.

INDUSTRIAL APPLICATIONS

The present invention relates to urinary polyamines for prostate cancer biomarkers. In particular, the present invention provides a novel, highly-sensitive and specific, and colour-changing polyamines tracer with the use of lanthanide complexes or citrate-AuNPs with DNA aptamer as prostate cancer diagnostic biomarker for early prostate cancer screening, which has a great potential to be applied in future clinical diagnosis.

I claim:
1. A compound of formula (1):

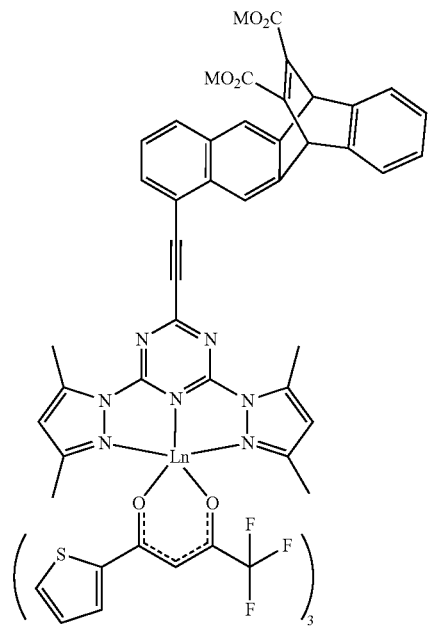

wherein,
Ln is a lanthanide metal; and
each M is independently selected from the group consisting of Na, Li, and K; or two M taken together represent Mg or Ca.

---

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Artificial DNA Sequence Synthesized in the Lab

<400> SEQUENCE: 1
cgacaaccac aa                                                          12

<210> SEQ ID NO 2
<211> LENGTH: 24
<212> TYPE: DNA
<213> ORGANISM: Artificial Sequence
<220> FEATURE:
<223> OTHER INFORMATION: Artifical DNA Sequence Synthesized in the Lab

<400> SEQUENCE: 2
cgacaaccac aacacacaat ctga                                             24

<210> SEQ ID NO 3
<211> LENGTH: 36
<212> TYPE: DNA
<213> ORGANISM: Artificial Sequence
<220> FEATURE:
<223> OTHER INFORMATION: Artifical DNA Sequence Synthesized in the Lab

<400> SEQUENCE: 3
cgacaaccac aacacacaat ctgacgacaa ccacaa                                36
```

2. The compound of claim 1, wherein the lanthanide is europium.

3. The compound of claim 1, wherein M is Li.

4. A method of detecting one or more urinary polyamines, comprising the steps of:
 a. providing a urine sample;
 b. contacting the urine sample with a compound of claim 1 thereby forming a test sample; and
 c. detecting the presence of the one or more urinary polyamines in the test sample.

5. The method of claim 4, wherein the urine sample is obtained from a human.

6. The method of claim 5, wherein the concentration of the one or more urinary polyamines is used to determine whether the human suffers from prostate cancer.

\* \* \* \* \*